United States Patent
Stevenson et al.

(10) Patent No.: US 9,042,999 B2
(45) Date of Patent: May 26, 2015

(54) LOW LOSS BAND PASS FILTER FOR RF DISTANCE TELEMETRY PIN ANTENNAS OF ACTIVE IMPLANTABLE MEDICAL DEVICES

(75) Inventors: Robert A. Stevenson, Canyon Country, CA (US); Warren S. Dabney, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 1416 days.

(21) Appl. No.: 11/840,131

(22) Filed: Aug. 16, 2007

(65) Prior Publication Data
US 2008/0195180 A1  Aug. 14, 2008

Related U.S. Application Data

(63) Continuation-in-part of application No. 11/423,073, filed on Jun. 8, 2006, now Pat. No. 8,244,370, and a continuation-in-part of application No. 11/558,349, filed on Nov. 9, 2006, now Pat. No. 7,945,322, and a (Continued)

(51) Int. Cl.
*A61N 1/08* (2006.01)
*A61N 1/05* (2006.01)
(Continued)

(52) U.S. Cl.
CPC .. *A61N 1/05* (2013.01); *A61N 1/37* (2013.01); *A61N 1/3718* (2013.01); *A61N 2001/086* (2013.01); *H03H 1/0007* (2013.01); *H03H 7/175* (2013.01); *H03H 7/1775* (2013.01)

(58) Field of Classification Search
CPC ............................ A61N 2001/086; A61N 1/05
USPC ................................... 607/116, 122; 600/421
See application file for complete search history.

(56) References Cited

U.S. PATENT DOCUMENTS

| | | | |
|---|---|---|---|
| 3,871,382 A | 3/1975 | Mann | |
| 3,968,802 A | 7/1976 | Ballis | |

(Continued)

FOREIGN PATENT DOCUMENTS

| | | |
|---|---|---|
| EP | 0 498 996 B1 | 3/1997 |
| JP | 60141034 | 7/1985 |

(Continued)

OTHER PUBLICATIONS

Ariel Roguin, et al., Modern Pacemaker and Implantable Cardioverter/Defibrillator Systems Can Be Magnetic Resonance Imaging Safe, Circulation—Journal of the American Heart Association, Aug. 4, 2004 (originally published online Jul. 26, 2004), pp. 475-482, American Heart Association, Dallas, Texas, USA.

(Continued)

*Primary Examiner* — Christopher D Koharski
*Assistant Examiner* — Michael D Abreu
(74) *Attorney, Agent, or Firm* — Michael F. Scalise

(57) ABSTRACT

A hermetic terminal for an active implantable medical device (AIMD), includes an RF distance telemetry pin antenna, a capacitor conductively coupled between the antenna and a ground for the AIMD, and an inductor electrically disposed in parallel with the capacitor and conductively coupled between the antenna and a ground for the AIMD. The capacitor and the inductor form a band pass filter for attenuating electromagnetic signals through the antenna except at a selected frequency band. Values of capacitance and inductance are selected such that the band pass filter is resonant at the selected frequency band. In an alternative form, the band pass filter is coupled in series with the telemetry pin antenna for attenuating MRI signals of a selected frequency band.

11 Claims, 32 Drawing Sheets

Related U.S. Application Data continuation-in-part of application No. 11/557,210, filed on Nov. 7, 2006, now abandoned.

(60) Provisional application No. 60/887,450, filed on Jan. 31, 2007.

(51) Int. Cl.
*A61N 1/37* (2006.01)
*H03H 1/00* (2006.01)
*H03H 7/01* (2006.01)

(56) References Cited

U.S. PATENT DOCUMENTS

| | | | |
|---|---|---|---|
| 4,633,181 A | | 12/1986 | Murphy-Boesch et al. |
| 4,799,499 A | | 1/1989 | Bisping |
| 4,858,623 A | | 8/1989 | Bradshaw et al. |
| 5,209,233 A | * | 5/1993 | Holland et al. ............ 600/412 |
| 5,217,010 A | * | 6/1993 | Tsitlik et al. ............... 607/9 |
| 5,246,438 A | | 9/1993 | Langberg |
| 5,300,108 A | | 4/1994 | Rebell et al. |
| 5,333,095 A | | 7/1994 | Stevenson et al. |
| 5,363,845 A | | 11/1994 | Chowdhury et al. |
| 5,398,683 A | | 3/1995 | Edwards et al. |
| 5,514,173 A | | 5/1996 | Rebell et al. |
| 5,545,201 A | | 8/1996 | Helland et al. |
| 5,629,622 A | | 5/1997 | Scampini |
| 5,697,958 A | | 12/1997 | Paul et al. |
| 5,716,390 A | | 2/1998 | Li |
| 5,722,998 A | | 3/1998 | Prutchi et al. |
| 5,741,321 A | | 4/1998 | Brennen |
| 5,751,539 A | | 5/1998 | Stevenson et al. |
| 5,759,202 A | | 6/1998 | Schroeppel |
| 5,905,627 A | | 5/1999 | Brendel et al. |
| 5,959,829 A | | 9/1999 | Stevenson et al. |
| 5,964,705 A | | 10/1999 | Truwit et al. |
| 5,973,906 A | | 10/1999 | Stevenson et al. |
| 5,978,204 A | | 11/1999 | Stevenson |
| 6,008,980 A | * | 12/1999 | Stevenson et al. ............ 361/302 |
| 6,055,457 A | | 4/2000 | Bonner |
| 6,101,417 A | | 8/2000 | Vogel et al. |
| 6,141,594 A | | 10/2000 | Flynn et al. |
| 6,159,560 A | | 12/2000 | Stevenson et al. |
| 6,275,369 B1 | | 8/2001 | Stevenson et al. |
| 6,280,385 B1 | | 8/2001 | Melzer et al. |
| 6,424,234 B1 | * | 7/2002 | Stevenson ............... 333/182 |
| 6,456,481 B1 | | 9/2002 | Stevenson |
| 6,473,291 B1 | | 10/2002 | Stevenson |
| 6,493,591 B1 | | 12/2002 | Stokes |
| 6,529,103 B1 | | 3/2003 | Brendel et al. |
| 6,535,766 B1 | | 3/2003 | Thompson et al. |
| 6,539,253 B2 | | 3/2003 | Thompson et al. |
| 6,566,978 B2 | | 5/2003 | Stevenson et al. |
| 6,567,259 B2 | | 5/2003 | Stevenson et al. |
| 6,567,703 B1 | | 5/2003 | Thompson et al. |
| 6,606,513 B2 | | 8/2003 | Lardo et al. |
| 6,643,903 B2 | | 11/2003 | Stevenson et al. |
| 6,675,033 B1 | | 1/2004 | Lardo et al. |
| 6,675,779 B2 | | 1/2004 | King et al. |
| 6,687,550 B1 | | 2/2004 | Doan |
| 6,701,176 B1 | | 3/2004 | Halperin et al. |
| 6,765,780 B2 | | 7/2004 | Brendel et al. |
| 6,847,837 B1 | | 1/2005 | Melzer et al. |
| 6,868,288 B2 | | 3/2005 | Thompson |
| 6,876,885 B2 | | 4/2005 | Swoyer et al. |
| 6,882,248 B2 | | 4/2005 | Stevenson et al. |
| 6,898,454 B2 | | 5/2005 | Atalar et al. |
| 6,925,328 B2 | | 8/2005 | Foster et al. |
| 6,931,286 B2 | | 8/2005 | Sigg et al. |
| 6,949,929 B2 | | 9/2005 | Gray et al. |
| 6,952,613 B2 | | 10/2005 | Swoyer et al. |
| 6,971,391 B1 | | 12/2005 | Wang et al. |
| 6,985,347 B2 | | 1/2006 | Stevenson et al. |
| 6,999,818 B2 | | 2/2006 | Stevenson et al. |
| 7,013,180 B2 | | 3/2006 | Villaseca et al. |
| 7,092,766 B1 | | 8/2006 | Salys et al. |
| 7,113,387 B2 | | 9/2006 | Stevenson et al. |
| 7,155,271 B2 | | 12/2006 | Halperin et al. |
| 2003/0028094 A1 | | 2/2003 | Kumar et al. |
| 2003/0050557 A1 | | 3/2003 | Susil et al. |
| 2004/0167392 A1 | | 8/2004 | Halperin et al. |
| 2004/0263173 A1 | | 12/2004 | Gray |
| 2004/0263174 A1 | | 12/2004 | Gray et al. |
| 2005/0197677 A1 | | 9/2005 | Stevenson |
| 2006/0009819 A1 | | 1/2006 | Przybyszewski |
| 2006/0100506 A1 | | 5/2006 | Halperin et al. |

FOREIGN PATENT DOCUMENTS

| | | |
|---|---|---|
| JP | 61181925 | 8/1986 |
| JP | 62233905 | 10/1987 |
| JP | 4071536 | 3/1992 |
| JP | 6054823 | 3/1994 |
| JP | 11239572 | 9/1999 |
| WO | WO 99/19739 | 4/1999 |
| WO | WO 02/083016 A1 | 10/2002 |

OTHER PUBLICATIONS

Robert C. Susil, Christopher J. Yeung, Henry R. Halperin, Albert C. Lardo, Ergin Atalar, Multifunctional Interventional Devices for MRI: A Combined Electrophysiology/MRI Catheter, Magnetic Resonance in Medicine, 2002, pp. 594-600, Wiley-Liss, Inc., Departments of Biomedical Engineering, Radiology & Medicine, Johns Hopkins University School of Medicine, Baltimore, Maryland.

Robert C. Susil, Ergin Atalar, Albert Lardo, Multifunctional Interventional Devices for Use in MRI, U.S. Appl. No. 60/283,725, filed Apr. 13, 2001.

Roger Christoph Luchinger, Safety Aspects of Cardiac Pacemakers in Magnetic Resonance Imaging, a dissertation submitted to the Swiss Federal Institute of Technology Zurich, Zurich, Switzerland, 2002.

C. Gabriel, S. Gabriel and E. Cortout, I. Dielectric Properties of Biological Tissues: Literature Survey.

S. Gabriel, R.W. Lau and C. Gabriel, II. Dielectric Properties of Biological Tissues: Measurements and the Frequency Range 0 Hz to 20 GHz.

S. Gabriel, R.W. Lau and C. Gabriel, III. Dielectric Properties of Biological Tissues: Parametric Models for the Dielectric Spectrum of Tissues.

Constantine A. Balanis, Advanced Engineering Electromagnetics, John Wiley & Sons, Inc., 1989.

* cited by examiner $$F_r = \frac{1}{2\pi\sqrt{LC}} \quad \cdots\cdots (1)$$
$$L = \frac{1}{(2\pi F_r)^2 C} \quad \cdots\cdots (2)$$
$$C = \frac{1}{(2\pi F_r)^2 L} \quad \cdots\cdots (3)$$
FIG. 12
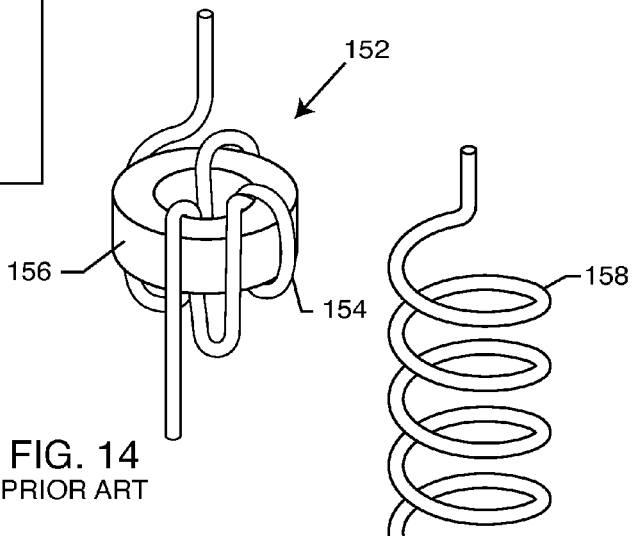
FIG. 14
PRIOR ART
FIG. 15A
PRIOR ART
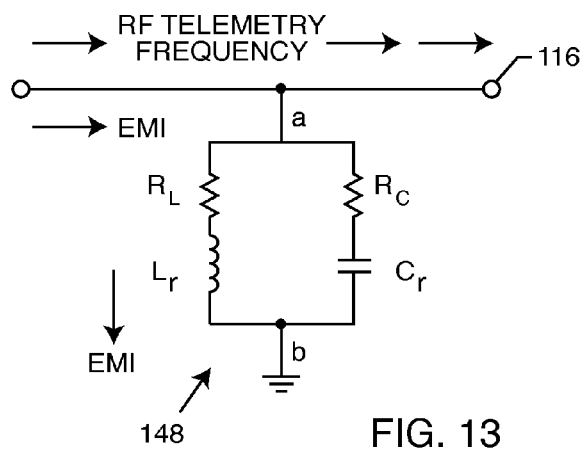
FIG. 13
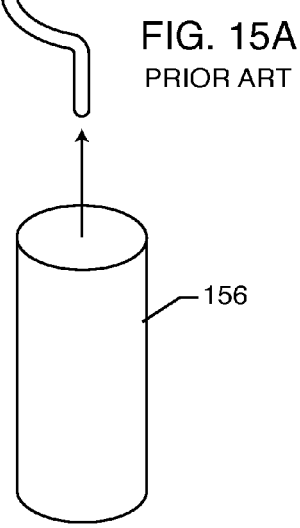
FIG. 15B
PRIOR ART

| FABRICATION METHOD | TYPICAL INDUCTOR MATERIALS |
|---|---|
| LTCC | Ag,Au |
| HTCC | Al,Cu.Al/Cu |
| MMIC | GaAs,InP' |
| MCM-D | Tr,Cu,Aol |
FIG. 65
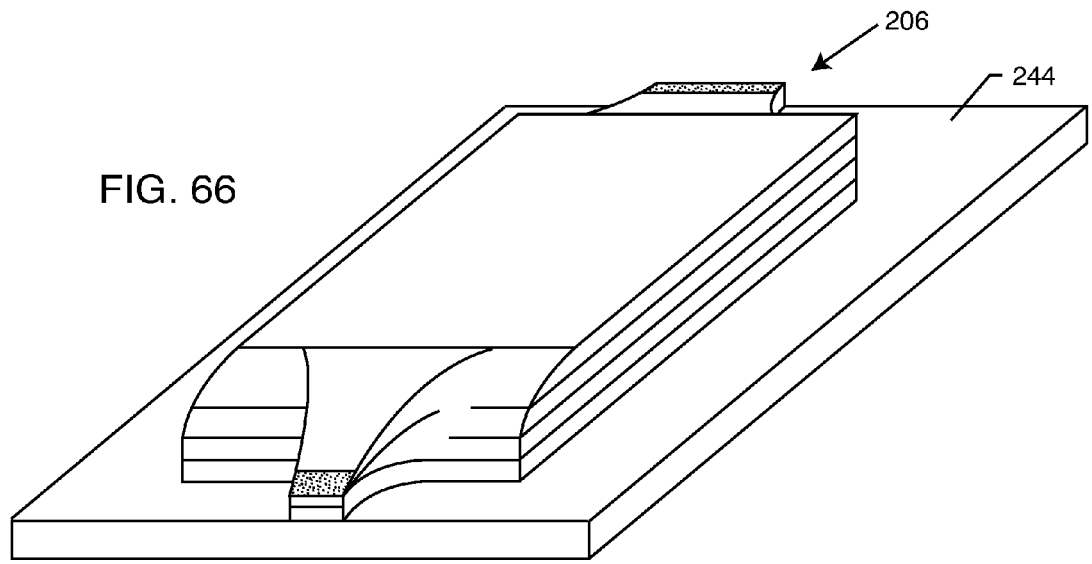
FIG. 66
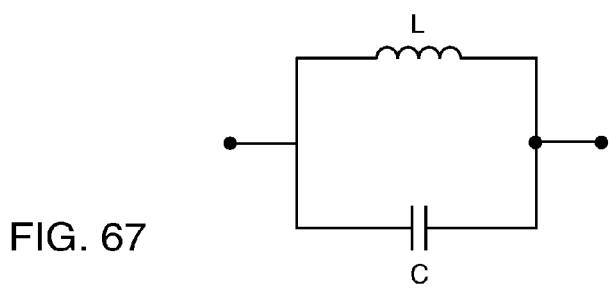
FIG. 67

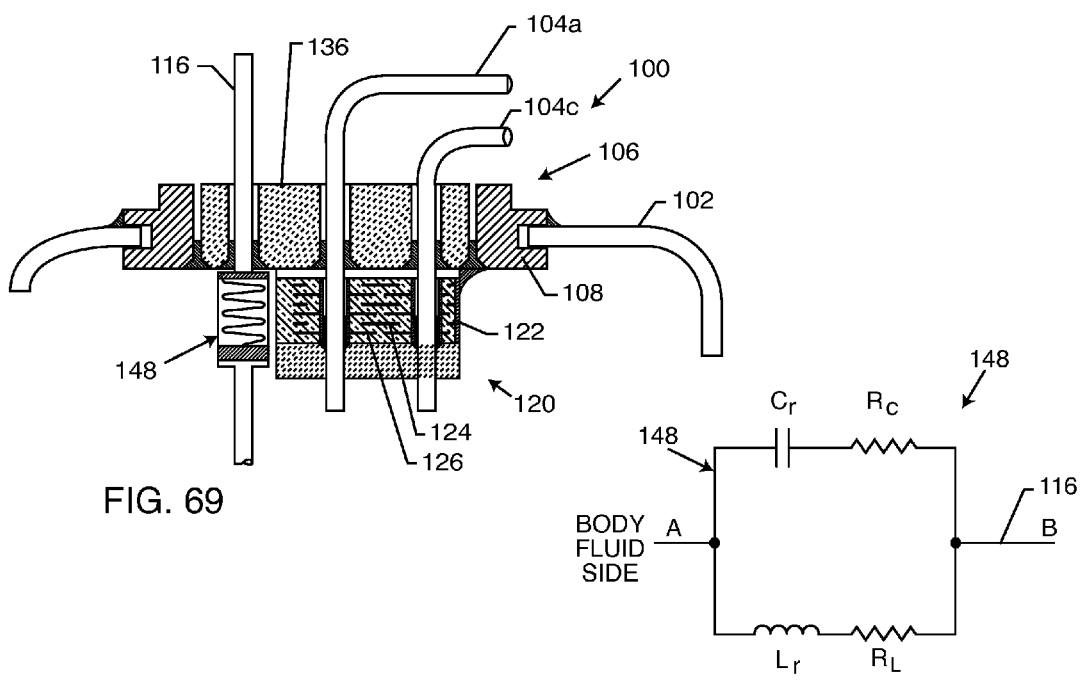
FIG. 69
FIG. 70
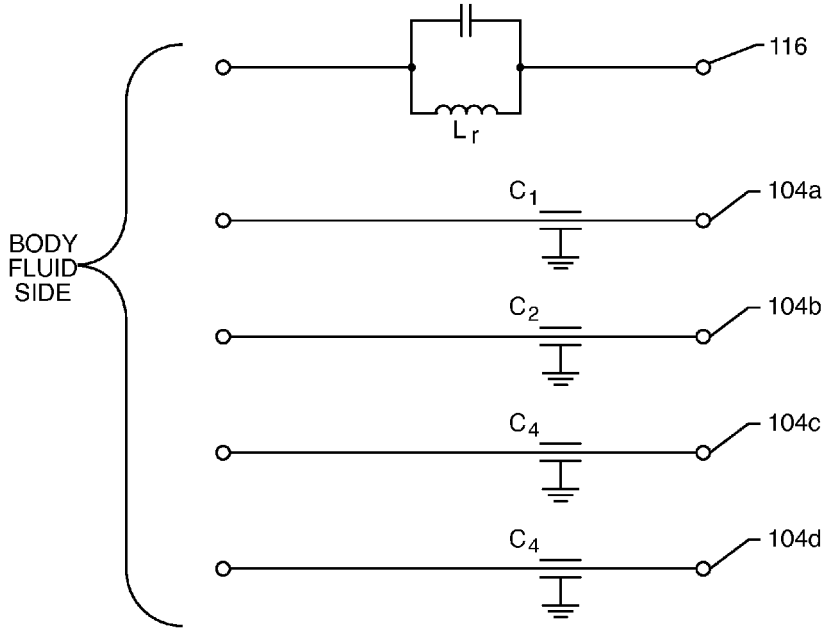
FIG. 71

LOW LOSS BAND PASS FILTER FOR RF DISTANCE TELEMETRY PIN ANTENNAS OF ACTIVE IMPLANTABLE MEDICAL DEVICES

BACKGROUND OF THE INVENTION

This invention relates generally to hermetic terminal assemblies and related methods of construction, particularly of the type used in active implantable medical devices (AIMDs) such as cardiac pacemakers, implantable cardioverter defibrillators (ICDs), biventricular pacemakers, neurostimulators, and the like. More particularly, this invention relates generally to novel EMI tank filter assemblies, particularly of the type used in active medical devices (AMDs) such as cardiac pacemakers, cardioverter defibrillators, neurostimulators, externally worn Holter monitors and the like, which decouple lead wires and/or electronic components of the medical device from undesirable electromagnetic interference (EMI) signals at a selected frequency or frequencies, such as the RF pulsed fields of Magnetic Resonance Imaging (MRI) equipment.

It is well known in the prior art that electromagnetic interference (EMI) feedthrough filter capacitors are typically used in conjunction with hermetic terminal assemblies in an AMD to decouple and shield undesirable electromagnetic interference (EMI) signals from the device. In the past, telemetry used to communicate and reprogram the implantable medical devices was typically at low frequency (generally below 250 kHz). In a typical system, for example in a cardiac pacemaker, a multiple-turn coil (loop antenna) would be embedded inside the titanium housing of the cardiac pacemaker which would be connected to telemetry circuits within the device. Once the cardiac pacemaker was implanted, it was then possible to communicate with said cardiac pacemaker by holding an external wand which contains a loop antenna in close proximity to the implantable medical device. For example, if a physician was to check the battery status, check on a past event or do device reprogramming, the physician would hold the wand over the patient's chest and move it around until it achieved close coupling between the corresponding coil which is implanted within the cardiac pacemaker. This is the typical programming technique that has been used for many years.

As implantable medical device electronics have grown in sophistication and memory storage capabilities, implantable medical devices have become capable of storing a vast variety of past event waveforms. For example, in a cardiac pacemaker application, it is possible for the patient to go into a physician's office two weeks after an "event" and recover cardiac waveforms. In this regard, the patient might have experienced strange feelings in his chest during a basketball game several weeks prior. By recovering stored waveforms, the physician is able to go back to those events and sort out whether it was a simple problem of indigestion or whether there were dangerous cardiac arrhythmias that occurred.

However, this is particularly problematic with the old telemetry frequencies which operated below 250 kHz. Because of the low frequency and the modulation bandwidths associated with such low frequencies, the data transfer rates are very slow. In other words, it is very time consuming to go back and interrogate the device and recover complex stored waveforms with such a low data transfer rate. Accordingly, the modern trend is to go to higher frequency telemetry. A frequency band has been allocated for this (known as the MICS band), which extends from in the 402 to 406 MHz. There are also other frequencies that are allocated or being contemplated above 800 MHz. The advantage of such high frequency telemetry is that the bandwidths associated with such high frequencies are correspondingly very large. This allows for very rapid transmission of the complex cardiac waveform data. Another major advantage of going to high frequency telemetry is that close coupling to the AIMD is no longer necessary.

The new types of telemetry are commonly known in the art as "RF distance telemetry." RF distance telemetry allows the physician to use a radio frequency interrogator to interrogate a patient sitting in a chair across the room while the physician is sitting conveniently at his or her desk. The interrogator and its RF antenna can actually be built right within the implantable medical device programmer, which has the appearance of a laptop computer. In this way, the physician can conveniently and rapidly perform a number of functions which include: check battery status, do device reprogramming, check all device parameters, and more importantly, rapidly recover stored data of past events from the implantable medical device.

In order for RF distance telemetry to work, an external antenna is required to be present outside the titanium housing of the implantable medical device. In the past, the telemetry coil could be embedded completely within the titanium housing. This is because titanium is a non-magnetic material and magnetic coupling to the enclosed loop is easily accomplished. However, an embedded high frequency antenna simply would not work because of the highly effective electromagnetic shield formed by the titanium housing itself. In other words, the titanium housing very effectively reflects and absorbs high frequency electromagnetic energy (electric fields). Accordingly, the RF telemetry antenna must exit through a hermetic terminal of the implantable medical device to provide an external antenna. This is known in the art as the RF telemetry pin. This pin is generally incorporated within the hermetic terminal assembly of the implantable medical device and protrudes into a plastic header block or connector block of, for example, a cardiac pacemaker.

The advent of high frequency distance telemetry, however, poses a serious problem for control of electromagnetic interference. As mentioned, feedthrough terminal pin assemblies are well known in the art for connecting lead wires and electrical signals through the housing or case of an electronic instrument. For example, in AIMDs, such as cardiac pacemakers, the terminal assembly comprises one or more conductive terminal pins or lead wires supported by an insulator structure for feedthrough passage from the exterior to the interior of the medical device. Many different insulator structures and related mounting methods are known in the art for use in medical devices wherein the insulator structure provides a hermetic seal to prevent entry of body fluids into the housing of the medical device. See, for example, U.S. Pat. No. 5,333,095, the contents of which are incorporated herein. The feedthrough terminal pins are typically connected to one or more lead wires which can undesirably act as an antenna and thus tend to collect stray electromagnetic interference (EMI) signals for transmission into the interior of the medical device. The hermetic terminal pin assembly has been combined in various ways with ceramic feedthrough filter capacitors to decouple interference signals to the housing of the medical device.

Typically, a feedthrough capacitor is attached to the ferrule (ground plane) or insulator of the terminal of an active implantable medical device using various attachment methods. It is also well known through various studies that the primary EMI coupling at very high frequencies is into the actual header block wiring of the implantable medical device. In other words, for an implantable cardiac pacemaker, EMI in the cellular telephone frequency range, around 950 MHz, does not generally couple to the entire cardiac lead wire system. Indeed, the primary coupling at this wavelength is directly into the header block wiring. Unfortunately, this also means that this very high frequency EMI can also directly couple to the RF distance telemetry pin antenna.

It is generally not possible to associate the ceramic feedthrough filter capacitor with the distance RF telemetry pin. That is because the feedthrough capacitor is so effective in filtering out high frequency that it would also filter out the high frequency telemetry signal itself. In fact, for battery efficiency reasons, the total loss on the RF distance telemetry pin circuit is limited to 1.0 to 3.0 dB. It is also well known that once undesirable electromagnetic interference enters the inside of the implantable medical device, it can cross couple through capacitive or inductive coupling or antenna action to adjacent circuits. In other words, once the EMI is inside the implantable medical device, it can wreak havoc by coupling to pacemaker sense circuits. Such a scenario presents a serious dilemma for the designers of the AIMDs. That is, it is highly desirable to have a high frequency RF distance telemetry pin, however, the control of EMI is now very problematic.

In addition, compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contraindicated with pacemakers and implantable defibrillators. See also:

(1) "Safety Aspects of Cardiac Pacemakers in Magnetic Resonance Imaging", a dissertation submitted to the Swiss Federal Institute of Technology Zurich presented by Roger Christoph Lüchinger, Zurich 2002;
(2) "1. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, Patent Application Publication US 2003/0050557, Susil and Halperin et. al, published Mar. 13, 2003;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, U.S. Patent Application Ser. No. 60/283,725, filed Apr. 13, 2001.

The contents of the foregoing are all incorporated herein by reference.

However, an extensive review of the literature indicates that MRI is indeed often used with pacemaker, neurostimulator and other active implantable medical device (AIMD) patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted lead wires or devices. For example, for magnetic resonance imaging devices operating at the same magnetic field strength and also at the same SAR level, considerable variations have been found relative to heating of implanted lead wires. It is speculated that SAR level alone is not a good predictor of whether or not an implanted device or its associated lead wire system will overheat.

The effect of an MRI system on the function of pacemakers, implantable cardiac defibrillators (ICDs), neurostimulators, and other implantable medical devices, depends on various factors, including the strength of the static magnetic field, the pulse sequence (gradient and RF field used), the anatomic region being imaged, and many other factors. Further complicating this is the fact that each patient's condition and physiology is different and each manufacturer's pacemaker and ICD designs also are designed and behave differently. Most experts still conclude that MRI for the pacemaker patient should not be considered safe. Paradoxically, this also does not mean that the patient should not receive MRI. The physician must make an evaluation given the pacemaker patient's condition and weigh the potential risks of MRI against the benefits of this powerful diagnostic tool. As MRI technology progresses, including higher field gradient changes over time applied to thinner tissue slices at more rapid imagery, the situation will continue to evolve and become more complex. An example of this paradox is a pacemaker patient who is suspected to have a cancer of the lung. RF ablation treatment of such a tumor may require stereotactic imaging only made possible through real time fine focus MRI. With the patient's life literally at risk, the physician with patient informed consent may make the decision to perform MRI in spite of all of the previously described attendant risks to the pacemaker system.

Accordingly, there is a need for a design methodology which advantageously lends itself to pass the selected high frequency distance telemetry signal while at the same time attenuating nearby adjacent EMI signals, and/or improving the immunity of the medical device to diagnostic procedures such as MRI. The present invention addresses these needs and provides a very simple and low cost solution in the form of a novel resonant tank band stop filter assembly. Preferably, such novel tank filters would be designed to resonate at 64 MHz for use in an MRI system operating at 1.5 Tesla (or 128

MHz for a 3 Tesla system). The present invention thereby fulfills these needs and provides other related advantages.

SUMMARY OF THE INVENTION

The present invention resides in a band pass filter comprising a parallel capacitor and inductor designed to achieve a specified resonance frequency, and can be integrated with a hermetic filtered feedthrough terminal assembly. In one preferred form, the band pass filter is coupled between the RF telemetry pin and ground for attenuating electromagnetic (EMI) signals through the antenna or telemetry pin except at a selected frequency or frequency band. Typically, the existing EMI filtering capacitor is used as the capacitor element of the band pass filter. However, the EMI filter may be used in conjunction with additional capacitor components. Moreover, a distinct capacitor component may be utilized as the capacitive element of the band pass filter. For example, a varactor material may be used as the capacitive component.

When selecting the conductive path, the material forming an inductor component of the circuit should have a desirable inductance and Q factor. Moreover, the material forming the capacitor component should also be of a desirable capacitance and Q factor. The material may form a varactor of sufficient capacitance and tunability.

A substrate tape may be used. For example, an appropriate dielectric substrate tape may be used to produce the capacitive element. Substrate tape may be used with a known magnetic permeability. Appropriate insulative tapes may also be used to produce an embedded filter. The resulting embedded filter may be integrated with existing EMI chip capacitors.

The result is a novel band pass filter utilizing a capacitor and inductor in a parallel circuit, which is in turn connected in one preferred form between the RF telemetry pin and ground for filtering one or more RF telemetry pins. The band pass filter works by effectively blocking all incoming RF frequencies, except for a specific frequency of interest, known as the telemetry or resonance frequency. The resonance frequency and the filtering efficiency are functions of the circuit design and material selection.

The present invention also resides, in accordance with one preferred embodiment, in an EMI feedthrough filtered terminal assembly for AIMDs which generally comprises a feedthrough filtered capacitor having an aperture therethrough and first and second sets of electrode plates, and means for conductively coupling the second set of electrode plates to a ground plane for the active implantable medical device. A terminal pin at least partially extends through the aperture. Means are also provided for conductively coupling the one or more terminal pins to the metallization of the apertures through the feedthrough capacitor thereby making contact between the terminal pins and the first set of electrode plates otherwise known as the active set of electrode plates. In addition, a methodology of placing an inductor in parallel with the capacitance formed by the feedthrough capacitor on the RF distance telemetry pin antenna is provided.

This creates a novel tank circuit which consists of a parallel capacitor and a parallel inductor. It is known in the prior art that when one designs a capacitor in parallel with an inductor, and their component values are selected such that they are resonant at a particular frequency, the resonant combination will tend towards an infinite impedance at the resonant frequency only. This is known as a parallel tank filter in the vernacular of band pass filter engineering. For example, it is possible to use the capacitance value from a feedthrough capacitor with a selected value of parallel inductance such that the parallel combination resonates at the MICS frequency of 402 MHz. Accordingly, the 402 MHz frequency would pass straight through the EMI filtered capacitor with very little to no attenuation. On the other hand, an adjacent EMI frequency, for example, a 950 MHz cellular telephone, would be highly attenuated. That is because at the higher frequency, the parallel combination of the inductor and capacitor are no longer in resonance and therefore a high degree of attenuation would be presented to frequencies outside the band pass notch created by the tank circuit. Tank circuits are very commonly used in the input of radio receivers to sort out the many signals impinging on an antenna at the same time. For example, in a car radio, there are many different frequencies impinging the car radio antenna simultaneously. However, by passing these signals along a number of parallel tank circuits, only the particular frequency of interest is allowed to pass through, be detected and then amplified.

A particular challenge is the packaging of such an inductor element in a volumetric efficient and low cost method such that it becomes practical inside the very small spaces of a cardiac pacemaker. The preferred embodiments presented herein illustrate a number of novel methods to accomplish this.

The mathematics of calculating the resonance of the tank circuit are as follows: the capacitive reactance ($X_c$) for an ideal feedthrough capacitor is given by the following equation: $X_c = +1j/(2\pi f c)$, where f is frequency in Hertz and c is equal to capacitance in Farads; for an inductor the formula for inductive reactance $X_L$ becomes: $X_L = +J \times 2 \times \pi \times f \times L$, where f is equal to the frequency in Hertz and L is equal to the inductance in Henries. It is possible to solve for the resonant frequency by simply setting the two above equations equal to each other. This is a particular frequency at which the capacitive reactance becomes equal and opposite to the inductive reactance. When one sets the two above equations equal to each other and solves from them algebraically, the following equation results: $f_r = 1/(2\pi^2 LC)$. In this way, the designer can go through an iterative process where the designer selects a value of capacitance and then solves for the amount of inductance required for a particular resonance frequency. For example, in an implantable medical device, the value of feedthrough capacitance generally varies from 1000 to 4000 picofarads. Accordingly, it is then quite easy to calculate the amount of inductance that is required to create resonance at the MICS frequency.

Another very important consideration is the "Q" or quality factor of the tank circuit. As mentioned, it is desirable to have a very low loss circuit such that the distance RF telemetry frequency not be undesirably attenuated. The quality factor not only determines the loss of the filter, but also affects the 3 dB bandwidth. If one does a plot of the filter response curve (Bode plot), the 3 dB bandwidth determines how sharply the filter will rise and fall. For example, in a single telemetry frequency device operating at 402 MHz, an ideal filter would be one that had zero dB attenuation at 402 MHz, but had infinite attenuation at say 400 MHz and 404 MHz. Obviously, this is not possible given the space limitations and the realities of the parasitic losses within components. In other words, it is not possible (other than at cryogenic temperatures) to build an inductor that does not have internal resistance and also some stray capacitance. On the other hand, it is not possible to build a perfect feedthrough capacitor either. Feedthrough capacitors have internal resistance known as equivalent series resistance and also have small amounts of inductance. Accordingly, the practical realization of a circuit, to accomplish the purposes of the present invention, is a challenging one. As will be seen in the accompanying drawings, very low loss inductors and capacitors have been designed to realize a very high circuit Q. This is very important to realize the very sharp rise and fall cutoff of the band pass filter of the present invention.

A particular challenge has to do with the tolerances of both the inductive and the capacitive components. For example, in prior art feedthrough capacitor filters, the general capacitance tolerance is +/−20% or in some cases −0+100%. For example, in the case of −0+100%, that would mean that a 1000 picofarad value feedthrough capacitor could go anywhere from 1000 picofarads to 2000 picofarads. However, in the case of a resonant tank filter, if the capacitor was allowed to vary over this wide of a tolerance range, that would undesirably cause great differences in the resonant frequency. Obviously, it would be very undesirable to have some pacemakers that have a resonant notch filter frequency of say 380 MHz, others having a resonant frequency of 402 MHz and others having a resonant frequency of 420 MHz. In this scenario, the only pacemakers that would work efficiently would be the ones that by chance had tank filters that were resonant exactly at the 402 MHz telemetry frequency. The same concepts are true for the inductor. It also must have very tight manufacturing tolerances so that the inductor value itself does not vary too greatly.

It is beyond the scope of the art of most modern manufacturing methods for monolithic high dielectric constant ceramic capacitors to hold an extremely tight tolerance. For example, if one were to hold a +/−0.1% tolerance for a feedthrough capacitor, this would simply not be possible. This is due to the variations in pressing, the variations in firing, the variation in electrode alignments, variations in electrode ink blade, and the like. However, a novel feature of the present invention is the ability to trim such components after manufacturing. It is well known in the art for precision rectangular MLCC capacitors that laser trimming can be accomplished. That is, in an automated setup, the capacitor is placed in a fixture where the capacitance value is continuously monitored. A laser then impinges on the top surface of the capacitor and ablates away or eats away a portion of the electrode(s) until the capacitor falls exactly within the tolerance required. In this way each capacitor is custom trimmed to a precise value. It is also possible to trim the inductors in a like manner. That is, during real time measuring in a computer system of the inductance value, it is possible to use a laser or other trimming method to remove some of the conductor material until the inductor itself reaches a precise value. Ideally, one trims the capacitor after it is placed in parallel with its corresponding inductor to form the tank circuit of the present invention. Then, when utilizing electronic equipment to continuously monitor the resonant frequency, a computer robot performs capacitor and/or inductor laser trimming until the precise resonance frequency is achieved.

Another problem is the inherent aging rate of ceramic dielectric capacitors. For a high dielectric constant material, such as barium titinate with an initial K of around 2500 (initial permeability), the aging rate can be as high as 1.5 to 2% per decade. This means that the capacitor loses capacitance over time at that aging rate. For example, a 1000 picofarad X7R capacitor will lose 2% of its capacitance value between 1000 and 10,000 hours (a decade) of field use. This aging rate must be carefully accounted for in the design of the notch filter. Therefore, it is desirable that the starting value of the capacitor be positioned on one side of the band pass notch frequency so that as the capacitor ages, it will move across the 3 dB bandwidth so that throughout the life of the pacemaker, the high frequency RF telemetry frequency can freely pass with little to no attenuation. It is a feature of the present invention that the combination of capacitor and inductor trimming and aging rates all be integrated into a process thereby providing a novel parallel tank notch filter that can operate over the seven to ten year life of a typical implantable medical device.

In an alternative preferred form of the invention, the band pass or band stop filter is coupled in series with the telemetry pin or antenna for attenuating MRI signals of a selected frequency or frequency band. The band pass filter comprises a capacitor (and its resistance or an added resistance) in parallel with an inductor (and its parasitic resistance), said parallel capacitor and inductor combination being placed in series with the telemetry pin or antenna of the medical device and wherein the values of capacitance and inductance have been selected such that the band stop filter is resonant at a selected frequency (such as the MRI pulsed frequency) or range of frequencies. The inductor Q factor, in the preferred form, is relatively maximized whereas the capacitor Q factor is relatively minimized to reduce the overall Q of the band stop filter, and thereby attenuate current flow through the telemetry pin along a range of selected frequencies or band width. In AIMD or external medical device applications, this range of selected frequencies includes a plurality of MRI pulsed frequencies.

Preferably, the series-coupled band pass filter is disposed adjacent to the hermetically sealed passage of the telemetry pin through the terminal pin assembly mounted on the housing of the medical device. In the most preferred form, the series-coupled band pass filter is mounted along the length of the telemetry pin at an inboard side of the terminal pin assembly.

Other features and advantages of the present invention will become apparent from the following more detailed description, taken in connection with the accompanying drawing which illustrate, by way of example, the principals of the present invention.

BRIEF DESCRIPTION OF THE DRAWINGS

The attached drawings illustrate the invention. In such drawings:

FIG. 12 is a chart showing resonant frequency equations for an inductor with a parallel capacitor;

FIG. 13 is an electrical schematic diagram similar to those shown in FIGS. 10 and 11, illustrating the addition of parasitic resistance (loss) elements;

FIG. 14 is a perspective view of a prior art toroidal inductor;

FIG. 15A is a perspective view of an air-wound coil inductor;

FIG. 15B is a perspective view of a ferrite or iron powdered core which could be inserted into the air-wound coil of FIG. 15A;

FIG. 65 is a table summarizing typical fabrication methods for laying down inductor and capacitor circuit traces;

FIG. 66 is a novel tank chip embodying the present invention similar to FIG. 62, manufactured in accordance with an alternative methodology;

FIG. 67 is an electrical schematic of the structure shown in FIG. 66;

FIG. 69 is an enlarged schematic sectional view similar to FIG. 1, and depicting a further alternative preferred form of the invention wherein the tank or band pass circuit of the present invention is connected in series with the RF telemetry pin;

FIG. 70 is a schematic electrical diagram similar to FIG. 10, but illustrating the tank or band pass circuit of FIG. 69 connected in series with the RF telemetry pin;

FIG. 71 is an enlarged electrical circuit diagram similar to a portion of FIG. 70, and showing the addition of parasitic resistance (loss) elements;

DETAILED DESCRIPTION OF THE PREFERRED EMBODIMENTS

Figure 1:
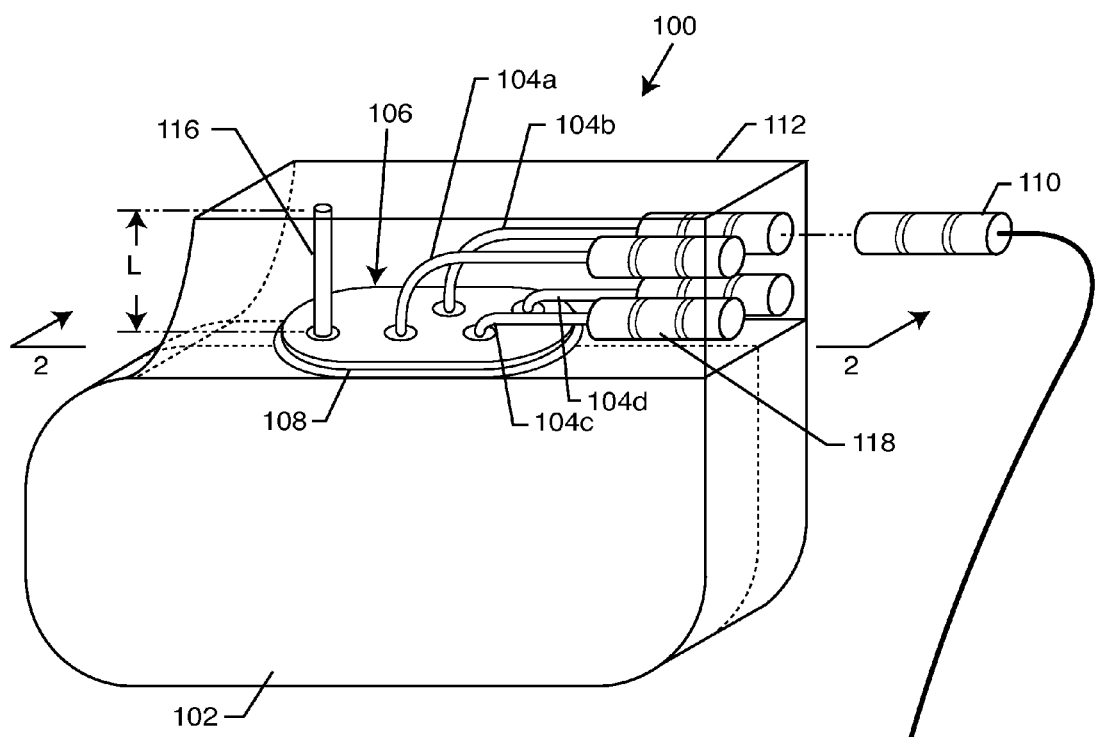
FIG. 1 is a perspective and somewhat schematic view of a prior art active implantable medical device (AIMD) including a lead wire directed to the heart of a patient.
Figure 1:
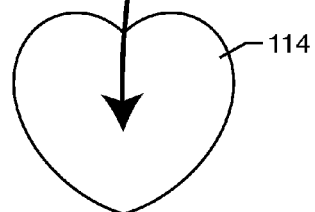

As shown in the accompanying drawings for purposes of illustration, the present invention relates to the design, fabrication, and attachment of a novel band pass filter to or adjacent to a hermetic feedthrough assembly. In one preferred form (FIGS. 10-13, 16-49 and 53-68), the band pass filter is connected between the RF telemetry pin or antenna and ground for filtering EMI separately from the RF telemetry signals. A typical band pass filter used in accordance with the present invention utilizes a capacitor and an inductor in a parallel circuit, which is in turn connected between the RF pin(s) and ground. In another preferred form (FIGS. 69-75), the band pass filter is coupled in series along the length of the RF telemetry pin for attenuating pulsed MRI frequency signals.

Several methods can be employed in the fabrication of the inductive and capacitive components, including discrete components, thin film (i.e., vapor deposition, sol gel), and thick film (i.e., screen printing). Due to progressively smaller and smaller AIMD feedthrough sizes, thin and thick film circuit systems are the most appropriate to achieve the desired final component. Thin and thick film methods can employ a variety of material systems, including LTCC, HTCC, MCM-D and the like, such as that shown below:

| FABRICATION METHOD | TYPICAL INDUCTOR MATERIALS |
|---|---|
| LTTC | Ag, Au |
| HTTC | Al, Cu, Al/Cu |
| MMIC | GaAs, InP' |
| MCM-D | Ti, Cu, Al |

To determine the resonance frequency of the band pass filter, the impedance of the two components must be determined. The impedance for a capacitor and an inductor are expressed using the following equations:

$$X_C = \frac{1}{2\pi fC}$$

$$X_L = 2\pi fL$$

Where f is frequency, C is capacitance, and L is inductance. Resonance occurs when the impedance of the inductor is equal to the impedance of the capacitor, and can be expressed by setting equations (1) and (2) equal to each other as follows:

$$\frac{1}{2\pi fC} = 2\pi fL$$

Solving for $f_o$ results in:

$$f_0 = \frac{1}{2\pi\sqrt{LC}}$$

where $f_o$ is the resonance frequency. At this frequency, the impedance of the circuit is theoretically infinite, and prevents all current flow.

In more traditional inductor components, conductive wire is wrapped about a magnetically active material, such as an iron core or a ferrite material with a high permeability. In thin and thick film inductor deposition, however, the resulting component is usually a two-dimensional spiral made of a highly conductive pathway. Current flowing through the pathway creates a magnetic field. By creating a spiral pathway, two effects are created. Neighboring conductive paths set up mutual magnetism, increasing the magnetic field encircling the array. Also, opposing arrays create an even stronger magnetic field by synergistically increasing the fields through the "core" of the spiral. In this manner, two dimensional inductors are produced. Deposited inductors are analogous to traditional inductors, which are described by the following equation:

$$L = \frac{\mu N^2 A}{l},$$

where μ is a material constant, N is the number of turns, A is the area of the coil, and /is the overall length of the coil. Comparing this to a two-dimensional inductor spiral, it can be seen that by increasing the number of turns with the spiral, the inductance can be increased. This agrees well with the concept of mutual magnetism which results from an array of conductive paths in close proximity, heading in the same direction.

Similarly, increasing the overall diameter of the inductor spiral will increase the measured inductance. Also, printing the spiral on a highly magnetic substrate (i.e., ferrite LTCC tapes) will increase the measured inductance as a function of μ, the material permeability. By changing these variables, it is possible to tailor the inductance for the component.

Thin and thick film capacitors bear more resemblance to their more traditional design, in that a conductive plate is deposited onto a substrate, followed by a layer of dielectric material, and then a top electrode plate. Capacitance is described by following the basic capacitance equation:

$$C = \frac{nk\varepsilon_0 A}{t},$$

where k is the dielectric constant (a material property), A is the cross-sectional area between electrode plates, and t is the thickness of the dielectric, and $\varepsilon_0$ is a material constant. By changing the overlap between electrode plates (effective capacitive area) or the thickness of the deposited dielectric, it is possible to tailor the capacitance generated by the component.

The performance of the circuit is directly related to the efficiency of both the inductor and the capacitor; the less efficient each component is, the more heat loss that results, and this can be expressed by the addition of resistor elements to the ideal circuit diagram. The effect of the heat loss on the equivalent series resistance is to broaden the resonance peak about the resonance frequency. This results in a larger "window" of permitted frequencies, and could result in the passage of undesirable EMI frequencies. Additionally, the heat loss could result in a higher amount of attenuation, or signal loss.

To achieve the most efficient circuit possible, both materials and characteristic geometries must be evaluated for each passive component. Since a deposited inductor pattern is comprised of a closely-packed conductive pathway, the overall conductivity of the wire is evaluated. Since efficiency is related to heat loss, which is in turn related to the real resistance in the component, inductor efficiency can be examined using the equation $$R = \frac{\rho l}{A},$$

where ρ is the resistivity of the material, l is the length of the conductive pathway, and A is the cross sectional area of the conductive pathway. By picking a material with low resistivity (high conductivity), and designing conductive paths with a low length-to-area ratio, it is possible to minimize the loss experienced by the inductor.

In capacitors, the loss is largely related to the inefficiency of the material to effectively store and transfer charge. Whereas a material's ability to store a charge is expressed by the dielectric constant k', the amount of loss in the material during this charge storage is expressed as the dielectric loss factor k". The defining capacitance equation, $$Q=CV,$$

can be expanded and differentiated to solve for current through the component, which results in the following equation:

$$I=i\omega C_0 \varepsilon_0 k'V + i\omega C_0 \varepsilon_0 k''V,$$

where ω is the angular velocity and $\varepsilon_0$ is the permittivity of free space. This equation can be simplified into:

$$I=I_C+I_R,$$

and when plotted, the relationship between the two can be expressed as $$\tan\delta = \frac{|I_R|}{|I_C|} = \frac{k''}{k'}.$$

Tan δ, also known as the dissipation factor, is the direct measure of a capacitor's efficiency. Therefore, the lower this value, the less resistive heat loss experienced by the capacitor.

An additional concern results from the selection of certain capacitor materials, in that they show certain capacitance degradation per decade time. For example, typical X7R capacitor materials experience roughly 2.5% capacitance loss per decade time. For a highly efficient filtering system, this could serve to shift the resonance frequency enough so that the desired RF signal no longer passes through the filter.

One option is to choose a material system that has a deliberately low efficiency. However, as noted previously, this might result in the passing of certain undesirable EMI frequencies, as well as a higher level of attenuation, should the resonance shift with time.

Another available option to alleviate this problem is to use a varactor material, which is a dielectric material whose capacitance can be changed through the application of a DC bias. One such material is barium strontium titanate ($Ba_xSr_{1-x}TiO_3$). Variability of the material is dependent on the value of x, but capacitance changes upwards of 10% have been documented for biases as low as 4 VDC.

In a preferred embodiment, the circuit will be comprised of two distinct passive components, which are fabricated using thick film deposition methods on an LTCC (low temperature co-fired ceramic) material system. This iteration of the design involves the creation of an inductor and capacitor using appropriate ink-based conductive, capacitive, and inductive materials. The resulting ink pattern can be printed on a single layer, or can span several layers. Additionally, the pattern can be left exposed, or can be embedded in a sandwich of appropriate LTCC tapes.

Another version involves the use of "active" LTCC tape layers, in that they directly contribute to the capacitance and/or inductance of those respective components. Substrate tapes with high dielectric constants can be used to increase the net effect of the dielectric inks used to manufacture the capacitor. Furthermore, it is possible to substitute an appropriate dielectric tape in place of the dielectric ink as a method of generating the capacitor element. For the inductor, it is possible to surround the inductor spiral with ferromagnetic LTCC tapes. These tapes help direct the magnetic field lines created by the current traveling through the conductive paths, further augmenting the total inductance of the system.

Another version of this design involves the use of alumina, silicon, or other pre-fired ceramic substrate. In this case, the circuit is deposited to a single substrate layer. The resulting circuit can remain exposed, or can be covered with a passivation layer to prevent atmospheric degradation.

Attachment of the circuit to the feedthrough can be achieved through a number of means, which can be grouped into two major categories. The first of these categories includes a separate attachment procedure, which includes methods such as polyimide curing and metal soldering. The other category involves direct printing of the circuit to either the feedthrough insulator, or the EMI chip itself. In the former case, the circuit would be fabricated in parallel with the feedthrough itself, and attached after both were complete. In the latter, the circuit would be prepared simultaneously either with the insulator or the EMI capacitor. In both cases, the circuit can be embedded in either component, producing a completely sealed, integrated circuit package that can be attached using conventional means.

Referring now to FIG. 1, a prior art active implantable medical device (AIMD) 100 is illustrated. In general, the AIMD 100 could, for example, be a cardiac pacemaker which is enclosed by a titanium housing 102 as indicated. The titanium housing is hermetically sealed, however there is a point where lead wires 104 must ingress and egress the hermetic seal. This is accomplished by providing a hermetic feedthrough or terminal assembly 106. Hermetic terminal assemblies are well known and generally consist of a ferrule 108 which is laser welded to the titanium housing 102 of the AIMD 100. The hermetic terminal assembly 106 with its associated EMI filter is better shown in FIG. 2. Referring once again to FIG. 1, illustrated are quadpolar lead wires consisting of lead wire pair 104a and 104b and lead wire pair 104c and 104d. This is typical of what's known as a dual chamber bipolar cardiac pacemaker.

The IS1 connectors 110 that are designed to plug into the header block 112 are low voltage (pacemaker) connectors covered by an ANSI/AAMI standard IS-1. Higher voltage devices, such as implantable cardioverter defibrillators, are covered by a standard known as the ANSI/AAMI DF-1. There is a new standard under development which will integrate both high voltage and low voltage connectors into a new miniature connector series known as the IS-4 series. These connectors are typically routed in a pacemaker application down into the right ventricle and right atrium of the heart 114. There are also new generation devices that have been introduced to the market that couple lead wires to the outside of the left ventricle. These are known as biventricular devices and are very effective in cardiac resynchronization and treating congestive heart failure (CHF).

Referring once again to FIG. 1, one can see, for example, the bipolar lead wires 104a and 104b that could be routed, for example, into the right ventricle. The bipolar lead wires 104c and 104d could be routed to the right atrium. The primary subject of the present invention, however, relates to the RF telemetry pin 116 which is not connected to the IS-1 or DS-1 connector block. This acts as a short stub antenna for picking up telemetry signals that are transmitted from the outside of the device 100. As previously stated, these frequencies can include several different frequency ranges, including the 402 to 406 MHz MICS band, 500 MHz band or even the 800 MHz band or higher. The advantages of this RF telemetry over the previously close-coupled magnetic coil telemetry are very important. One of the main advantages is that close coupling of two coils is not required. That is, a physician or other medical practitioner can interrogate the AIMD from a great distance away. For example, the patient could be sitting in a chair in front of the doctor's desk while the doctor was able with a laptop computer to interrogate and reprogram the pacemaker. This is another reason why it is common in the vernacular to call this RF telemetry pin the "distance telemetry pin." Another major advantage of the high frequency telemetry is inherent in its broad bandwidth. Low frequency (kHz range) signals are very inefficient at transmitting large amounts of data. Doctors want the ability to rapidly download stored waveforms from AIMD memory. For example, it is possible to go into a doctor's office and recover events that may have happened during a basketball game two weeks ago. However, this takes a high data transmission rate and the ability to download large cardiac waveform files. One can see that the telemetry pin 116 has a defined length L within the header block 112. In general, this length will change depending upon the distance telemetry frequency being used. The pin 116 will tend to be a bit longer for the 402 MHz telemetry and it will get progressively shorter as one goes to higher and higher frequencies (similar to the way cell phones work). However, there are other factors involved, such as the way that it is tuned to the internal circuits within the AIMD 100.

Another major advantage of the RF telemetry pin 116 is that it can be used for continuous operation. In other words, the pacemaker can be interrogated at any time and even provide continuous data streams to remote monitoring locations. It should be obvious that FIG. 1 represents just one of a variety of possibilities. For example, instead of a quadpolar connector with one RF pin, this could be an inline 12-pole system with one or more telemetry pins. In addition, the hermetic terminal assembly 106 could actually be broken into two or even more separate hermetic terminals with a separate RF pin. In other words, all of the diagrams and all of the descriptions herein can be expanded to any number of different configurations.

It should also be obvious to those skilled in the art that all of the descriptions herein are equally applicable to other types of AIMDs. These include implantable cardioverter defibrillators (ICDs), neurostimulators, including deep brain stimulators, spinal cord stimulators, cochlear implants, incontinence stimulators and the like, and drug pumps. The present invention is also applicable to a wide variety of minimally invasive AIMDs. For example, in certain hospital cath lab procedures, one can insert an AIMD for temporary use such as an ICD. Ventricular assist devices also can fall into this type of category. This list is not meant to be limiting, but is only example of the applications of the novel technology currently described herein. The present invention addresses any active implantable medical device that could in the present or in the future incorporate an RF telemetry pin.

Figure 2:
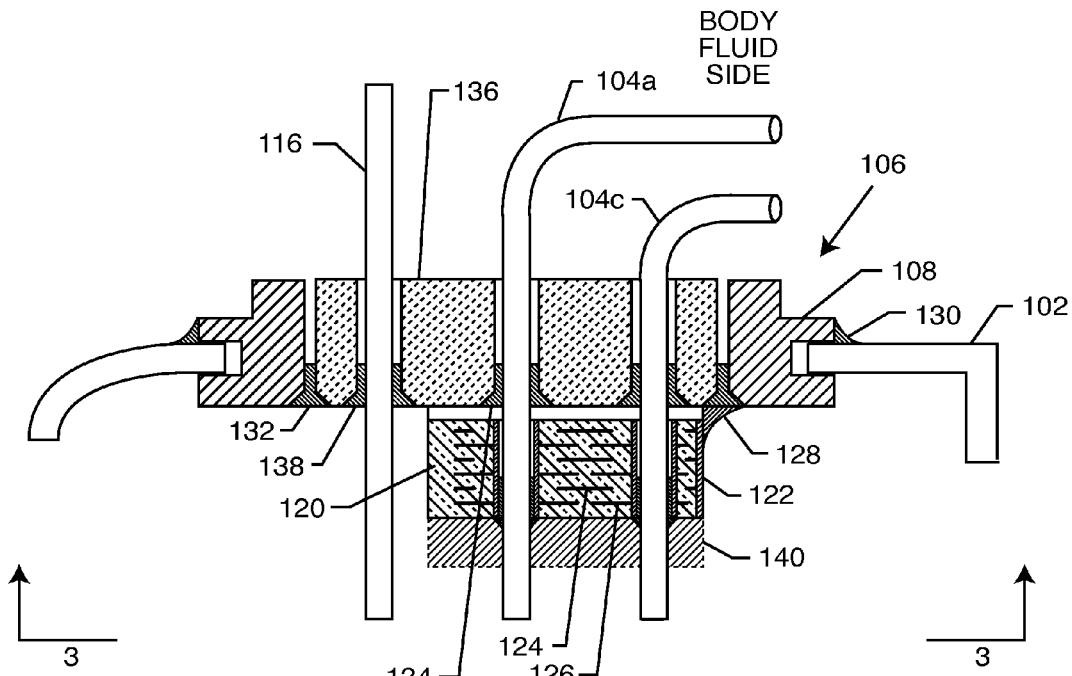
FIG. 2 is an enlarged sectional view taken generally along the line 2-2 of FIG. 1.

FIG. 2 is an enlarged, fragmented cross-sectional view taken generally along line 2-2 of FIG. 1. Here one can see in cross-section the RF telemetry pin 116 and the bipolar lead wires 104a and 104c which would be routed to the cardiac chambers by connecting these lead wires to the internal connectors 118 of the IS-1 header block 112. These connectors are designed to receive a plug 110 which allows the physicians to thread lead wires through the venous system down into the appropriate chambers of the heart (FIG. 1). It will be obvious to those skilled in the art that tunneling of deep brain electrodes or neurostimulators are equivalent.

Referring back to FIG. 2, one can see a feedthrough capacitor 120 which has been bonded to the hermetic terminal assembly 106. These feedthrough capacitors are well known in the art and include U.S. Pat. Nos. 5,333,095, 5,751,539, 5,978,204, 5,905,627, 5,959,829, 5,973,906, 5,978,204, 6,008,980, 6,159,560, 6,275,369, 6,424,234, 6,456,481, 6,473,291, 6,529,103, 6,566,978, 6,567,259, 6,643,903, 6,675,779, 6,765,780 and 6,882,248. In this case, a rectangular quadpolar feedthrough capacitor 120 is illustrated which has external metallization 122. It includes embedded electrode plate sets 124 and 126. Electrode plate set 124 is known as the ground electrode plate set and is terminated at the outside and at the capacitor termination surface 122. These ground electrode plates are electrically and mechanically connected to the ferrule 108 of the hermetic terminal assembly 106 using a thermosetting conductive polyimide or equivalent material 128 (equivalent materials will include solders, brazes, conductive epoxies and the like). In turn, the hermetic seal terminal assembly 106 is designed to have its titanium ferrule 108 laser welded 130 to the overall housing 102 of the AIMD 100. This forms a continuous hermetic seal thereby preventing body fluids from penetrating into and causing damage to the electronics of the AIMD.

It is also essential that the lead wires 104 and insulator 136 be hermetically sealed, such as by the gold brazes 132 and 134. In the case of gold braze 132, this gold braze wets from the titanium ferrule 108 and to the alumina ceramic insulator 136. In turn, ceramic alumina insulator 136 is also gold brazed 134 to each of the lead wires 104. The RF telemetry pin 116 is also gold brazed 138 to the alumina ceramic insulator 136. It will be obvious to those skilled in the art that there are a variety of other ways of making such a hermetic terminal. This would include glass sealing the leads into the ferrule directly without the need for the gold brazes.

As shown in FIG. 2, the RF telemetry pin 116 has not been included in the area of the feedthrough capacitor 120. The reason for this is the feedthrough capacitor 120 is a very broadband single element EMI filter. This is best understood by referring to FIG. 7, which shows the attenuation slope curves for a single element (C filter), a dual element (L filter), a three element (T filter), a four element (LL filter) and even a five element filter. The problem with the RF telemetry pin 116 is that any of these previous prior art filter technologies would greatly attenuate the desirable RF telemetry signal. In other words, if the feedthrough capacitor EMI were to incorporate RF telemetry pin 116, then the RF telemetry would be significantly attenuated and would not work. In fact, for energy efficiency and coupling considerations, it is desirable to have no more than two to three dB of loss on the RF telemetry pin 116 as it comes through the hermetic terminal assembly 106.

FIG. 2 illustrates a single element (C circuit). The ceramic capacitor 120 that is shown can be combined with a number of inductor or inductor slab arrangements (as referenced in U.S. Pat. No. 6,999,818 and in co-pending U.S. patent Ser. No. 11/097,999). An optional filtering component 140 shown co-bonded to the feedthrough capacitor 120 could be an inductor slab, a resistive element, or the like, which would make the single element feedthrough capacitor perform more like a two-element EMI filter.

An obvious disadvantage of the prior art is that undesirable EMI frequencies, such as those produced by cellular telephones, radio frequency identification systems (RFIDs) and other emitters could gain entry into the inside of the housing 102 of the AIMD 100 by introducing signals on to the unfiltered RF telemetry pin 116 and thereby gain entrance into the implantable medical device. It is intended that RF telemetry pin 116 be coupled to internal telemetry circuits within the AIMD. It is important that this be done as quickly as possible because the length of the pin 116 that protrudes inside the AIMD can become an effective re-radiator. In other words, let's assume for example that the telemetry in this case is being done at the MICS frequency of 402 MHz. In this case, the RF telemetry pin 116 would be connected to a circuit which would typically consist of a hybrid chip which would receive the 402 MHz and then demodulate it to be able to utilize its digitally encoded pulse string. It is important that this RF to digital (analog to digital) conversion be done as soon as possible. The reason for this is that digital pulses generally do not contain the high frequency contents that would readily re-radiate to other circuits within the implantable medical device. By example, let's now refer to lead wire 104a. Lead wire 104a, in this case, could be a sensing lead that is implanted into the right ventricle of the heart. In general, biological signals are only of interest in the frequency range from zero to 1 kHz. In other words, signals above 1 kHz are undesirable noise. External EMI emitters, such as cellular telephones, can couple onto the lead wires 104. If these EMI signals were to enter into the inside of the AIMD, they could seriously disrupt the proper functioning of the electronic circuits of the AIMD. Accordingly, EMI filter 120 has been placed to attenuate high frequency signals so that they are decoupled (shorted) to the overall conductive housing 102 of the AIMD. These high frequency EMI signals are then dissipated as a few milliwatts of harmless heat energy. Accordingly, by the time the cardiac sensing pacing signals are coupled to the appropriate circuitry within the AIMD they are relatively free of such undesirable noise. However, referring once again to pin 116, an obvious disadvantage of the prior art is that in addition to the 402 MHz MICS signal, all kinds of other stray EMI can also undesirably enter via pin 116. If this EMI were to parasitically couple to, for example, one of the pacemaker sense circuits, then this could be interpreted either as a normal heart rate (which would cause the pacemaker to shut off or inhibit) or as a dangerous ventricular arrhythmia (which could cause an ICD to inadvertently fire a high voltage discharge).

Figure 3:
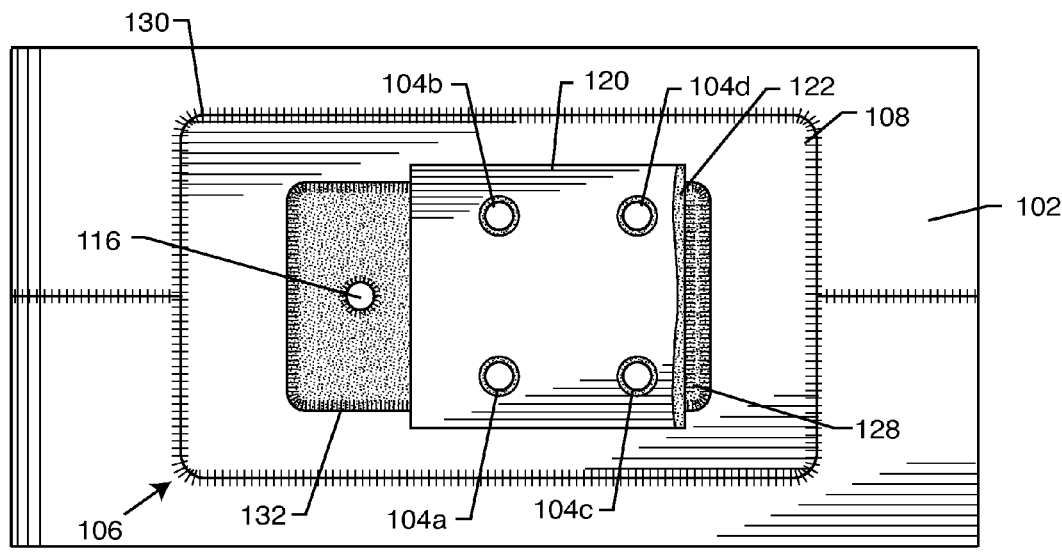
FIG. 3 is a view taken generally along the line 3-3 of FIG. 2.

FIG. 3 is a bottom view taken generally along line 3-3 in FIG. 2. One can see the gold braze 132 which completely seals the hermetic terminal insulator 136 into the overall titanium ferrule 108. One can also see the overlap of the capacitor attachment materials shown as a thermosetting conductive adhesive 128 which makes contact to the gold braze 132 that forms the hermetic terminal 106. This is very important so that the capacitor has an extremely low equivalent series resistance (reference U.S. Pat. Nos. 6,765,779 and 6,765,780).

Figure 4:
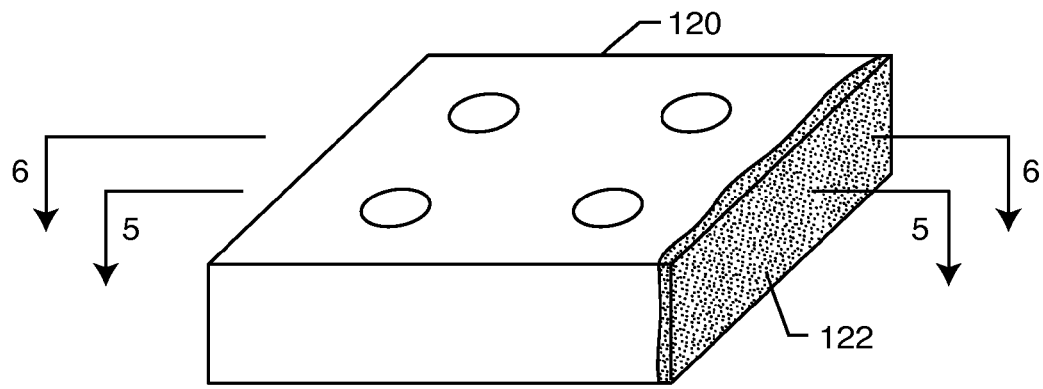
FIG. 4 is a perspective/isometric view of a prior art rectangular quadpolar feedthrough capacitor of the type shown in FIGS. 2 and 3.
Figure 5:
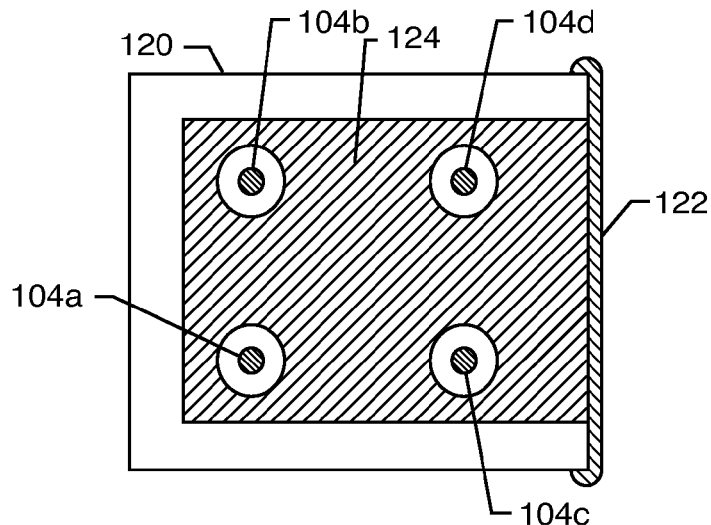
FIG. 5 is a sectional view taken generally along the line 5-5 of FIG. 4.
Figure 6:
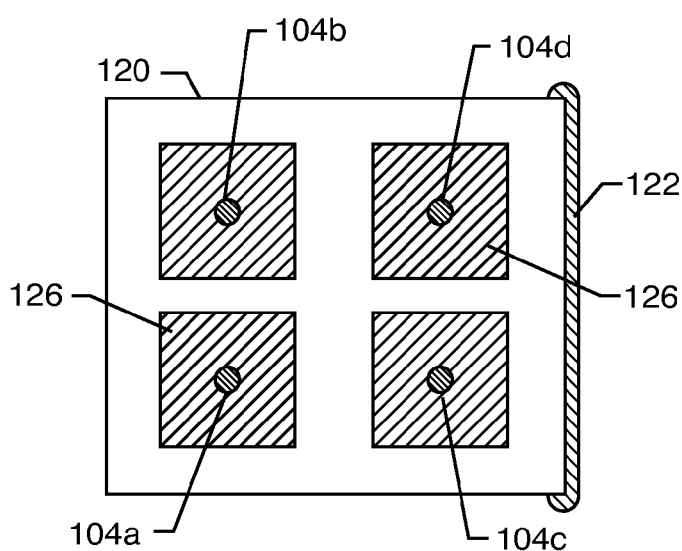
FIG. 6 is a sectional view taken generally along the line 6-6 of FIG. 4.

FIG. 4 is an isometric view of the prior art rectangular feedthrough capacitor 120. As one can see, the termination surface 122 connects to the capacitor's internal ground plate set 124. This is best seen in FIG. 5 where ground plate set 124, which is typically silk-screened onto the ceramic layers, is brought out and exposed to the termination surface 122. The capacitor's active electrode plate set 126 is illustrated in FIG. 6. Referring once again to FIG. 5, one can see that the lead wires 104 are in non-electrical communication with the ground electrode plate set 124. However, referring to FIG. 6, one can see that each one of the lead wires 104 are in electrical contact with the active electrode plate sets 126. The amount of capacitance is determined by the overlap of the active electrode plate area 126 over the ground electrode plate area. One can increase the amount of capacitance by increasing the area of the active electrode plate 126. One can also increase the capacitance by adding additional layers. In this particular application, we are only showing six electrode layers: three ground plates and three active electrode plate sets (FIG. 2). However, 10, 60 or even more than 100 such sets can be placed in parallel thereby greatly increasing the capacitance value. The capacitance value is also related to the dielectric thickness or spacing between the ground electrode set 124 and the active electrode set 126. Reducing the dielectric thickness increases the capacitance significantly while at the same time reducing its voltage rating. This gives the designer many degrees of freedom in selecting the capacitance value.

Figure 7:
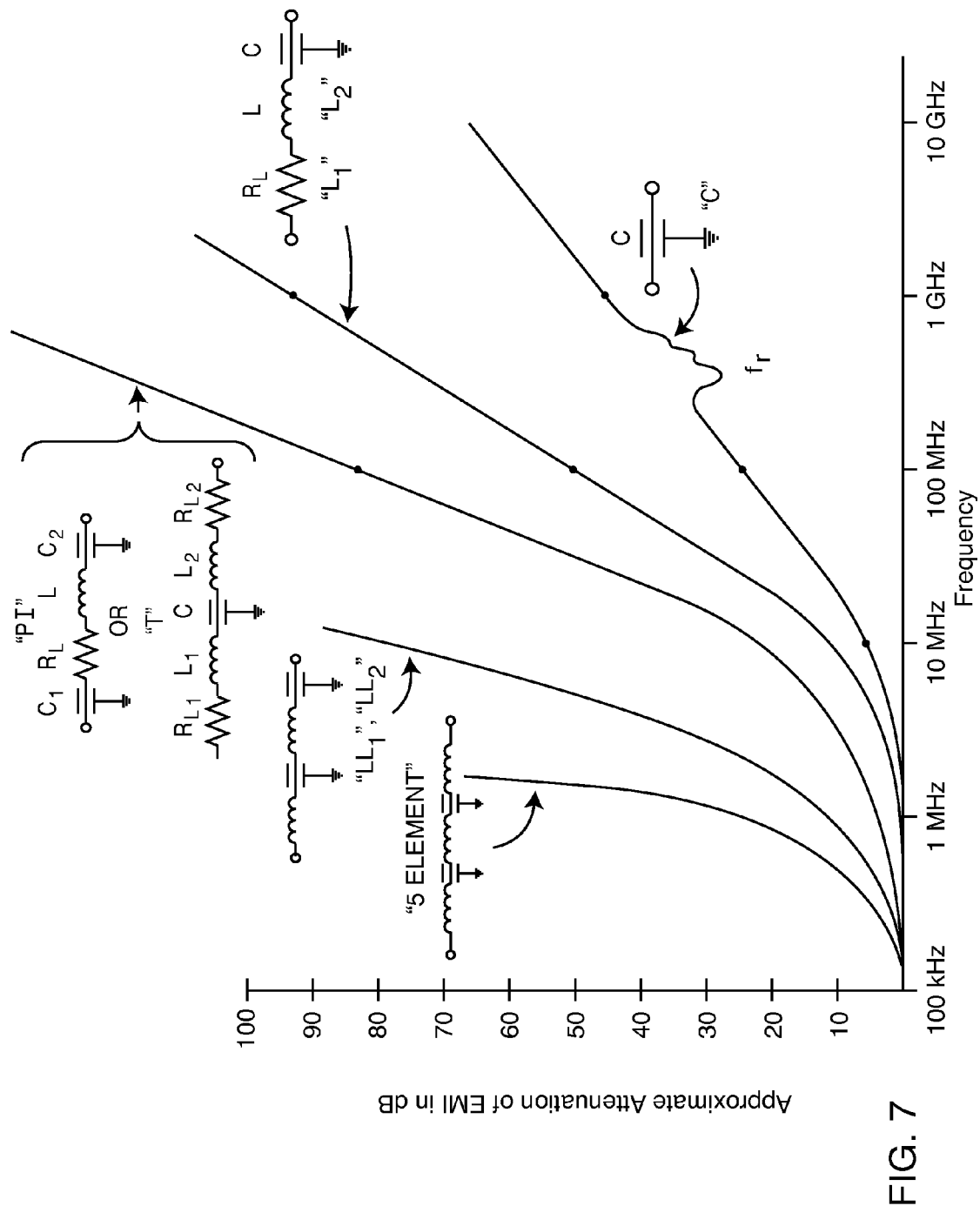
FIG. 7 is a chart illustrating attenuation slope curves for various low pass filter circuits.

FIG. 7 illustrates attenuation slope curves for various low pass filter circuits as previously described in U.S. Pat. No. 6,999,818. Shown are the attenuation slopes for C, L, Pi, T, LL and 5 element EMI filters. As one increases the number of filter elements, the attenuation slope increases. That is, for a given capacitance value, one can achieve a much higher level of EMI attenuation.

Figure 8:
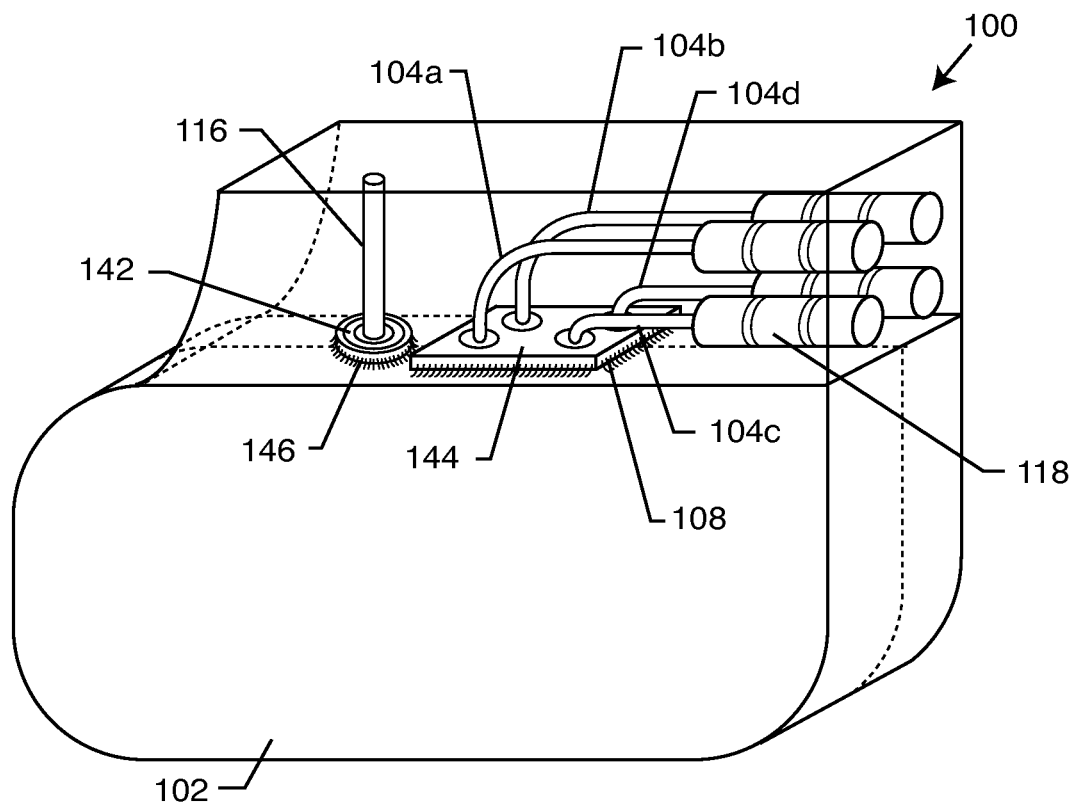
FIG. 8 is a perspective/isometric view of a prior art cardiac pacemaker similar to that shown in FIG. 1, with the exception that an RF telemetry pin extends through its own separate unipolar hermetic terminal assembly.

FIG. 8 is an isometric view of a prior art cardiac pacemaker 100 very similar to that previously described in FIG. 1. However, in this case, the RF telemetry pin or antenna 116 has been separated by its own unipolar hermetic terminal assembly 142 and the quadpolar filtered hermetic terminal 144 has been separated into its own hermetic terminal assembly as shown. One can see that the RF telemetry pin ferrule 146 has been laser welded into the overall metallic housing 102 of the AIMD 100. In addition, the quadpolar filtered terminal ferrule 108 has also been laser welded separately into the overall housing 102 of the implantable medical device 100. For all intents and purposes, the system shown in FIG. 8 works in an equivalent manner to the system previously described in FIG. 1. That is, the RF telemetry pin 116 is unfiltered whereas the cardiac sensing and pacing lead wires 104 are all filtered.

Figure 9:
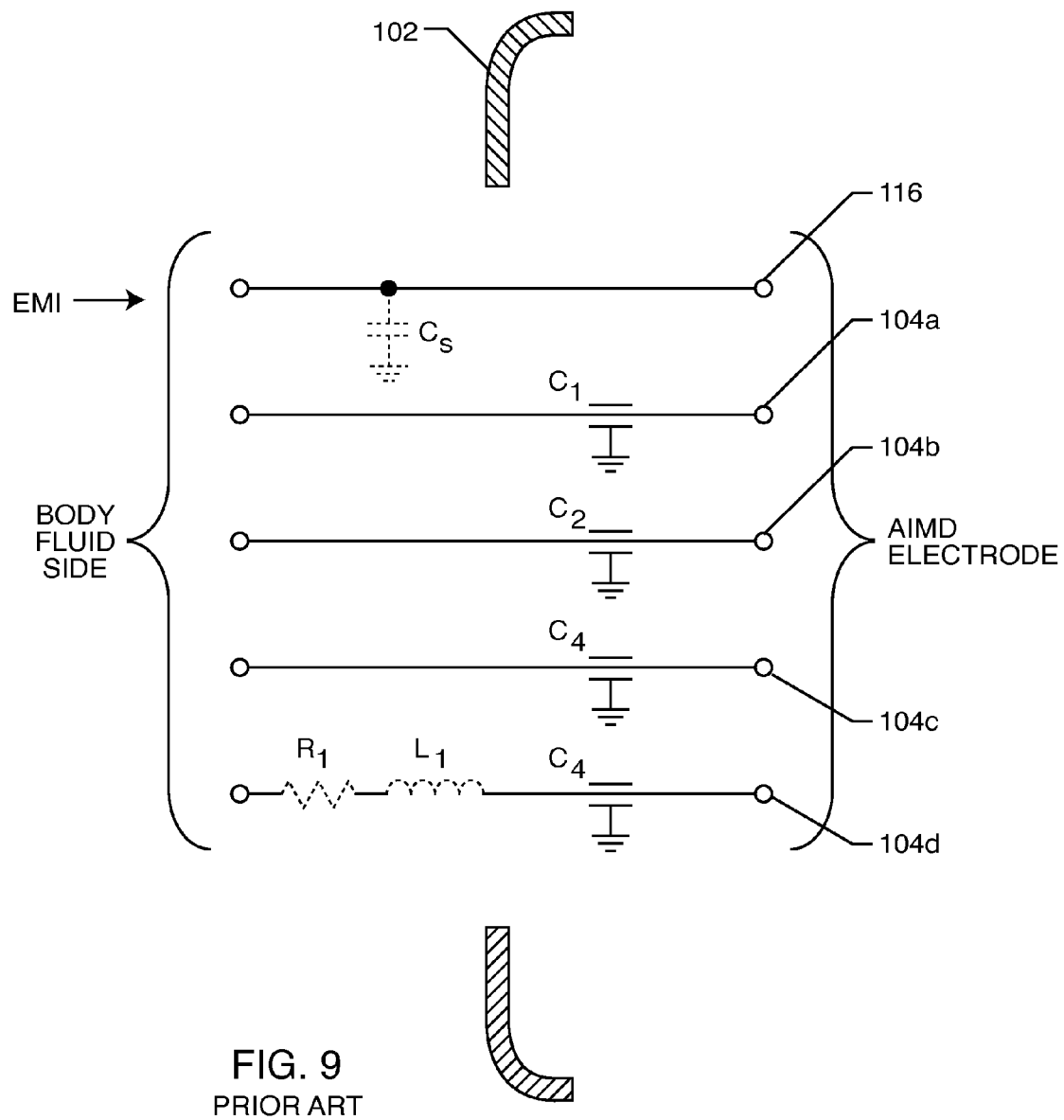
FIG. 9 is a schematic electrical diagram of the prior art quadpolar hermetic terminals plus RF telemetry pins illustrated in FIGS. 1 and 8.

FIG. 9 is a schematic diagram of the prior art quadpolar hermetic terminal plus RF pin as previously illustrated in FIGS. 1 and 8. The RF telemetry pin wire 116 passes through the housing 102 of the AIMD 100 without a filtering element. There is some undesirable stray capacitance that is shown as $C_S$ in the wiring of the RF pin 116. This stray capacitance occurs due to the use of the alumina insulator or glass material 136. The stray capacitance is formed between the conductive ferrule 108 of the hermetic terminal 106 and the RF pin 116 due to the dielectric constant of the insulating material 136. In general, this stray capacitance is undesirable as it can slightly attenuate the high frequency telemetry signal. Accordingly, in the prior art, there have been various things to do to minimize this effect, including minimizing the amount of gold braze area 134 and also increasing the inside diameter of the alumina insulator 136 as it surrounds the RF pin 116. By increasing the air gap or spacing between the alumina insulator 136 and the RF pin 116, one can increase the distance across the dielectric thereby reducing the amount of distributed capacitance $C_S$. However, none of these prior art techniques do anything to prevent EMI from entering the RF telemetry pin 116 and coupling to sensitive electronic circuits.

FIG. 9 also shows that each lead wire 104 $a$-$d$, has a broadband feedthrough capacitor EMI filter $C_1$, $C_2$, $C_3$ and $C_4$. As previously described, this provides a high degree of attenuation to undesirable EMI signals so that they cannot enter into the housing 102 of the AIMD 100 and cross-couple to sensitive electronic circuits. Also shown in FIG. 9 are optional filtering series components $R_1$ and $L_1$ which can increase the EMI filter circuit from a single element device to a two, three or even n element device. This is best understood by referring once again to the curves shown in FIG. 7.

It is very important to note that once EMI enters the inside of the AIMD (trapped in the bottle) it can cross couple or radiate to adjacent circuits. This EMI and its modulation content is very hard to control once it is inside. The predominant EMI filtering philosophy that has been effective for the last ten years is to intercept the EMI at the point of ingress into the metallic housing of the AIMD and then decouple it as harmless heat energy. This eliminates not only the AM, FM, spread spectrum or digital modulation that might be present, but it also eliminates the EMI carrier itself. In other words, the chance for EMI interactions has been eliminated. However, referring back to FIG. 9, having an unfiltered RF telemetry pin 116 works against this philosophy of keeping the EMI outside the housing of the AIMD.

Figure 10:
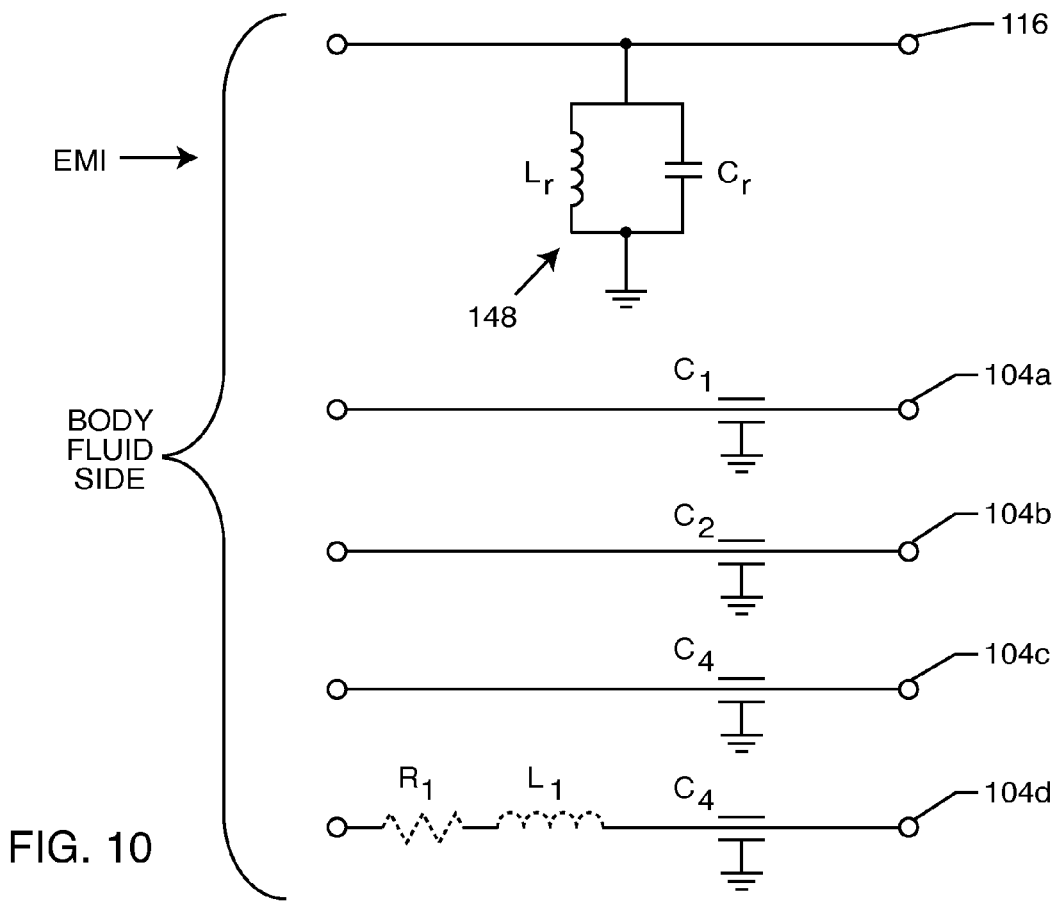
FIG. 10 is a schematic electrical diagram similar to FIG. 9, with the exception that a novel tank or band pass circuit in accordance with the present invention has been added to the RF telemetry pin circuit.

FIG. 10 is the same schematic diagram as previously illustrated in FIG. 9 except that a novel tank circuit 148 of the present invention has been added to the RF telemetry pin 116 circuit. The novel tank circuit consists of a parallel capacitor $C_r$ and a parallel inductor $L_r$ as shown, wherein these two components cooperatively define a band pass or band stop filter. The component values for the capacitor $C_r$ and inductor $L_r$ are carefully selected so that they resonate together at the desired telemetry frequency. For example, in the case of a 402 MHz MICS telemetry frequency, $L_r$ and $C_r$ would be carefully selected so that they were resonant at this one frequency only. When an ideal capacitor and an ideal inductor in parallel are resonant, they are resonant only at one frequency. At this resonant frequency, the parallel combination of the inductor and the capacitor appear as infinite or an open impedance. In other words, for telemetry signals that are conducted along RF telemetry pin 116, there would ideally be no attenuation at the single selected telemetry frequency. On the other hand, for a very high Q L-C tank filter, frequencies that fall outside of the telemetry frequency range would be attenuated. In fact, the tank circuit 148, as shown in FIG. 10 is commonly used in radio receivers of all types to select desired frequencies and reject undesired frequencies. In other words, the present invention resides in a method of producing a L-C tank or band pass filter which achieves a specified resonance frequency and can be integrated with the hermetic filtered feedthrough terminal assembly 106 of an AIMD 100.

In the description of the drawings, in most instances functionally equivalent elements among the various embodiments shown of the prior art and/or embodying the present invention will retain the same reference numbers.

Figure 11:
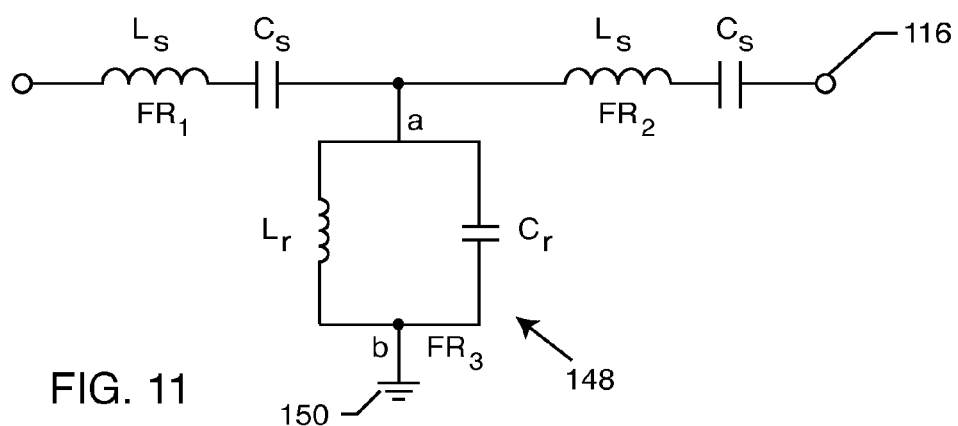
FIG. 11 is an electrical schematic diagram for the RF telemetry pin, illustrating the addition of one or more resonant tanks and series with the telemetry pin wiring.

FIG. 11 is a novel adaptation of the present invention which adds one or more resonant tanks $L_s$ and $C_s$ in series with the telemetry pin wiring 116. These series tanks are also designed to resonate at the telemetry frequency. When these series elements $L_s$ and $C_s$ resonate, their impedance drops to zero which allows only the telemetry signal to pass. At the same time, the novel parallel tank circuit 148 of the present invention consisting of $L_r$ and $C_r$ is shown connected between the telemetry pin circuit 116 and ground 150, as by suitable connection to the ferrule 108 and overall housing 102 of the AIMD (FIG. 2). Each additional filter section increases the attenuation of nearby EMI signals that are just outside the range of the telemetry frequency. Let's assume that the telemetry frequency for this particular AIMD is at 402 MHz. Referring back to FIG. 11, one would select component values for the inductors and capacitors such that they are self-resonant at 402 MHz. This means that the self-resonant frequency FR1, FR2 and FR3 would all be at 402 MHz. Accordingly, a desirable telemetry frequency at 402 MHz would pass through the telemetry pin antenna 116 and wiring with minimal or no attenuation. However, an undesirable EMI frequency that is nearby, for example, at 410 MHz would be heavily attenuated. The more parallel and series sections one adds in accordance with FIG. 11, the more effective the band pass filter will be at rejecting nearby EMI signals.

There are practical limitations due to size, weight and cost that can be achieved. One achieves a very desirable degree of attenuation to most EMI signals by a simple parallel combination of $L_r$ and $C_r$. However, as will be further discussed herein, it is important that these two components be of very high quality factor (Q) in order to achieve a narrow filter bandwith. Examples of such filters in telemetry circuits are described in U.S. Pat. Nos. 6,539,253; 6,868,288; and 6,535,766. The aforementioned patents describe MEMS structures performing discrete circuit notch filters by one or more of: (1) IC fabricating inductors under one or more IC chips; (2) melding IC chips into the well of an RF module substrate and using bonding wires or; (3) surface mounting discreet capacitors over IC chips to reduce space taken up on RF module substrate. An inherent problem in all of these patents is that EMI must be intercepted before it enters down to the chip level of the electronics inside of the AIMD. This is why in the present invention the novel tank filters 148 are incorporated right at the hermetic terminal 106, 142 at the point of entry of the RF pin 116 into the AIMD housing 102. In this way, the EMI signals can be shunted to ground, i.e. the connective housing 102 of the AIMD 100 before they can enter and cross-couple to other sensitive circuits. Referring to U.S. Pat. Nos. 6,539,253; 6,866,288; and 6,535,766; all of the structures and circuits shown first allow the EMI inside the AIMD before band pass or notch filtering is contemplated. In addition, in most embodiments of the aforementioned patents, such filtering is done with active electronics which become nonlinear and thereby ineffective in the presence of very large scale EMI signals.

FIG. 12 (1) is the resonant frequency equation $F_r$ for a parallel inductor with a parallel capacitor. This equation is well known to all electrical engineers, wherein $F_r$ is the resonant frequency and where L is the inductance in henries and C is the capacitance in farads. This obviously becomes an iterative process. If one were to desire a resonant frequency, for example, at 402 MHz, one would then solve the algebraic equation $F_r$ shown in FIG. 12 (1) after assuming a value for L (or C) and then solving for the other variable. There are several practical considerations involved in this. For example, given the state of the art of ceramic capacitors and the size available, this limits one to a specified range of capacitance values that are available. One can then look at a range of inductances that would give you a desired resonant frequency and see if they are realizable within the space allowed. Solving this equation for the inductance L is shown as FIG. 12 (2). In this case, one can assume a value of capacitance C for a given resonant frequency $F_r$ and then solve for the amount of inductance that is required. FIG. 12 (3) shows the equivalent process for solving for the value of required capacitance when an inductance value L is assumed.

It is also important to note that certain EMI emitters are very powerful. For example, when a cell phone or RFID device is held close to a patient's chest, a very high H-field is produced. This is in addition to the normal electric field that such emitters propagate. The H-field can very efficiently couple to the lead wires of an implantable medical device system. Accordingly, the signals that enter into electronics of the AIMD can be extremely high amplitude (both in voltage and in current). Accordingly, active electronic filters are generally overloaded in such cases. When active electronic filters, which consist of a number of p-n junctions, are overloaded, they tend to go nonlinear. In other words, active band pass or frequency selection filters can become their own worst enemy. That is, in the presence of very large scale signals, their dynamic range response becomes nonlinear and they actually start creating their own noise and own spurious responses. Accordingly, the present invention resides in a tank or multi-element telemetry circuit band pass filter constructed of very robust passive components that will be immune to such high power EMI emitters. The problem with active band pass filters has been increasingly acute, as microelectronics chips have become thinner and thinner. For example, it wasn't that many years ago that one could purchase integrated chips with 10-micron technology that worked at relatively high voltages. These older chips tended to have fairly good dynamic range and were somewhat less subject to becoming nonlinear in the presence of large EMI signals. However, today's submicron chips have become extremely sensitive to such effects and work at increasingly lower voltage bias substrate values. In fact, with the change to submicron foundries and in microelectronics, it is not even possible to buy these older technologies anymore. Therefore, cardiac pacemakers, ICDs and other types of AIMDs are increasingly reliant on this new ultra thin wafer technology. Accordingly, there is a need for selective filtering that is very robust and that can only be achieved through passive component elements.

FIG. 13 illustrates the same schematic diagram as previously described in FIGS. 10 and 11 with the addition of parasitic resistance (loss) elements. Referring to FIG. 13, one can see that it is not possible to have an inductance $L_r$ without having some parasitic series resistance $R_L$. In addition, it is not possible to build an ideal capacitor $C_r$ without introducing some series resistance element $R_C$. In the capacitor industry, this is also known as the capacitor's equivalent series resistance (ESR).

It will be obvious to those skilled in passive components that there are other elements to the model for both the inductor and the capacitor. For example, both have parallel resistances due to their insulation resistance properties. However, for modern electronic devices, insulation resistance tends to be many megaohms or even gigaohms. Accordingly, these values are so high that they can be safely ignored for the analysis herein. In addition, the capacitor equivalent series resistance will also consist of a dielectric loss tangent. However, at high frequency, the dielectric losses of the capacitor tend to go away (asymptotically approach zero). Therefore, for high frequency telemetry signals, the capacitor dissipation factor can also be effectively ignored. Capacitors can also have series inductance, which in this case would be highly undesirable. However, it is a property of the capacitor technology that will be further described herein that they are coaxial very low inductance devices. Accordingly, the capacitors equivalent series inductance (ESL) can also be ignored. A similar analogy applies to the series inductive element $L_r$. It is well known to those in the art that are familiar with inductors that undesirable parasitic capacitance can occur from turn to turn. This results in a capacitor in parallel with the $L_r$. However, in this case, since we are trying to build a parallel resonant tank, that capacitance actually is desirable and contributes to the capacitance in $C_r$. Accordingly, that capacitance can be ignored except that it must be counted for in the total capacitance when solving the resonance equation.

FIG. 14 is a prior art toroidal inductor 152 which consists of multiple turns of wire 154 wound around a core 156. Core 156, in the prior art, could be of molly-permalloy, powdered iron, ferrite materials and the like. For the present invention, for active implantable medical devices, the use of such cores is generally not ideal. This is because of the relatively large image artifact that would be created in the presence of magnetic resonance imaging (MRI). An alternative efficient type of inductor is that shown in FIG. 15A. This is an air wound coil 158, which is also well known in the prior art. The problem with this type of coil is that it is not very volumetrically efficient. It also does not lend itself to surface mount or substrate mounting techniques. FIG. 15B is a ferrite or iron powdered core 156 which could be inserted into the air wound coil 158 in FIG. 15A. This forms a prior art solenoid inductor. This greatly increases the volumetric efficiency of the inductor, however, as previously mentioned, some problems associated with MRI image artifact could occur if too much ferrite material was used. The prior art inductor 156, as illustrated in FIGS. 14 and 15B, are examples of the inductor that could be placed in parallel with a capacitor as previously indicated in FIG. 13. Since all of these inductors involve turns of wire, that wire will have an associated resistance $R_L$ as shown in FIG. 13. The capacitor $C_r$ that is shown in parallel with the inductor can be of many prior art construction methods, including monolithic ceramic, glass, porcelain, electrolytic, parallel plates separated by air or other dielectrics and the like. The following drawings will described a number of preferred embodiments which are more readily adaptable for use in an AIMD.

Figure 16:
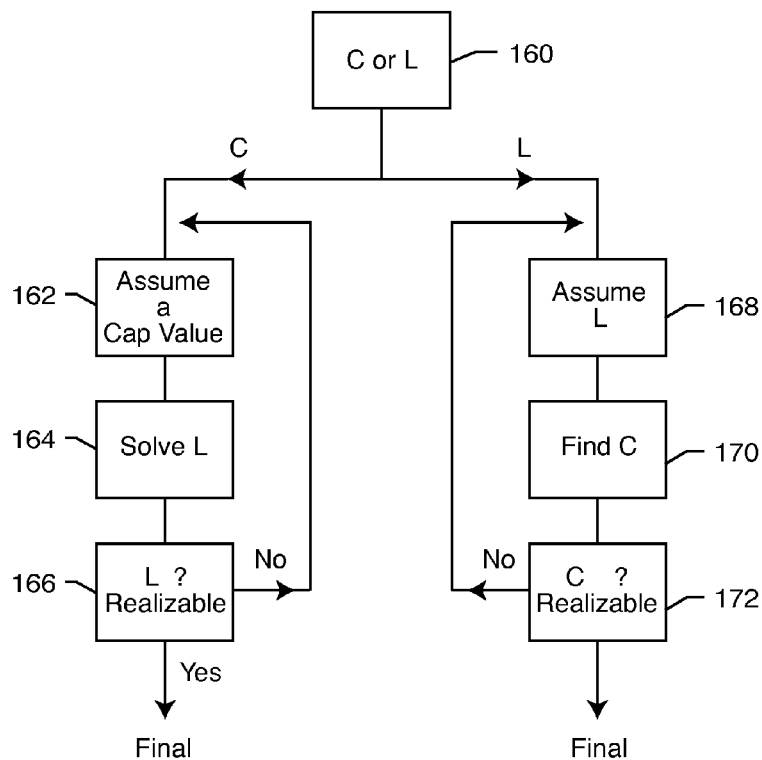
FIG. 16 is a decision tree block diagram illustrating the design process for the band pass filter of the present invention.

FIG. 16 is a decision tree block diagram that better illustrates the design process herein. Block 160 is an initial decision step the designer must make. For most of the designs that are described herein, we will start with a value of capacitance that is convenient. This value of capacitance is generally going to relate to the amount of capacitance used in the prior art EMI filters that, for example, were previously described in FIGS. 1-6. These prior art EMI filters generally range in capacitance value from a few tens of picofarads up to about 4000 picofarads. This puts practical boundaries on the amount of capacitance that can be effectively packaged within the scope of the present invention. However, that is not intended to limit the general principles of the present invention, but just describe a preferred embodiment. Accordingly, in the preferred embodiment, one will select capacitance values generally ranging from 100 picofarads up to about 4000 picofarads and then solve for a corresponding inductance value required to be self-resonant at the selected telemetry frequency. Referring back to FIG. 16, one makes the decision whether the design was C first or L first. If one makes a decision to assume a capacitance value first then one is directed to the left to block 162. In block 162, one does an assessment of the overall packaging requirements of the AIMD hermetic terminal and also examines the capacitance values that are being used for that particular EMI filter application. For example, if the EMI filtered capacitor had four quadpolar capacitors that were already 1000 picofarads, it would be a reasonable assumption to start with 1000 picofarads to keep the design consistent and keep the cost as low as practical. So, in decision block 162, we assume a capacitor value. We then solve block 164, equation 2 from FIG. 12 for the required value of inductance. We then look at a number of inductor designs to see if the inductance value is realizable within the space and other constraints of the design. If the inductance value is realizable, then we go on to block 166 and finalize the design. If the inductance value is not realizable within the physical and practical constraints, then we need to go back to block 162 and assume a new value of capacitance. One may go around this loop a number of times until one finally comes up with a compatible capacitor and an inductor design. In some cases, one will not be able to achieve a final design using this alone. In other words, one may have to use a custom capacitor value in order to achieve a result that meets all of the design criteria. That is, a capacitor and inductor design with low enough internal losses $R_L$ and $R_C$ such that the frequency has high enough Q, that it be small enough in size, that it have sufficient current and high voltage handling capabilities and the like. In other words, one has to consider all of the design criteria in going through this decision tree.

In the case where one has gone through the left hand decision tree consisting of blocks 162, 164 and 166 a number of times and keeps coming up with a no, then one has to assume a realizable value of inductance and go to the right hand decision tree starting at block 168. One then assumes a realizable value of inductance with a low enough equivalent series resistance for the inductor such that it will work and fit into the design space and guidelines. After one assumes that value of inductance, one then goes to decision block 170 and solves the equation 3 in FIG. 12 for the required amount of capacitance. Once one finds the desired amount of capacitance, one then determines whether that custom value of capacitance will fit into the design perimeters. In this case, the capacitance is likely not to end up the same as the capacitance values using the previously aforementioned EMI filter. In this case, a custom capacitor value is used. If the capacitance value that is determined in step 172 is realizable, then one goes on and finalizes the design. However, if it is not realizable, then one can go back up to step 168, assume a different value of L and go through the decision tree again. This is done over and over until one finds combinations of L and C that are practical for the overall design.

For purposes of the present invention, it is possible to use series discrete inductors or parallel discrete capacitors to achieve the same overall result. For example, in the case of the inductor element, it would be possible to use two, three or even more (n) individual inductor elements in series. The same is true for the capacitor element that appears in the parallel tank. By adding or subtracting capacitors in parallel, we are also able to adjust the total capacitance that ends up resonating in parallel with the inductance.

A common problem that is encountered when laying down thick film inductors is that the volumetric efficiency is so high that the inductance value becomes too high for most practical capacitance values in the present RF telemetry pin resonant application. In other words, the paralleling of inductors becomes critical in this case. Accordingly, the present invention also covers using multiple inductors or inductor layers in parallel such that a low enough inductance is achieved to resonate in accordance with FIG. 12 equation 1 at a particular RF telemetry pin frequency. Putting inductors in parallel has an added advantage in that this puts their parasitic resistive elements in parallel which tends to drop the overall resistance $L_r$ of the equivalent inductor. In other words, the Q of the circuit is greatly improved by reducing the resistance.

Figure 17:
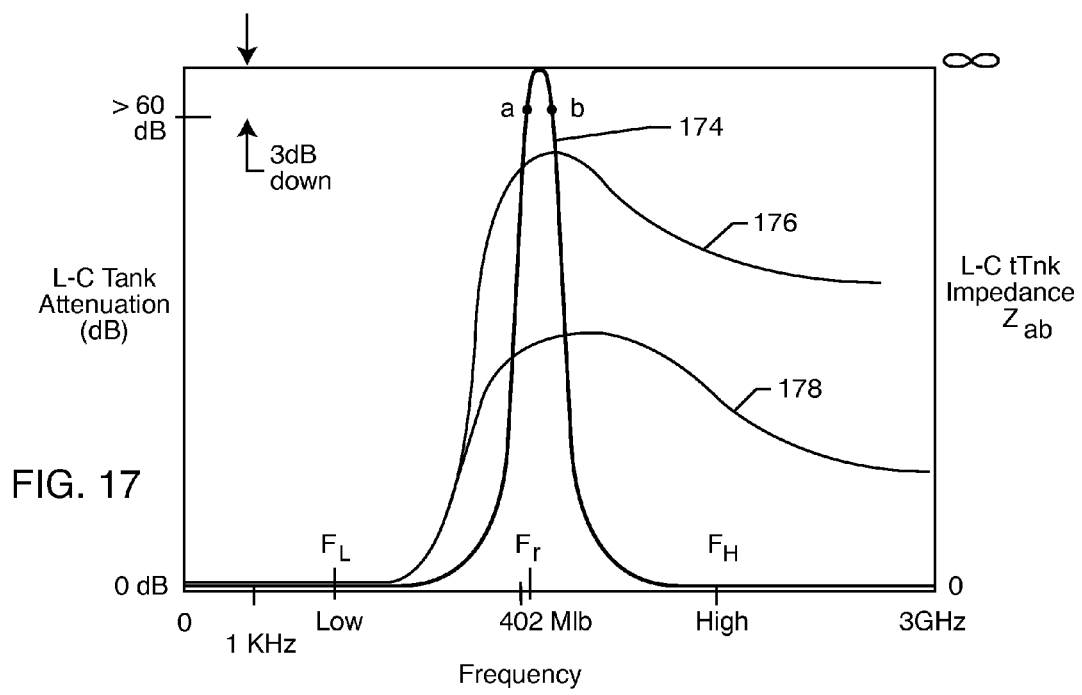
FIG. 17 is a graph illustrating attenuation versus frequency for the parallel tank inductor and capacitor combination shown in FIG. 13.

FIG. 17 describes the attenuation versus frequency for the parallel tank inductor and capacitor combination previously described in FIG. 13. In FIG. 17, the graph is normalized to cover a frequency range from approximately 0 to 3 GHz and the attenuation is normalized to cover attenuation range from zero dB all the way up to infinite dB. Curve 174 is ideal and is representative of the ideal parallel L and C combination previously described in FIG. 10. Of course, such ideal components do not exist so that the curve 174 shown in FIG. 17 is only theoretical and is not practically achievable. One can see that the attenuation to EMI signals that would be coming down RF shielded pin 116 from the body fluid side would be infinite at low frequency. Assuming that, in this case, the resonant frequency $F_R$ as shown is at the 402 MHz frequency, then the parallel combination of L and C would suddenly resonate at this frequency thereby providing very little attenuation (in this ideal case zero dB) to the incident telemetry frequency thereby allowing it to desirably pass through RF pin 116 unattenuated.

The above is a good summary of how the passive parallel L and C tank filter 148, which will be hereinafter referred to as the resonant tank, operates. Simply, it allows only one desirable frequency to pass, which is the RF telemetry pin frequency, and offers a higher degree of rejection to all other signals which are considered to be electromagnetic interference noise. Referring back to FIG. 17, one can see two points a and b that are noted 3 dB down. In band pass filter terminology, this is the frequency spread at the 3 dB down points of the band pass filter circuit. This directly relates to the quality factor (Q) of the circuit components. Overlaid on the curve 174 of FIG. 17 is a curve 176 showing the use of relatively lower Q components. By lower Q, we mean an inductor with higher degree of series resistance and/or a capacitor with a higher degree of internal resistance. Curve 176 illustrates the response curve of such a filter. It will still tend to be generally resonant at the 402 MHz point, however, the 3 dB bandwidth is now exceedingly large. This means that it would allow it to pass a substantial amount of high frequency EMI in addition to the desired telemetry frequency. Worse yet, there would also be considerable loss that creeps in at the telemetry frequency itself. In other words, the 402 MHz would also be undesirably attenuated to some degree. Curve 178 illustrates the use of very low Q components. Accordingly, the use of relatively high Q components is required so that EMI outside the 402 MHz frequency range is properly attenuated and that too much loss does not occur at the selected telemetry frequency ($f_r$).

All of these factors need to be taken into account in the decision matrix illustrated in FIG. 16.

The designer also faces another kind of a tradeoff that has to do with the practical aging rate of the components utilized. That is, referring back to FIG. 10, one can see that for the parallel tank 148 there is both an inductor and a capacitor. For example, if the capacitor element was manufactured from high dielectric constant monolithic ceramic capacitor material (ceramic), then the capacitor dielectric constant will age (lose capacitance) over time. For example, if X7R barium titinate was to be used, which is generally the same material that is used for the EMI feedthrough capacitor, it could be expected that the capacitance would age at approximately 2% per decade. Capacitor aging is typically expressed in percent per decade. For example, let's assume a capacitor dielectric that is aging at 2% per decade and starts out with a value at 1000 hours of 1000 picofarads, the next decade would be 10 times or 10,000 hours. This means that the 1000 picofarad capacitor would lose 2% of its capacitance over this decade. There are 8760 hours in one year, so 10,000 hours is approximately 1 year of service in the field. For active implantable medical devices such as cardiac pacemakers, they are generally limited by their battery life which generally runs from 5 to 7 years. It is a safe assumption, however, to use 10 years as design life with a suitable safety factor. Accordingly, we will use 100,000 hours as an end point guideline which would mean that the subject capacitor has reduced in capacitance from initial value of 1000 picofarads by 2% and then a second 2% (approximately 4%). In other words, the capacitor, at the end of its expected life in the field, would drop by 40 picofarads, which is 960 picofarads. What this means is that the designer must choose a very careful balancing act to make sure that the tank filter 3 dB points, as previously described in FIG. 17, are wide enough so that the tank circuit stays close to resonance as its component values age. This is also true for the inductance. This makes for a relatively complex design problem as the designer will choose to start at one side of the resonance curve, as shown in FIG. 17, and make sure that he stays within it as the component values age. It is well known to electrical engineers how to define the quality factor or Q for both individual inductor and capacitor elements. For example, in a ceramic capacitor, the quality factor is simply 1 divided by the dissipation factor. However, what really determines the shape of the curves shown in FIG. 17 is the overall Q of the resonant circuit consisting of the parallel inductor and capacitor combination.

When characterizing impedance behavior in inductors, both an imaginary and a real component are measured. The imaginary impedance is frequency-dependent, and is directly related to the component's inductance. The real component is independent of frequency, and is a measure of the component's loss, usually resulting in some amount of heat dissipation and a temperature rise.

The efficiency of an inductor is expressed by the equation $$Q = \frac{j\omega L}{R}$$

Where Q is the quality factor, $j\omega L$ is the frequency-dependent impedance, and R is the real Ohmic (resistance) of the component. Higher Q values represent increasingly more efficient inductor components. It should be noted that the Q factor in this case is the inverse of the related dissipation factor typically used to express capacitor efficiency.

Examining the above equation, one can see that component performance can be increased by minimizing the real resistance, increasing the inductance, or both. Resistance can be minimized by choosing highly conductive materials for the inductor spiral designs, while simultaneously designing large cross-sectional pathways. Inductance can be maximized by optimizing the geometry of the spiral design, and by increasing the permeability of the surrounding material. In spiral inductor designs, permeability is assumed to be 1, although this can be increased significantly by embedding the inductor spiral in ferromagnetic materials.

Efficiency of a tank circuit is also measured in terms of a quality factor, Q, although this factor is defined differently than the one previously explained. The circuit Q is typically expressed using the following equation:

$$Q = \frac{f_r}{\Delta f_{3\,dB}}$$

Where $f_r$ is the resonance frequency, and $\Delta f_{3\,dB}$ is the bandwidth of the tank filter. Bandwidth is typically taken as the difference between the two measured frequencies, $f_1$ and $f_2$, at the 3 dB loss points as measured on an insertion loss chart, and the resonance frequency is the average between $f_1$ and $f_2$. As can be seen in this relationship, higher Q values can be obtained by developing a circuit with a narrow bandwidth in relation to the resonance frequency.

Material and application parameters must be taken into consideration when designing notch filters. Most dielectric materials age 1-5% in capacitance values per decade of time elapsed, which can result in a shift of the resonance frequency of upwards of 2.5%. In a high-Q filter, this could result in a significant and detrimental drop both in the strength of the telemetry signal and in filtering performance. A low-Q filter would minimize the effects of resonance shift and would allow a wider frequency band through the filter. However, low Q filters also display lower than desirable attenuation behavior at the desired frequency (see FIG. 17, curve 178). For this reason, the optimum Q for the circuit will be application specific.

Figure 18:
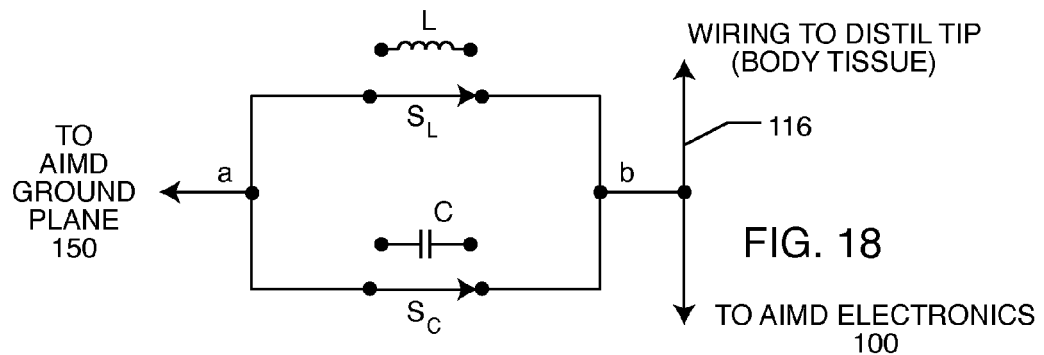
FIG. 18 is an electrical schematic diagram illustrating the pathway of EMI signals picked up by the RF telemetry pin as they travel from a distal tip toward the AIMD in the absence of other considerations.

FIGS. 18-21 are best understood by referring to the schematic diagram of the novel band pass filter (tank) 148 of the present invention shown in FIG. 13. As one can see, the tank 148 consists primarily of a parallel inductor L and a parallel capacitor C. FIG. 18 illustrates the pathway of EMI signals picked up by the RF telemetry pin 116 as they travel from a distal tip toward the AIMD 100. In the absence of other considerations, the tank filter 148 typically shunts the EMI signals to the AIMD ground plane 150.

Figure 19:
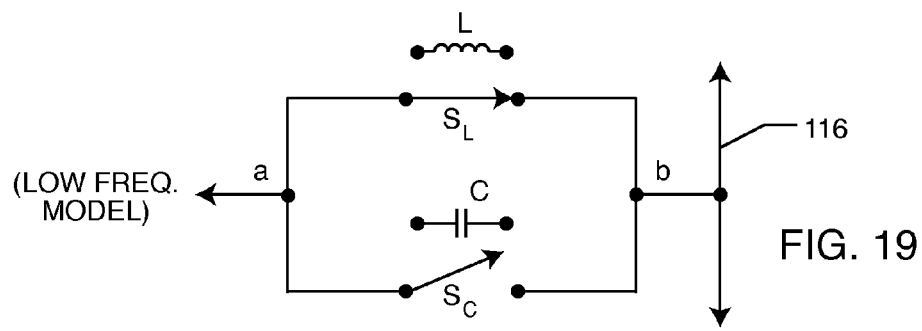
FIG. 19 is an electrical schematic diagram similar to FIG. 18, illustrating a low frequency model of the tank circuit of the present invention.

FIG. 19 illustrates a low frequency model of the tank circuit 148 of FIG. 13, 18. At this point the switch $S_L$ is closed. This means that low frequency signals (EMI noise) which come into the telemetry pin 116 would be shunted to ground 150 before they can enter into the housing of the AIMD. This is due to the presence of the inductor element L. At very low frequencies, inductor elements tend to look like short circuits. At the same time, capacitive elements tend to look like open circuits at low frequency or dc. This is illustrated by the switch $S_C$ being open. Accordingly, the circuit model shown in FIG. 19 simply consists of a shorted inductor L.

Figure 20:
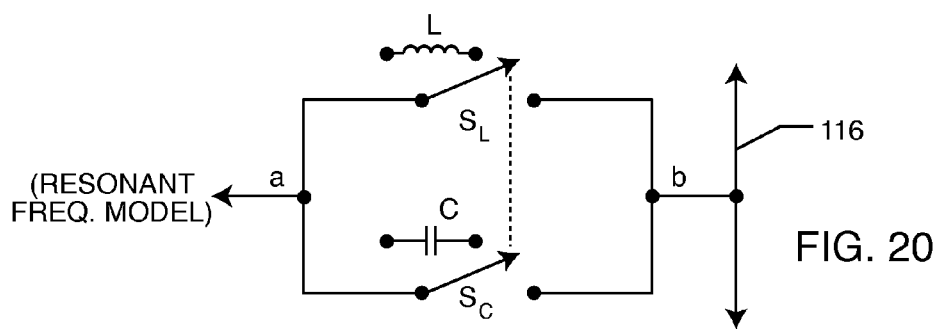
FIG. 20 is an electrical schematic similar to FIGS. 18 and 19, illustrating the resonant frequency model of the tank circuit of the present invention.

FIG. 20 illustrates the resonant frequency model for the tank circuit of FIG. 13. FIG. 13 assumes a very high Q device wherein both the resistive loss of the inductor $R_L$ and the resistive loss (ESR) of the capacitor C are very low. In other words, very high Q components have been used such that the losses are minimized and can be ignored. In FIG. 20 one can see that, at resonance, the impedance of the tank circuit 148 measured between points a and b looks like an open switch. This allows the telemetry frequency to pass by the tank filter 148 without attenuation.

Figure 21:
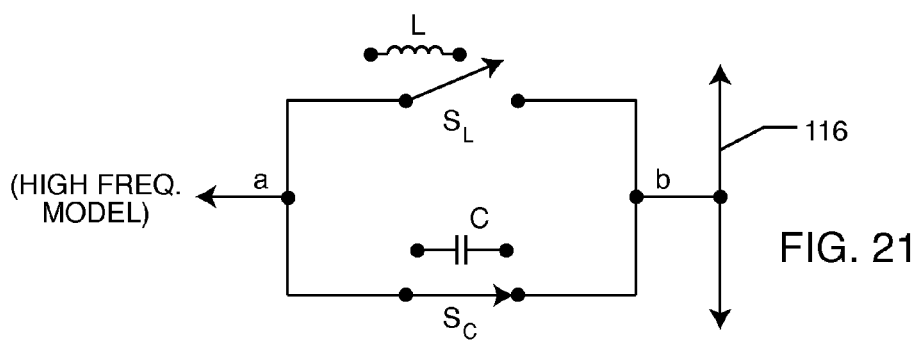
FIG. 21 is an electrical schematic similar to FIGS. 18-20, illustrating the high frequency model of the resonant tank of the present invention.

FIG. 21 illustrates the high frequency model for the resonant tank 148 of FIG. 13. In this case, the inductor appears as an infinite impedance (open) at switch $S_L$. However, at very high frequencies, ideal capacitors C tend to look like short circuits. The switch $S_C$ is closed at high frequencies which tend to shunt high frequency EMI noise to ground 150. However, this will work only if the capacitor C design is a very efficient coaxial technology. For example, coaxial technology is well known in the art as feedthrough capacitors. A novel feature of the present invention is to incorporate coaxial capacitor technology along with spiral wound inductor technology such that both low frequency and high frequency shorting (attenuation) of the novel tank occurs. In lesser preferred embodiments using, for example, prior art MLCC rectangular chip capacitors, the characteristics shown in FIG. 21 would not be completely achieved. That is, the switch $S_C$ would not completely shut at high frequency due to the parasitic inductive losses within such prior art MLCC capacitors. However, for feedthrough capacitor technology, which is typically used as high frequency EMI filters, the model shown in FIG. 21 approaches ideal behavior and is effectively realized.

It should also be pointed out that geometry is very important. Feedthrough capacitor technology is well known in the art. The simple act of converting a rectangular MLCC chip, which is a two terminal device, to a three terminal device by making it have a hole feature changes it to a high frequency broadband coaxial transmission line. One aspect of the present invention resides in a composite MLCC capacitor-inductor tank filter. Its purpose is to allow high frequency telemetry to freely pass. However, another important purpose is that it must attenuate high frequency EMI. Accordingly, it must have good high frequency characteristics in order to properly attenuate, for example, a 1.8 MHz cellphone frequency. Two terminal technology will work to a degree but is not the preferred embodiment. Accordingly, in preferred embodiments, the present invention describes a number of ways of incorporating feedthrough capacitor technology along with spiral or meander inductor technology such that high frequency performance will be achieved.

Figure 22:
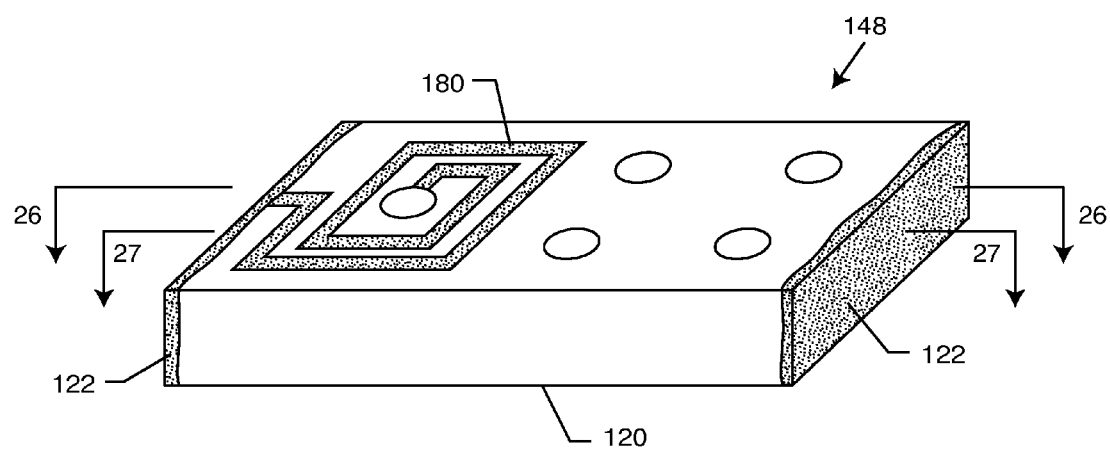
FIG. 22 is a perspective view of a modified feedthrough capacitor such as that illustrated previously in FIGS. 2-6.
Figure 23:
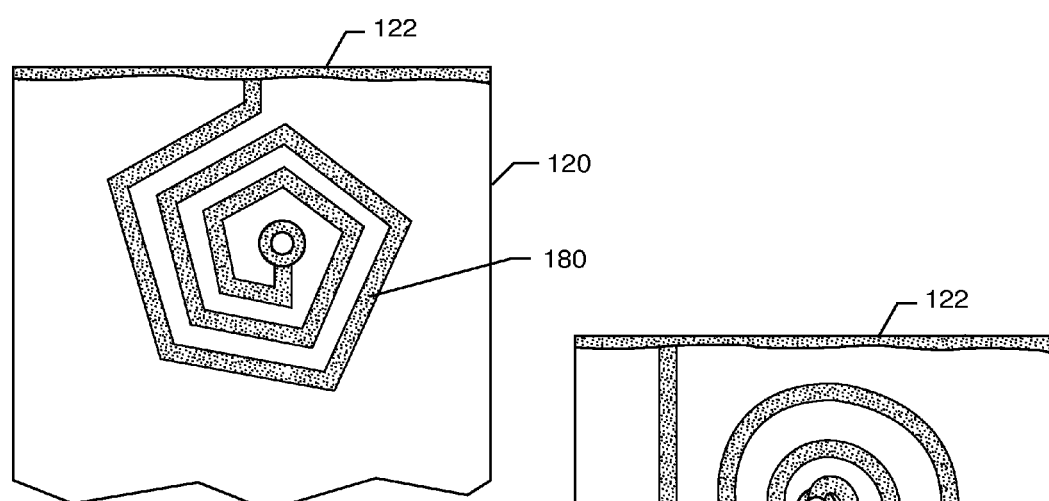
FIG. 23 illustrates an alternative printing of an inductor on the surface of the capacitor of FIG. 22.
Figure 24:
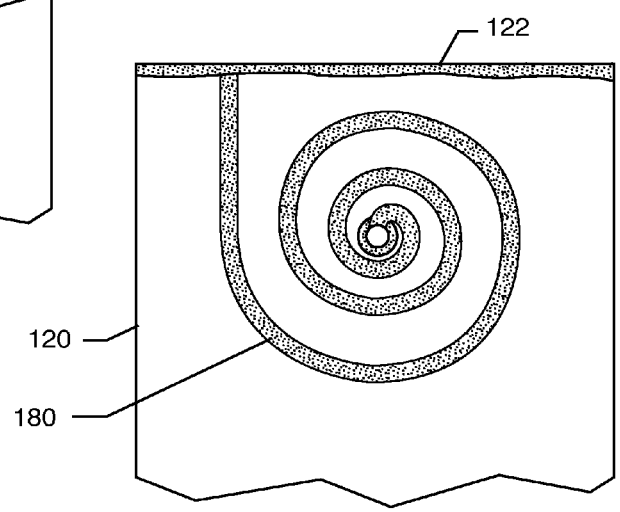
FIG. 24 shows another alternative type of printing for the inductor on the surface of the capacitor of FIG. 22.

FIG. 22 illustrates a modification of the feedthrough capacitor 120 that was previously illustrated in FIGS. 2-6. In this case, the feedthrough capacitor 120 has been elongated to overlap and attach to the RF telemetry pin 116. An inductor 180 has been printed onto of the monolithic ceramic capacitor structure 120. In this particular case, this is a rectangular spiral inductor 180 which is even more efficient. There are two alternatives for the inductor printing shown on FIGS. 23 and 24. FIG. 23 is a pentagonal shape inductor 180 while FIG. 24 is a spiral round inductor 180 which is very efficient. There are a number of other shapes that will be obvious to those skilled in the art that could be used. In all cases, the inductor 180 is terminated and connected to telemetry pin 116 on one end and ground termination 122 on the other end.

Figures 25, 26, 27:
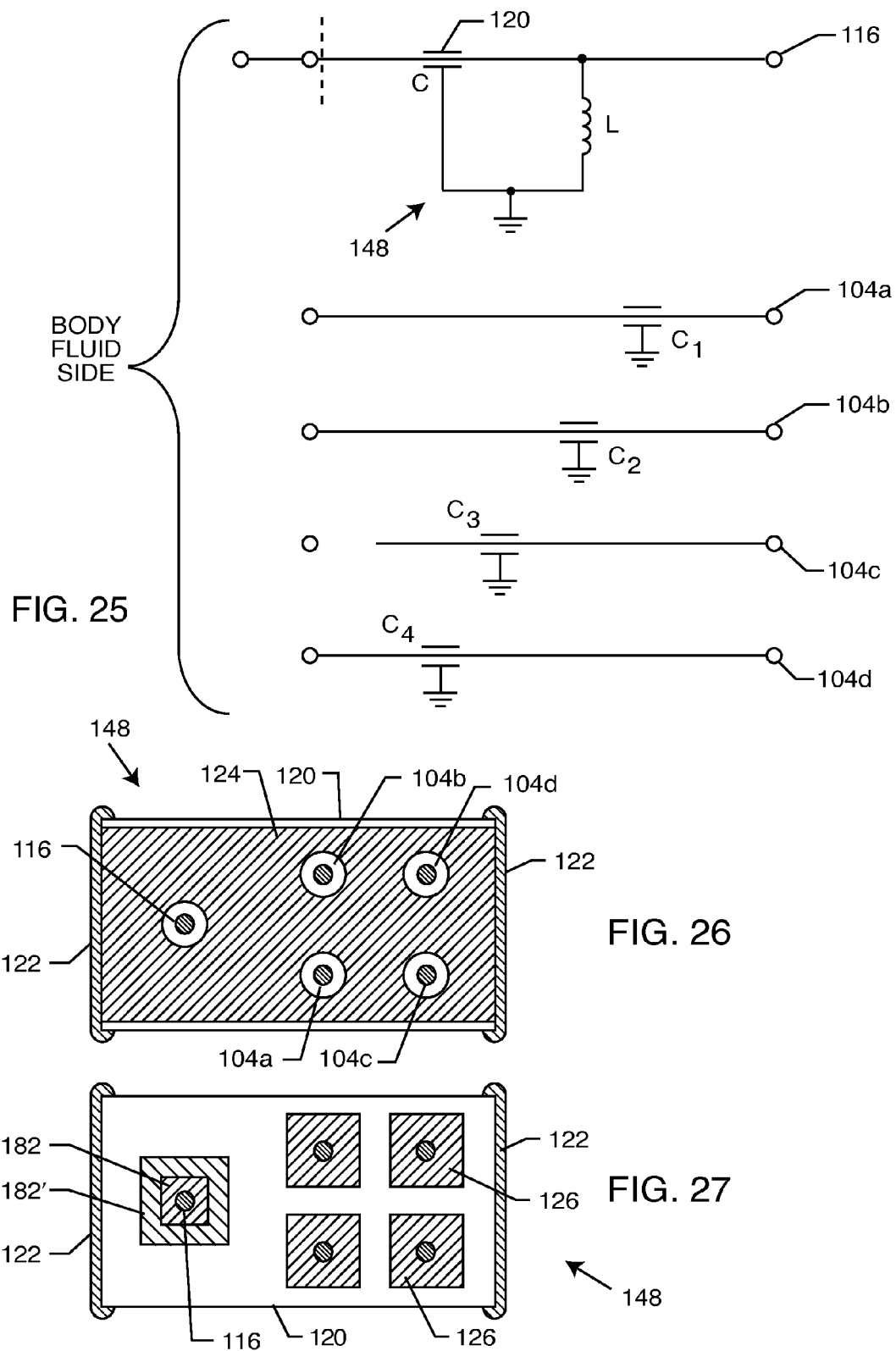
FIG. 25 is an electrical schematic diagram for the combined feedthrough capacitor with inductor for RF telemetry pin shown in FIG. 22.
FIG. 26 is a sectional view taken generally along the line 26-26 of FIG. 22.
FIG. 27 is a sectional view taken generally along the line 27-27 of FIG. 22.

The schematic diagram of the novel combined EMI feedthrough capacitor of parallel tank chip 120, which is previously illustrated in FIG. 22, is shown in FIG. 25. As one can see, there is a parallel tank circuit 148 that is shown on RF telemetry pin 116 (equivalent to FIG. 13 in function). One can also see that EMI filter capacitors $C_1, C_2, C_3$ and $C_4$ have been provided on lead wires 104 a-d. Referring once again to FIG. 22, sectional views 26-26 and 27-27 have been taken to show the internal electrode plates of the embedded capacitor elements. Referring to FIG. 26, one can see the ground electrode plate set 124. The ground electrode plate set 124 is attached to termination surfaces 122 on both ends of the novel combined EMI filter in the parallel tank 148.

Referring to FIG. 27, one can see the active electrode plate sets 126 that are connected to each of the individual lead wires. When these electrode plates 126 overlap the ground electrode plate 124, that makes a highly efficient, very low inductance, feedthrough capacitor EMI filter 120 that is well known in the prior art. However, referring once again to FIG. 27, one can see area 182 which is the smaller cross-hatched area. When area 182 overlaps the ground electrode plate 124, this forms a capacitance. The amount of the capacitance is selected so that it will resonate with the inductor at the selected telemetry frequency. This is best understood by referring back to FIG. 24 to realize that the inductor spiral 180 is now in parallel with the capacitance that is formed by the overlap of area 182 in FIG. 27 with the ground plate set 124 previously described in FIG. 26. One can control the amount of this capacitance in two ways. One would be to add multiple capacitor electrode alternating ground and active layers. However, one could also increase the capacitance by increasing the amount of active electrode plate area. This is shown as an optional area 182' illustrating that one can control the amount of capacitance in the parallel tank 148 by simply controlling the amount of electrode that is silk-screened down on the monolithic ceramic capacitor structure.

Figure 28:
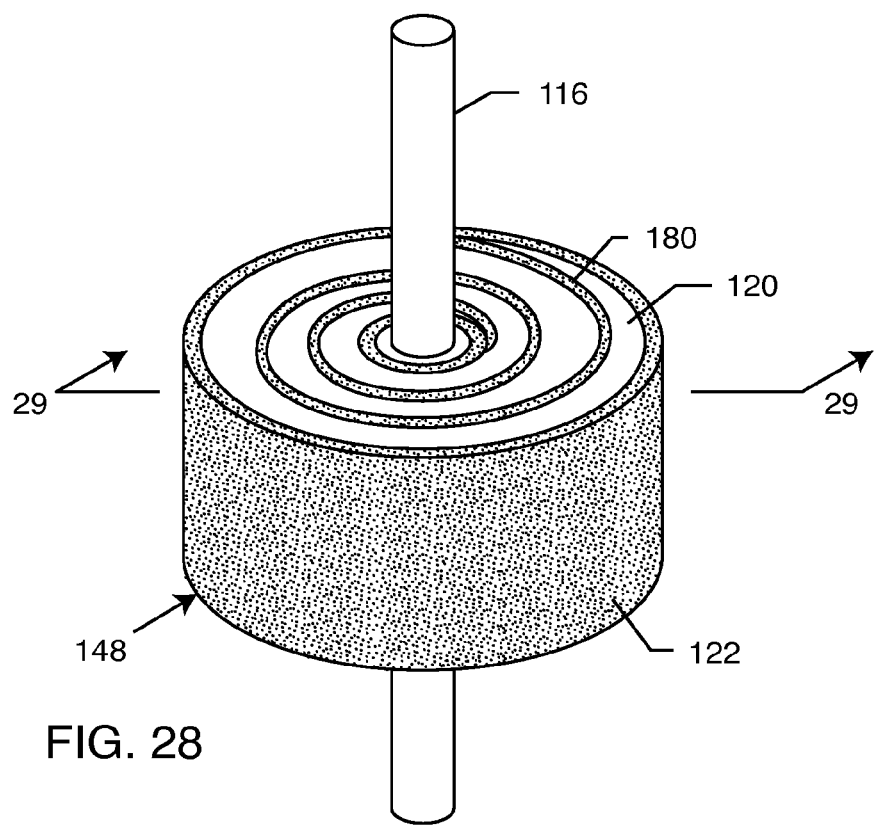
FIG. 28 is a perspective view of a unipolar feedthrough capacitor with a spiral wound inductor element embodying the present invention.
Figure 29:
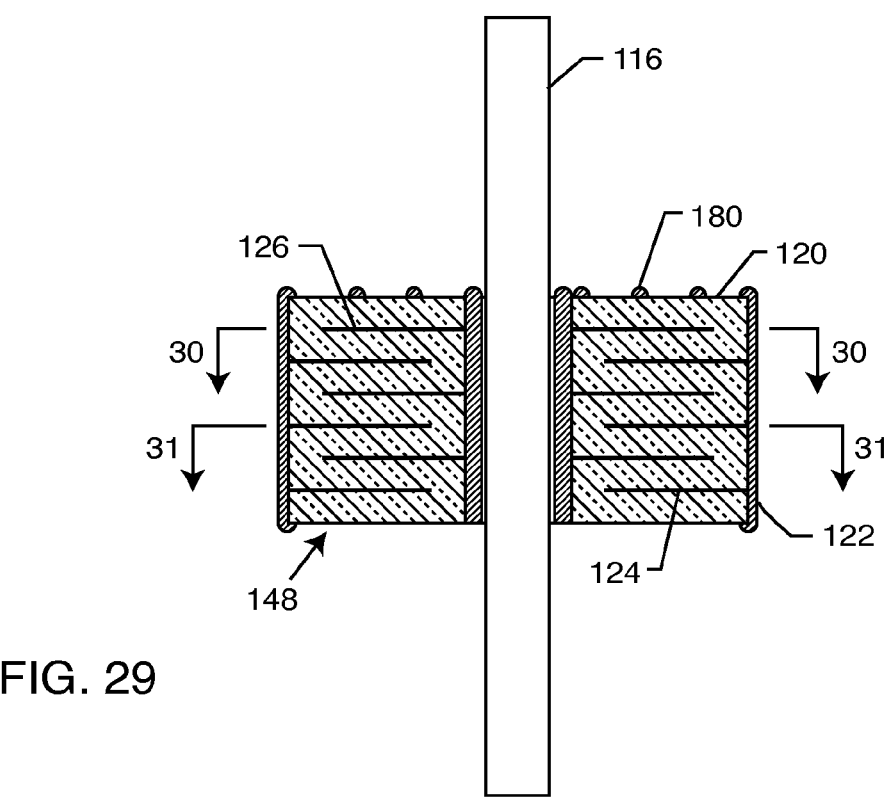
FIG. 29 is a sectional view taken generally along the line 29-29 of FIG. 28.
Figure 30:
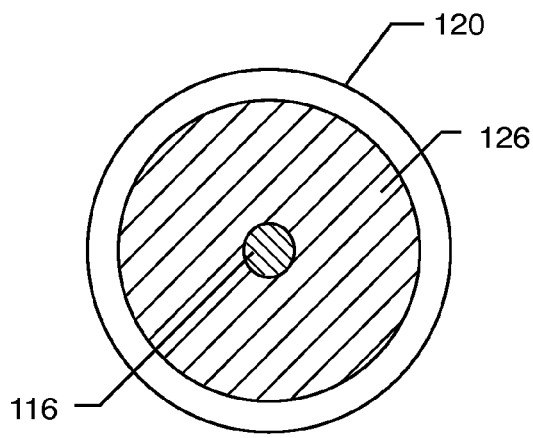
FIG. 30 is a sectional view taken generally along the line 30-30 of FIG. 29.
Figure 31:
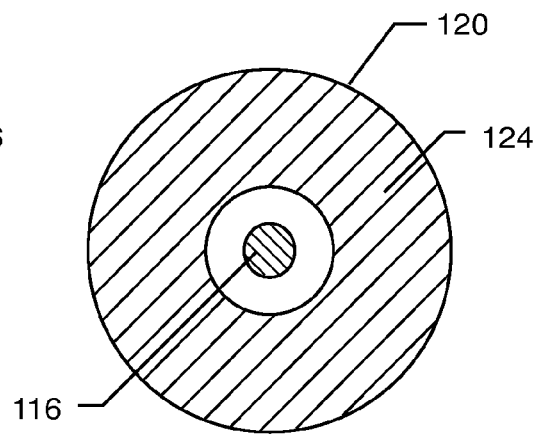
FIG. 31 is a sectional view taken generally along the line 31-31 of FIG. 29.
Figure 32:
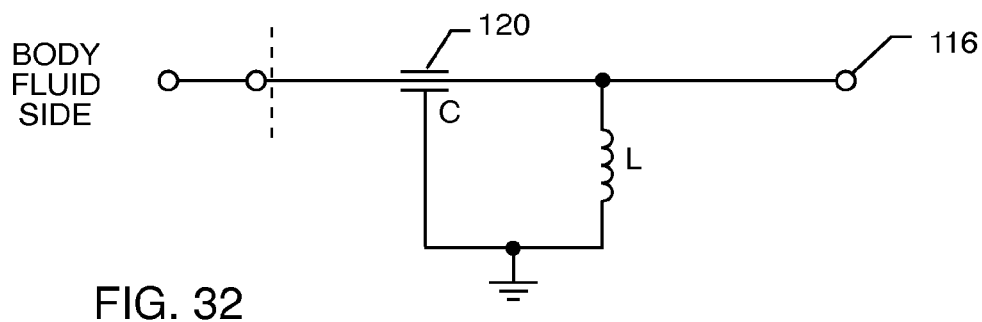
FIG. 32 is an electrical schematic illustration of the parallel tank circuit formed by the structure shown in FIGS. 28-31.

FIGS. 28 and 29 show a unipolar feedthrough capacitor 120 with a spiral wound inductor element 180 that is printed on to it. This is an alternative to the composite EMI filter and tank circuit shown in FIG. 22. In this case, the unipolar capacitor 120 would be placed on the unipolar RF telemetry pin 116 as shown in FIG. 8 alongside the prior art quadpolar feedthrough capacitor. Spiral inductors are well known in the prior art and are highly efficient. Efficiency in this case means that a substantial amount of inductance can be created in a relatively small area while at the same time keeping the overall length of the inductor relatively short. That is, the DC resistance and therefore the Q of the inductor will be held within acceptable limits for biomedical tank circuit applications. Referring once again to FIG. 29, one can see sectional views 30-30 and 31-31 that have been taken that show the capacitor's internal electrode plates. FIG. 30 shows the capacitor's active electrode plate set 126 and FIG. 31 illustrates the unipolar capacitor's ground electrode plate set 124. Such capacitors are well known in the prior art. FIG. 32 illustrates the schematic of the parallel tank circuit 148 that is formed by the structure previously illustrated in FIG. 28.

Figures 33, 34:
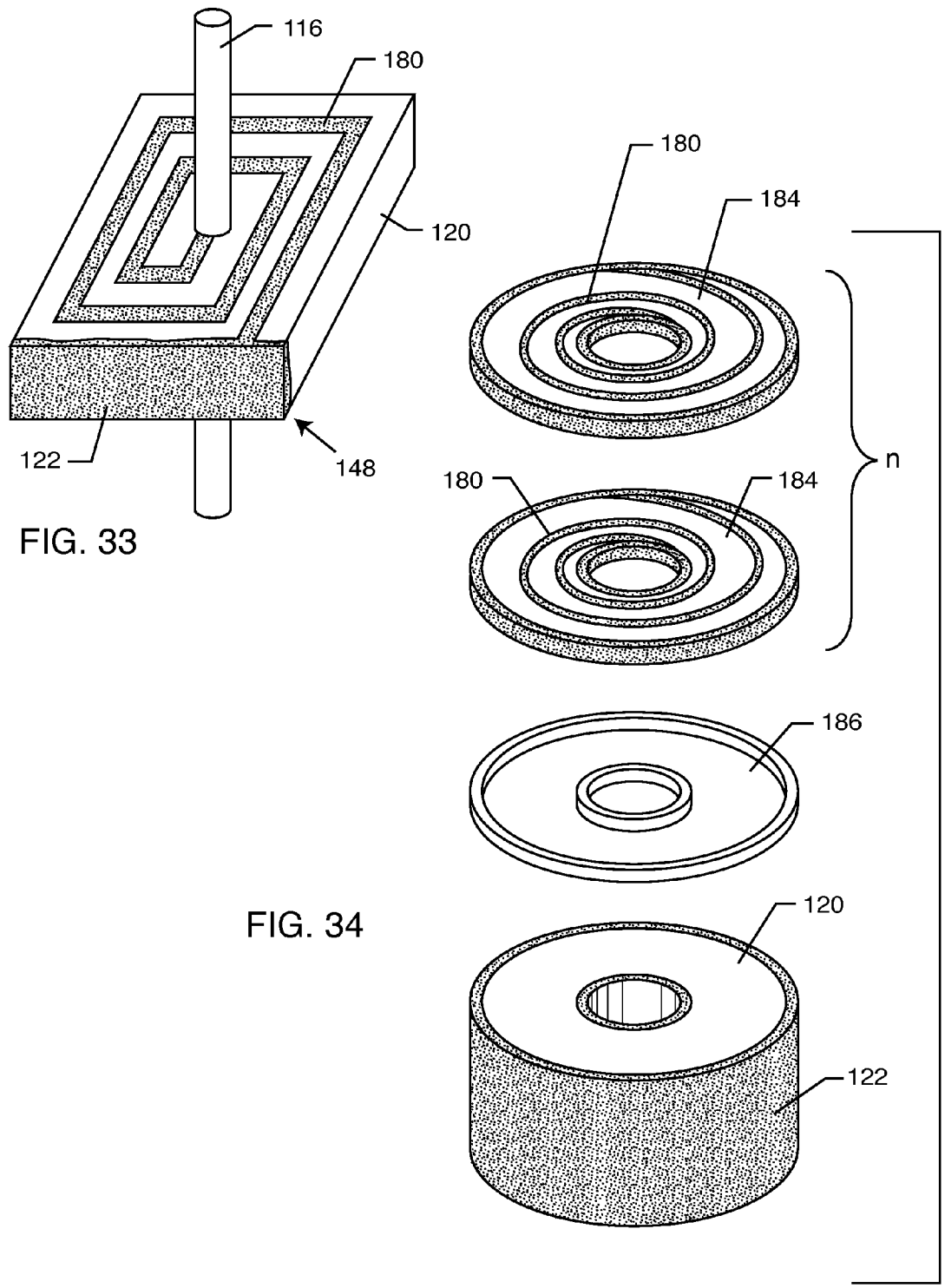
FIG. 33 is an alternate embodiment of a unipolar capacitor tank filter similar to that shown in FIG. 28.
FIG. 34 is an exploded perspective view of an alternative embodiment for creating the novel unipolar tank filter of the present invention.

FIG. 33 is an alternate embodiment of the unipolar capacitor (discoidal) tank filter illustrated in FIG. 28. This has a rectangular shape, however, it will be obvious to those skilled in the art that any number of shapes could be used. The inductor 180 pattern itself can be formed in many ways, including deposition of metals through silk-screening, physical vapor deposition, chemical vapor deposition, direct printing, photo lithography, plating, sputtering, plasma arc deposition, ion beam deposition, metal cladding, the strategic placement of metal tapes and the like.

FIG. 34 illustrates an alternative embodiment of creating the novel unipolar tank filter 148. There is a novel substrate 184 which would typically be of alumina substrate material into which the inductor spiral 180 has been printed. This can be done on both sides (top and bottom) of the substrate 184 so that they act in parallel. As previously mentioned, the total inductance of inductors acting in parallel would be one half. However, an additional advantage is that the DC resistance of such structure would also be halved. Multiple (n) layers can be stacked up as shown in FIG. 34 which reduces the resistance of $R_L$ by 1/n. This allows the use of alternate materials that would have to be fired at different temperatures than the monolithic ceramic capacitor 120 itself. Therefore, substrate 184, with its imprinted inductors 180, could be fired and then subsequently added onto the top of a prior art discoidal capacitor 120. Electrical attachment of these structures could be by any convenient method. One such method is to utilize pre-forms 186. These pre-forms could be of a thermosetting conductive adhesive, solder, braze or the like.

Figure 35:
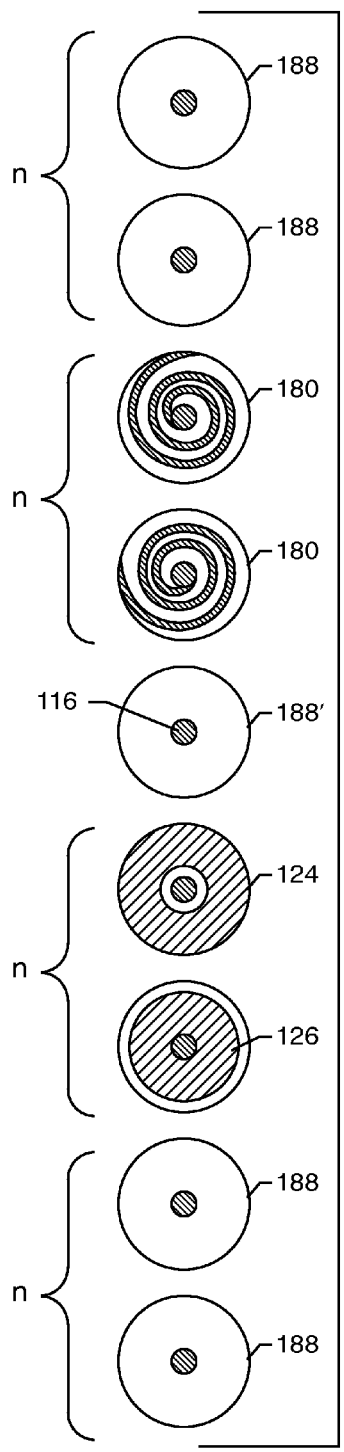
FIG. 35 illustrates another alternative embodiment for constructing the novel unipolar tank circuit previously described in FIG. 28.
Figure 36:
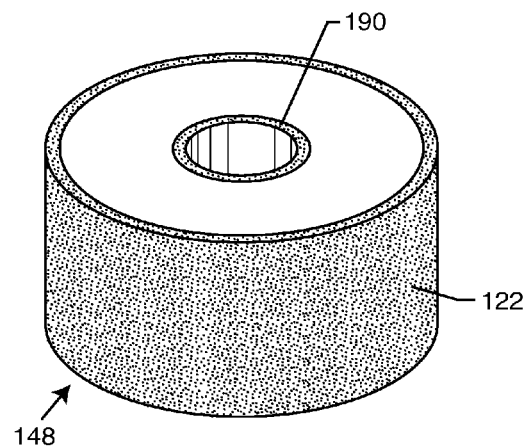
FIG. 36 is a perspective view of a monolithic tank filter embodying the present invention including the components shown in FIG. 35.
Figure 37:
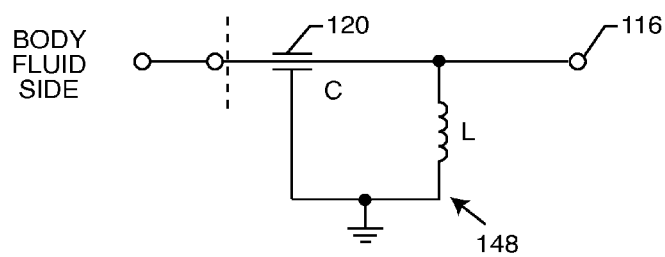
FIG. 37 is an electrical schematic illustration of the structure shown in FIGS. 35 and 36.

FIG. 35 is another alternative method of constructing the novel unipolar tank circuit 148 previously described in FIG. 28. In this case, the inductor spirals 180 have been embedded within the capacitor structure itself, resulting in the monolithic structure shown in FIG. 36. FIG. 36 is an isometric view of what appears to be a feedthrough capacitor. However, inductor spirals 180 have been embedded within it so that the schematic diagram of FIG. 37 is achieved which is of course the parallel tank 148 of the present invention. Referring back to FIG. 35, one can see that there are blank insulating cover sheets 188 which can vary from one to many, and then there are a number of embedded inductor spirals 180 which can vary from one to many. Then there are one or more insulating dielectric layers 188' which separate the capacitor's ground electrode plates 124 and active electrode plate sets 126. As previously mentioned, this can vary from one active and one ground electrode to as many as 400 of these acting in parallel depending on the amount of capacitance desired. This entire structure would be screen-printed on ceramic tape, then pressed, then sintered, then pressed in a binder bake-out operation, and then sintered again (firing would occur at high temperature). This would form the monolithic block structure shown in FIG. 36. Metallization layers 122 and 190 would be added to make convenient connection to the capacitor's electrode plates and also both ends of the inductor spiral(s).

Referring back to FIGS. 35 and 36, there are a number of alternative ways to construct the novel MLCC composite chip capacitor-inductor tank. One way is through thick film printing methods. Thick film printing of capacitors is well known in the prior art. A novel feature of the present invention is to incorporate capacitor layers interspersed or layered on top of inductor layers. These could be laid down on a substrate, dried and then fired as a composite structure. Equivalent methods include photolithography and vapor deposition techniques. It is obvious to those skilled in the art that there are a number of ways to manufacture the novel composite MLCC capacitor inductor tank of the present invention.

Figure 38:
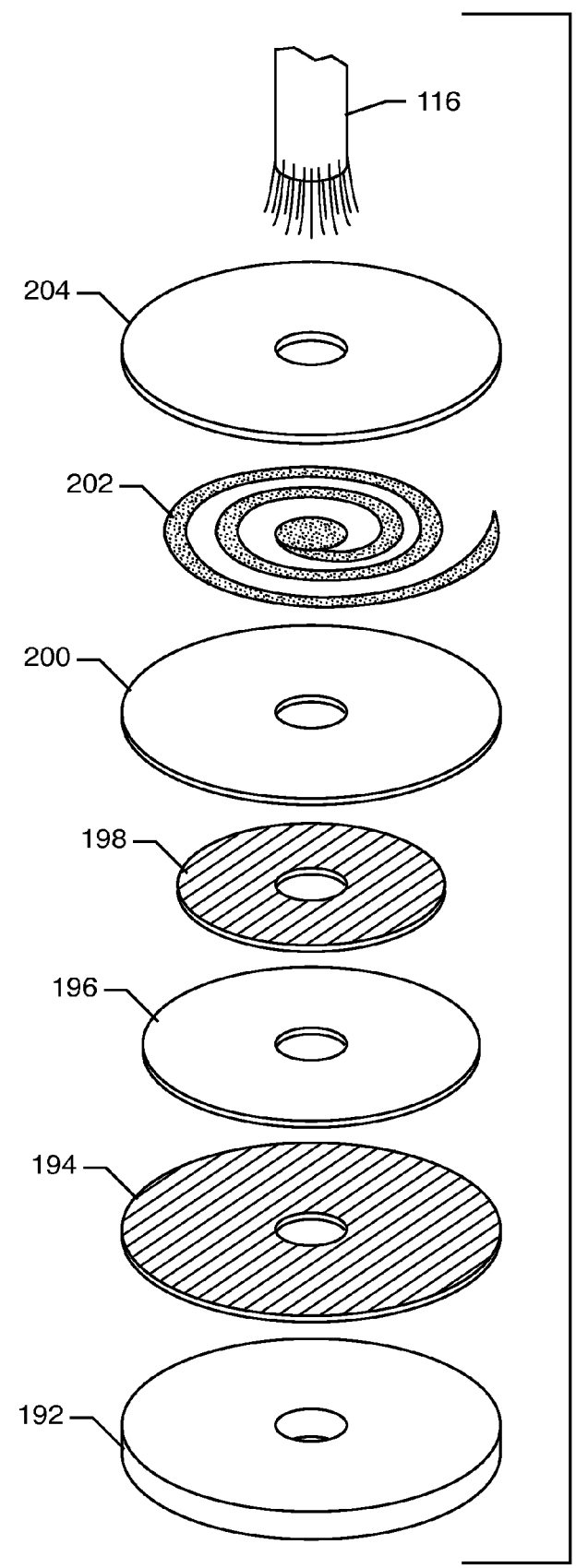
FIG. 38 is an exploded perspective view of yet another alternative manufacturing technology utilized to achieve the novel tank circuit of the present invention.

FIG. 38 is another alternate manufacturing technology to achieve the novel tank circuit of the present invention. It should be noted at this point that any of these methods are applicable to any of the geometries that are described herein or in the prior art. That is, the overall tank can be rectangular, it can be square, it can be round, it can be oval and the like. FIG. 38, shows using a thick film deposition process to build the parallel tank circuit 148. Starting from the bottom, one starts with a substrate 192. In the preferred embodiment, this would typically be a thin alumina substrate. Then a layer of conductive ink 194 is laid down on top of the substrate using conventional thick film processes. This can be done by silkscreening or any of the aforementioned deposition processes. Then there would be a ceramic dielectric insulating layer 196 that is laid down on top of the conductive layer 194. Then there would be a smaller in diameter active electrode plate layer which is conductive 198 which is printed down on top of dielectric layer 196. This can be repeated many times so as many layers of 194 and 198 that are required can be achieved. In other words, if one needs to increase the capacitance value, one can use multiple alternating sets of ground electrodes 194 (124) and active electrodes 198 (126). Then there is a layer of insulating material 200 which can be of either high or very low dielectric constant. This electrically isolates the capacitor portion of the parallel tank from the inductor portion to follow. A second or more (n) layers 200 can also be added to add mechanical strength and additional electrical integrity. One then prints on top of layer 200 the inductor spiral 202 as shown. Again, it should be noted that these layers are printed directly right on top of each other after a very short drying period. One or more inductor spirals 202 and insulators 200 can be placed down depending upon the amount of inductance required and the amount of DC resistance that is tolerable. Then one or more insulating layers 204 are laid down on top to mechanically and cosmetically seal the structure.

Figure 39:
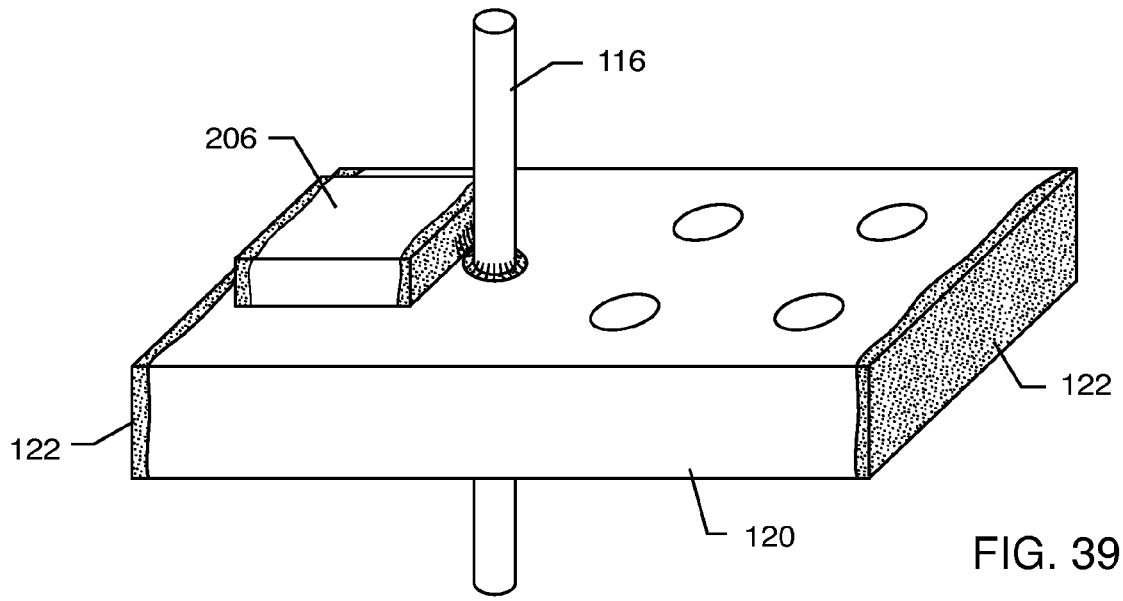
FIG. 39 is a perspective view of an integrated EMI filter and parallel tank capacitor, utilizing a monolithic chip inductor disposed on a surface of the capacitor and terminating at one end to the RF telemetry pin and at another to ground metallization.
Figure 40:
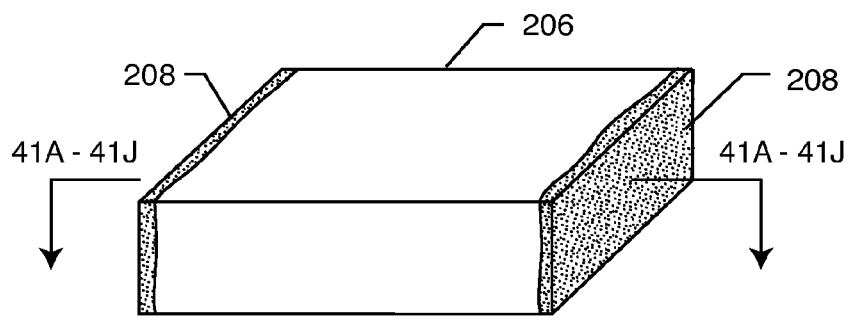
FIG. 40 is an enlarged perspective view of the inductor chip shown in FIG. 39.
Figure 41A:
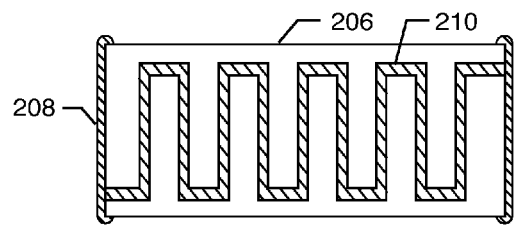
FIGS. 41A-41J illustrate a number of meandering inductor shapes that can be incorporated into the inductor chip of FIG. 40.
Figure 41F:
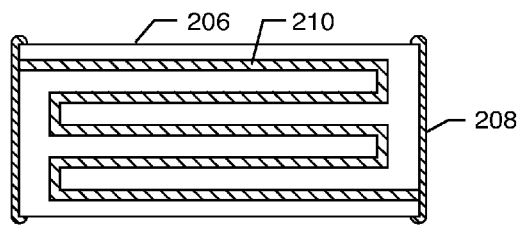
Figure 41B:
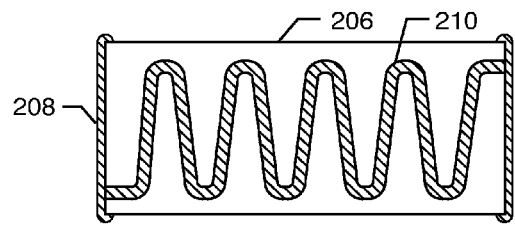
Figure 41G:
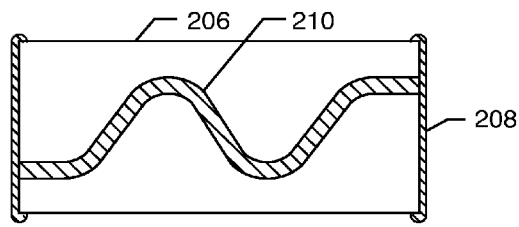
Figure 41C:
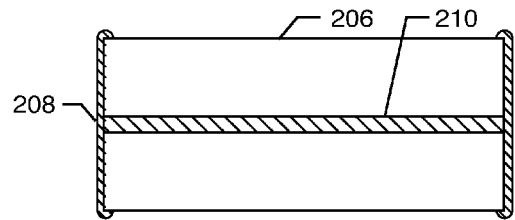
Figure 41H:
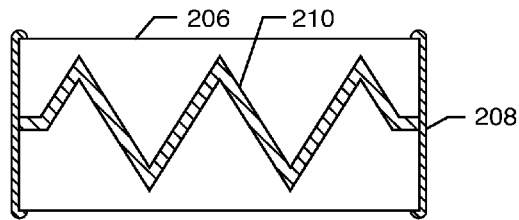
Figure 41D:
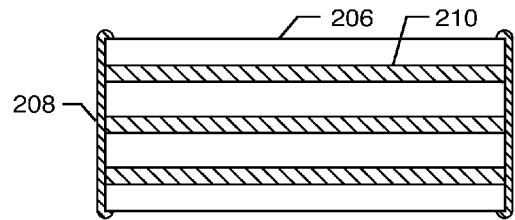
Figure 41I:
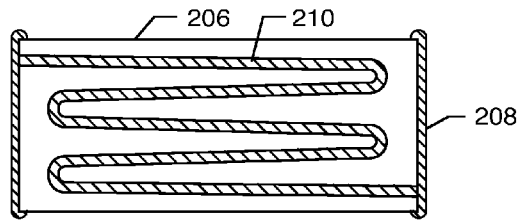
Figure 41E:
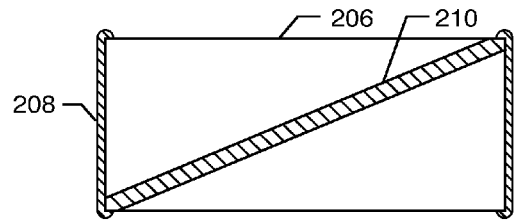
Figure 41J:
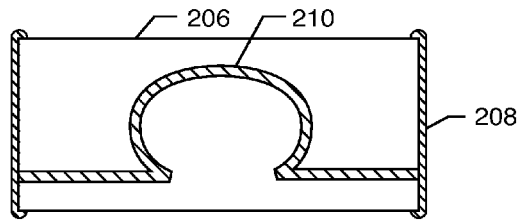

FIG. 39 is an alternative methodology of adding an inductor without the need to print it on top of the integrated EMI filter and parallel tank capacitor. In this case, a separate chip inductor 206 has been added which connects between the RF telemetry pin 116 and the capacitor's outer ground termination 122. This is better illustrated in FIG. 40 which shows the inductor chip 206 with its own terminations 208 on each end. Such inductor chips are known in the prior art, however, sectional views 41, 42 and 46 better illustrate the layers that can be inside such chips.

Referring to FIGS. 41A-41J, one can see a number of meander inductor shapes 210. The most efficient of these shapes are shown in 41A and 41B in terms of amount of inductance per unit volume. As previously mentioned, any number of these can be stacked up in parallel which would tend to reduce the overall inductance, but also decrease the DC resistance. The shapes illustrated in FIGS. 41A-41J are examples of the embedded inductor traces that can be used, but are not meant to be completely comprehensive. In other words, it will be obvious to those skilled in the art that any number of shapes can be used.

Figure 42:
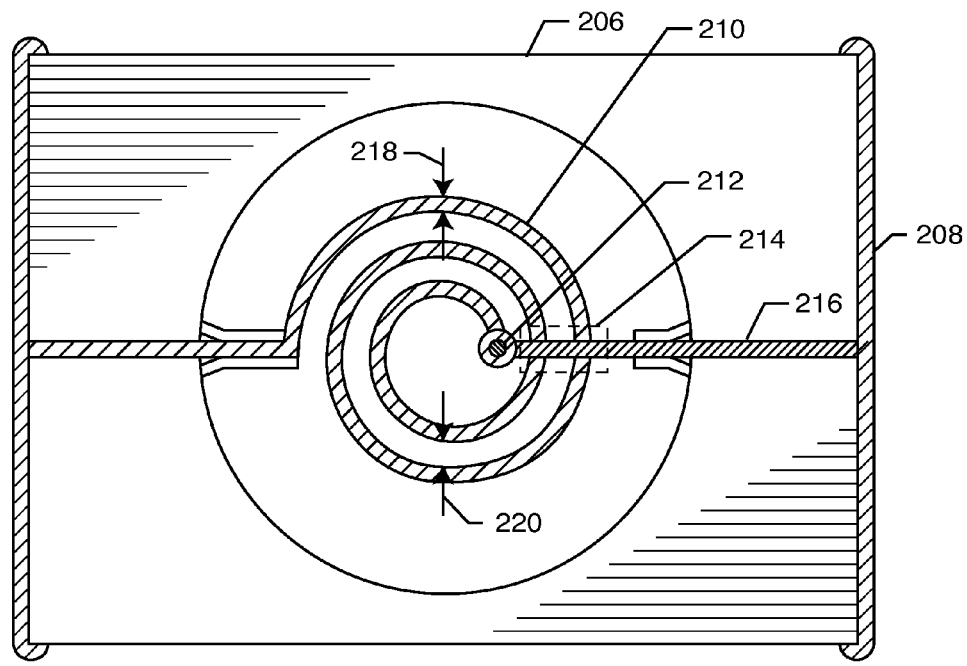
FIG. 42 is a sectional view similar to FIGS. 41A-41J, illustrating a spiral inductor which is more efficient than the meanders shown in FIGS. 41A-41J.

FIG. 42 shows a spiral inductor shape 210 which is much more efficient than any of the meanders shown in FIG. 41. The reason for this has to do with the compaction of electromagnetic field lines around a center structure. This is a little more difficult to make than a meander because the lead wire at 212 must be brought out across its own lead wires in insulative relationship. In this case, there is a insulating pad 214 which is typically formed with a thick film printed insulating layer that will cover the bottom inductor spirals so that the inductor 210 does not short out as it crosses at that point. Another way to achieve this is with a via hole 212 which is shown in FIG. 42. In this way, the inductor spiral 210 could be printed and then an insulative layer could be printed on top of it which includes the straight trace 216 and a via hole would be punched through and filled with a conductive material so that a circuit connection is made. Modified wheeler equations are very useful in predicting the performance of such inductors. The ratios between width of coil 218 and spacing of coils 220 turn out to be very important. In this type of inductor spiral, we tend to get equal responses which makes for a very efficient geometry. Accordingly, the spiral shape shown in FIG. 42 is one of the preferred embodiments of the present invention which is adaptable to any of the previously mentioned structures.

Figure 43:
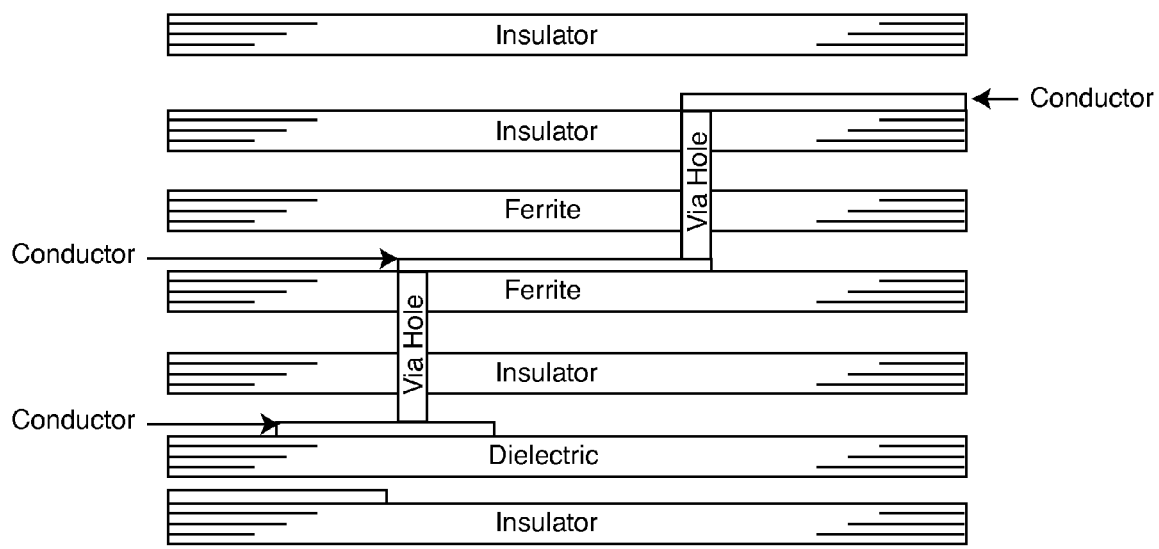
FIG. 43 illustrates an exploded sectional view of a typical film deposition that could be utilized to construct the spiral inductor of FIG. 42.

FIG. 43 illustrates an exploded sectional view of a typical thick film deposition that could be used in conjunction with the spiral inductor of FIG. 42 or any of the other technologies described herein. We have alternating insulator layer and then ferrite layers with via holes in between to connect through. There can also be embedded conductor traces within such structures. This is meant by way of illustration only to illustrate how via holes can be used to connect circuit traces and inductors at various levels. FIG. 43 is an illustration of embedded technology that uses multiple tape compositions. The tapes are constructed in such a way that during firing their shrinkages are compatible. This makes for a highly volumetrically efficient packaging method. It results in a single monolithic component which includes internally embedded inductors, capacitors and resistor elements as desired to construct the parallel tank of the present invention.

Figure 44:
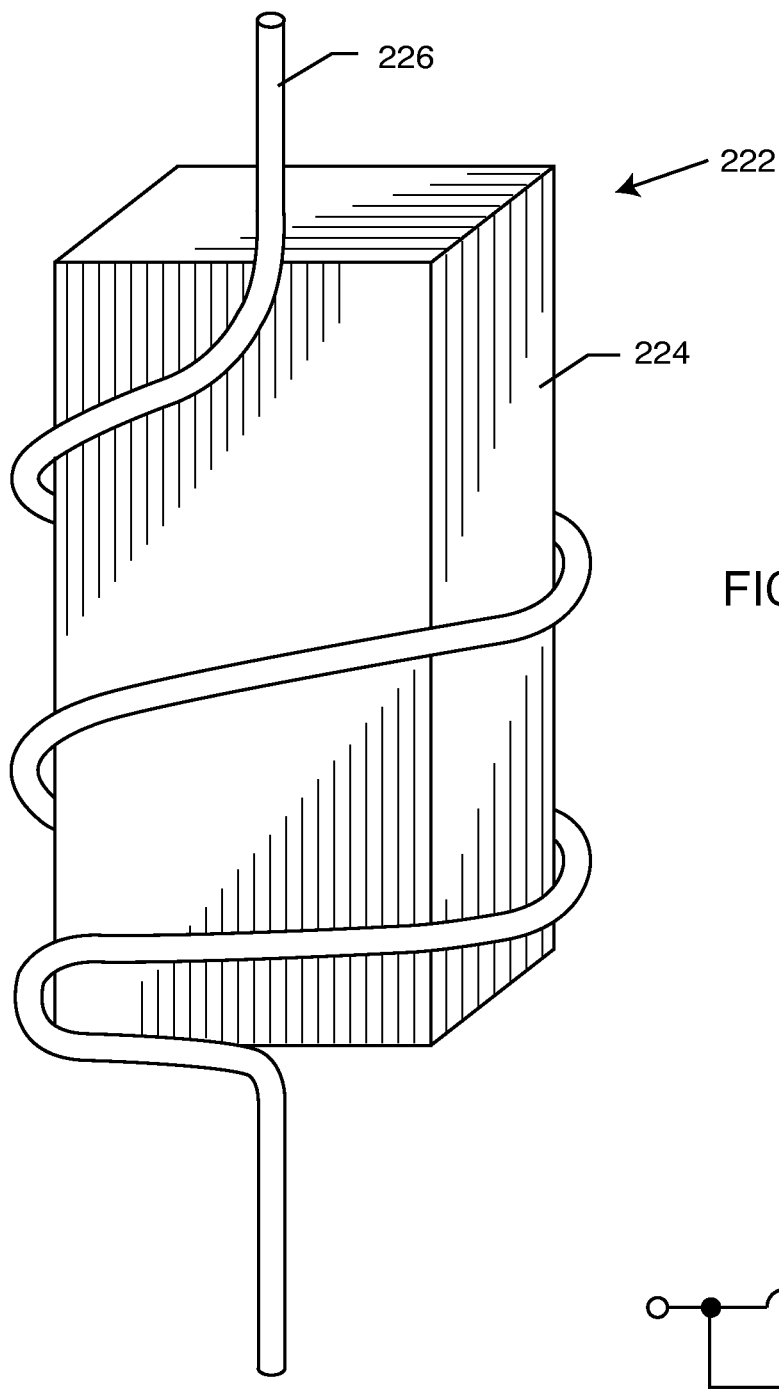
FIG. 44 is a perspective view of an inductor formed around a dielectric tape.
Figure 45:
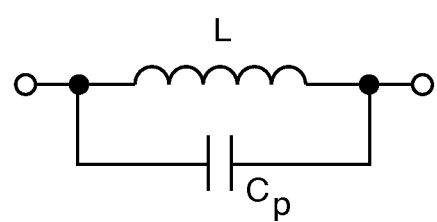
FIG. 45 is an electrical schematic diagram of the inductor element of FIG. 44.

FIG. 44 is a diagrammatic representation of an inductor 222 that is formed around a dielectric tape 224. This is illustrative of a thick film process inductor. One can see that a lead wire 226 has been wound in an efficient spiral. The tape 224 could be a ferrite material used in order to increase volumetric efficiency. However, in this case, in order to completely minimize MRI image artifact, material 224 would desirably not be ferromagnetic. In other words, 224 is an insulative or dielectric layer which is typical of such materials that are found in thick film printing. FIG. 45 is the schematic diagram of the inductor element illustrated in FIG. 44. $C_p$ is the parasitic capacitance. By using a high enough dielectric constant, $C_p$ can be adjusted to be resonant with L at the selected telemetry frequency. This novel use of the inductor's parasitic turn to turn capacitance can eliminate the need for a separate capacitor component.

Figure 46:
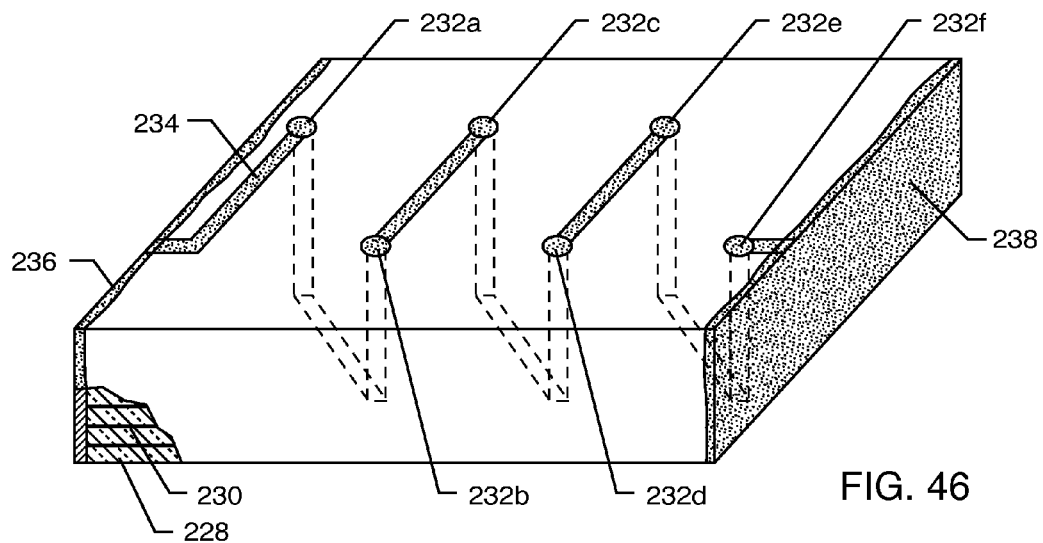
FIG. 46 is physical approximation using thick film processing to construct the spiral inductor shown in FIG. 44.

FIG. 46 is a physical approximation using thick film processing to construct the spiral inductor shown in FIG. 44. Of course, this does not come out a perfect spiral due to the limitations of rectangular thick film manufacturing. Thick film layers 228 are laid up in such a way along with the laying down of thick film inks 230 to build the composite structure shown in FIG. 46. Via holes 232a through 232f are drilled and filled with conductive material so that the inductor spiral makes a continuous approximation of the coil previously discussed in connection with FIG. 44. These are connected using ink traces 234 as shown. This is highly efficient in that it contains the magnetic fields and produces a significant amount of inductance in a very small unit area. It also has the effect of keeping the overall length of the inductor relatively short which minimizes its DC resistance. If a high dielectric constant material 228 is used, then parasitic capacitance $C_p$ can be increased as needed to resonate with the inductance at the selected telemetry frequency. Termination surfaces 236 and 238 are provided for convenient electrical connection to the embedded inductor spiral. It should also be noted that the substrate structure 228 can be made of a number of materials, including alumina or high dielectric constant ceramic, ceramic dielectric films that are typically printed or even ferromagnetic materials. In other words, this entire system could consist of laid down ferromagnetic tapes. By replacing the overall dielectric or insulative structure with a ferromagnetic material, the overall inductance between 236 and 238 would increase significantly. The ink traces 234 and via holes 232 would remain as previously described using highly conductive materials to keep the overall DC resistance low. A disadvantage of using ferrous materials for the body would be the tendency to have additional MRI image artifact as previously noted.

Figure 47:
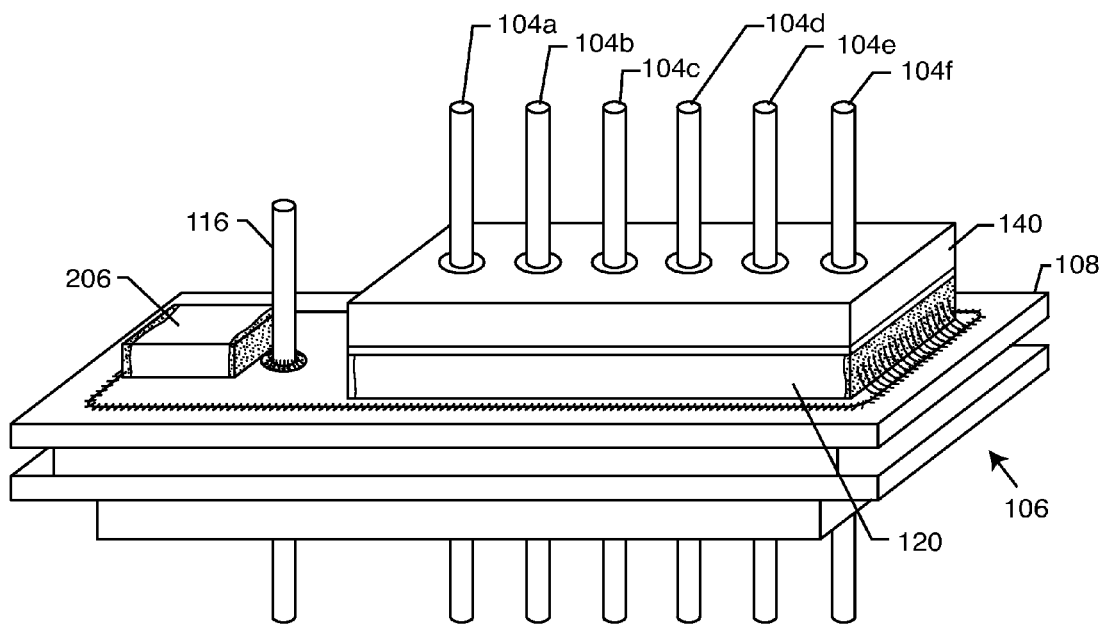
FIG. 47 is a perspective view of an inline hexpolar EMI filter terminal with an additional RF telemetry pin and a parallel tank chip electrically connected between a ferrule (ground plane) for the AIMD and the RF telemetry pin.
Figure 50:
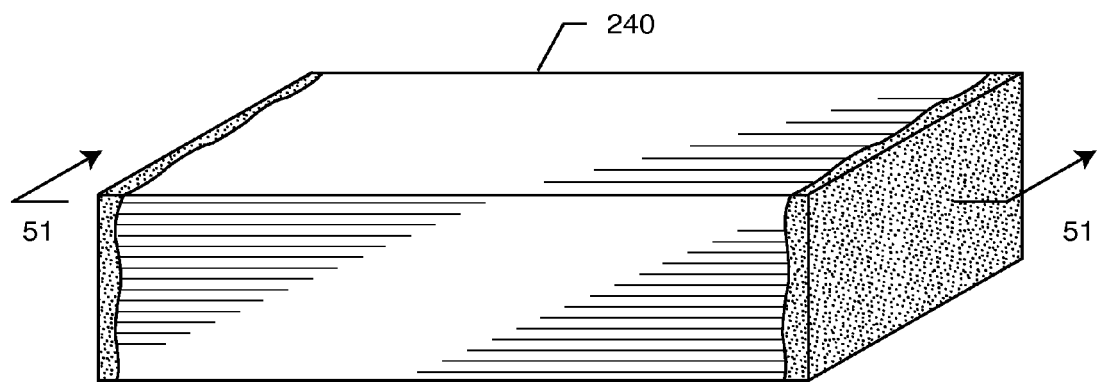
FIG. 50 is a perspective view of a prior art MLCC chip capacitor.
Figure 51:
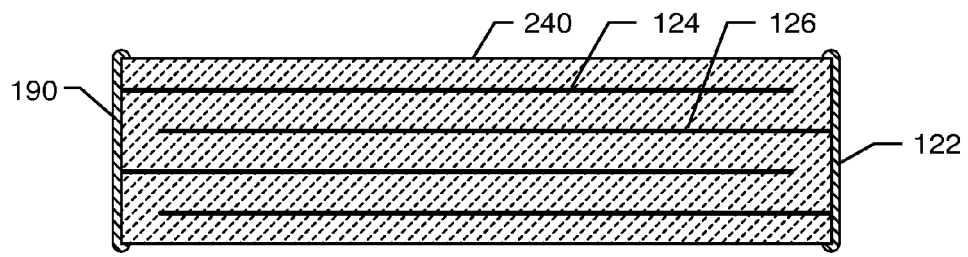
FIG. 51 is a sectional view taken generally along the line 51-51 of FIG. 50.
Figure 52:
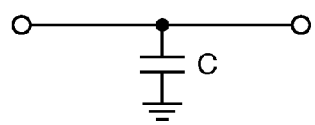
FIG. 52 is an electrical schematic of the prior art MLCC chip capacitor of FIGS. 50 and 51.
Figure 53:
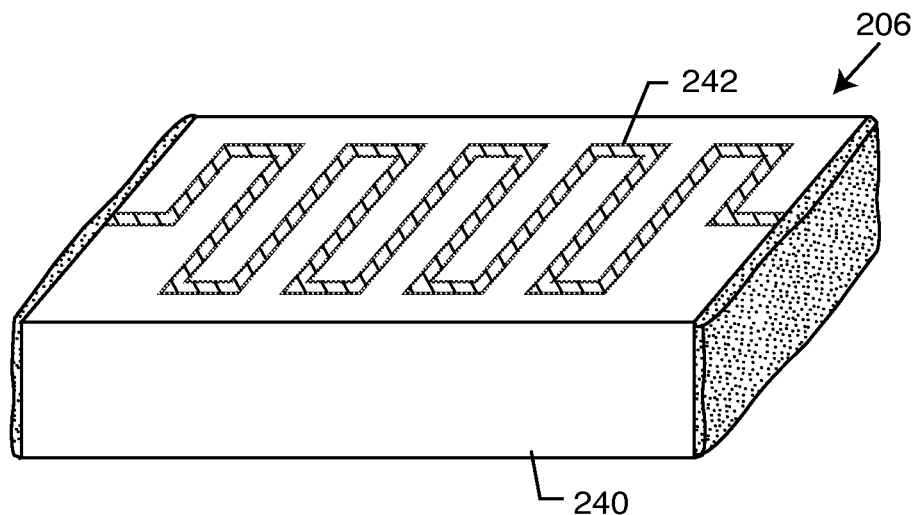
FIG. 53 is a perspective view of the MLCC chip capacitor of FIGS. 50 and 51, with an inductor printed on the surface.
Figure 54:
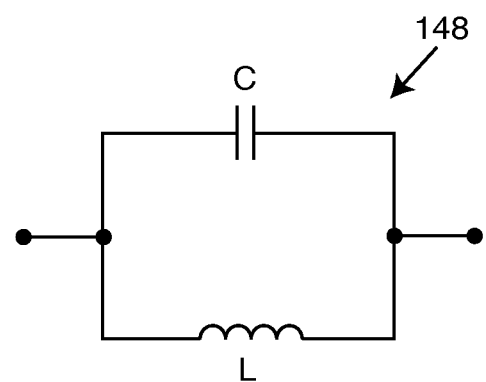
FIG. 54 is an electrical schematic showing how the structure of FIG. 53 creates the novel parallel tank circuit of the present invention.
Figure 56:
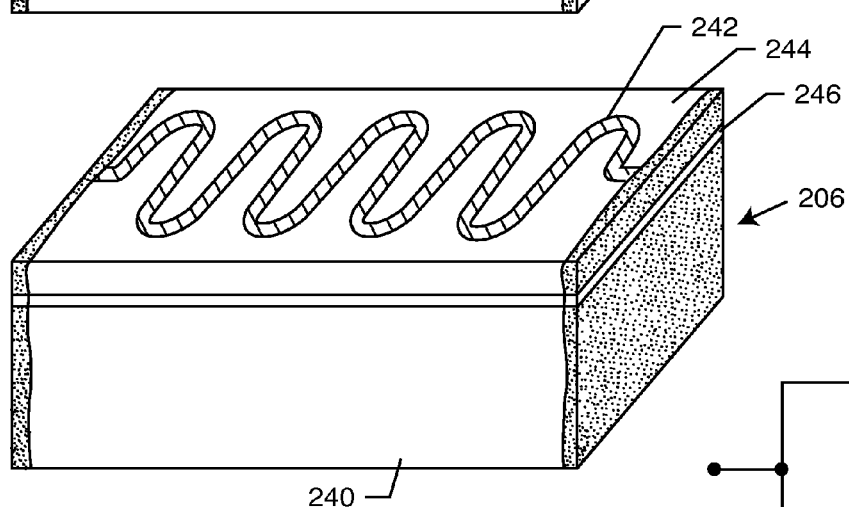
FIG. 56 is a perspective view illustrating the assembled structure of FIG. 55.
Figure 57:
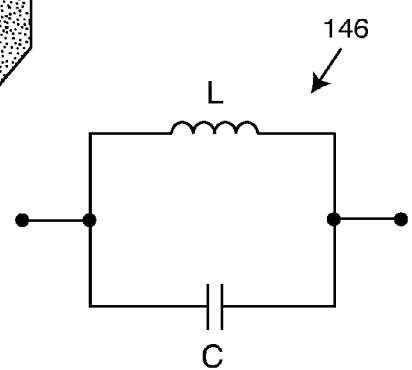
FIG. 57 is an electrical schematic illustration for the structure of FIG. 56.

FIG. 47 illustrates an inline hexpolar EMI filter terminal for an AIMD with an additional RF telemetry pin 116. This is illustrative of the fact that the present invention is not limited to quadpolar or any other number of leads. Referring once again to FIG. 47, one can see a prior art feedthrough capacitor 120 which has been bonded to the hermetic terminal ferrule 108. This feedthrough capacitor acts to provide EMI filtering for lead wires 104a through 104f. In addition, an inductor slab 140 has been co-bonded to the feedthrough capacitor 120 to increase the EMI filter performance in accordance with the L circuits of FIG. 7 (U.S. Pat. No. 6,999,818 and pending U.S. application Ser. No. 11/097,999). Referring once again to FIG. 47, one can see a novel parallel tank chip 206 which has been electrically connected between the ferrule 108 (ground) and telemetry pin 116. The parallel tank circuit 148 consists of an inductor and capacitor in accordance with the present invention. This is best understood by referring to the prior art MLCC capacitor 240 shown in FIG. 50 which has an inductor 242 printed on it as shown in FIG. 53, added as a substrate as shown in FIG. 56, or imbedded within it in accordance with FIG. 62 or entirely thick film printed in accordance with FIG. 66. FIG. 50 is a prior art MLCC chip capacitor. One can see in FIG. 51 that it has internal embedded electrode plate sets 124 and 126. FIG. 52 is the schematic diagram of the prior art MLCC chip of FIGS. 50-51.

Figure 48:
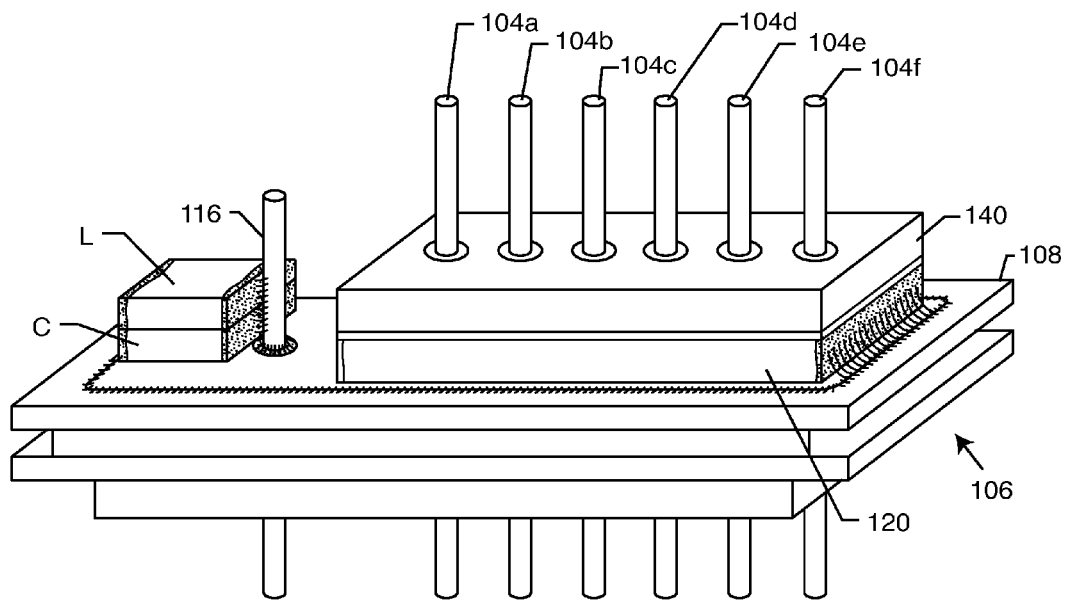
FIG. 48 is a perspective view similar to FIG. 47, illustrating the use of a commercially available MLCC chip capacitor in combination with a chip inductor to achieve the band pass filtering of the RF telemetry pin.

FIG. 48 shows an alternative embodiment to the structure shown in FIG. 47. In this case, commercially available MLCC chip capacitors C shown in FIG. 50 can be used commercial in combination with an "off the shelf" chip inductor L. Here an MLCC capacitor C has a commercially available chip inductor L stacked on top of it. Both of these have termination surfaces which are electrically connected in the right-hand case to the RF telemetry pin 116 and on the left-hand case to the gold braze of the hermetic seal which creates the circuit ground.

Figure 49:
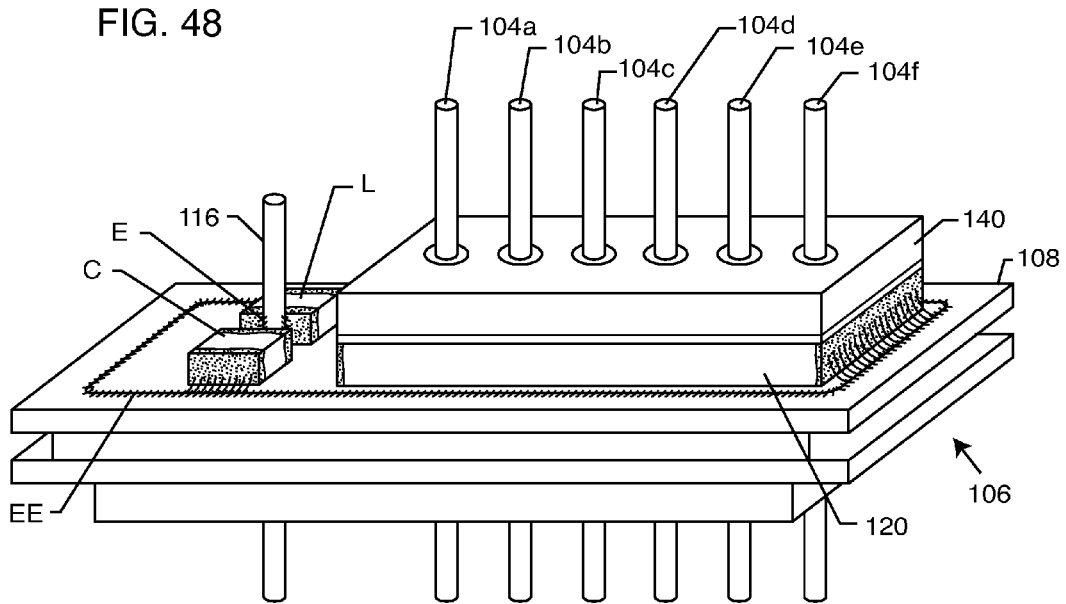
FIG. 49 is another alternative embodiment to the structure shown in FIGS. 47 and 48.

FIG. 49 is yet another alternative embodiment to the structure shown in FIG. 47. In this case, the commercial "off the shelf" MLCC chip capacitor C of FIG. 50 has been surface mounted and electrically connected E to the RF telemetry pin 116 and also electrically connected EE to the gold braze ground of the hermetic terminal flange 108. On the opposite side, there is a custom or commercially available chip inductor L which has been similarly electrically attached to the RF telemetry pin 116 and to the gold braze of the hermetic seal terminal flange 108. It is obvious to those skilled in the art that the chip capacitor and the chip inductor shown in FIGS. 48 and 49 can be literally placed in any location around the RF telemetry pin 116 as long as electrical connection is made between the terminal pin 116 and one termination surface of the inductor or capacitor and then a ground connection is made to the opposite termination surface of the inductor and capacitor.

Referring to FIG. 53, one can see an inductor 242 of the present invention has been printed onto the top surface of the prior art MLCC capacitor chip 240. This forms the novel parallel tank circuit 148 of the present invention illustrated in schematic FIG. 54.

Figure 55:
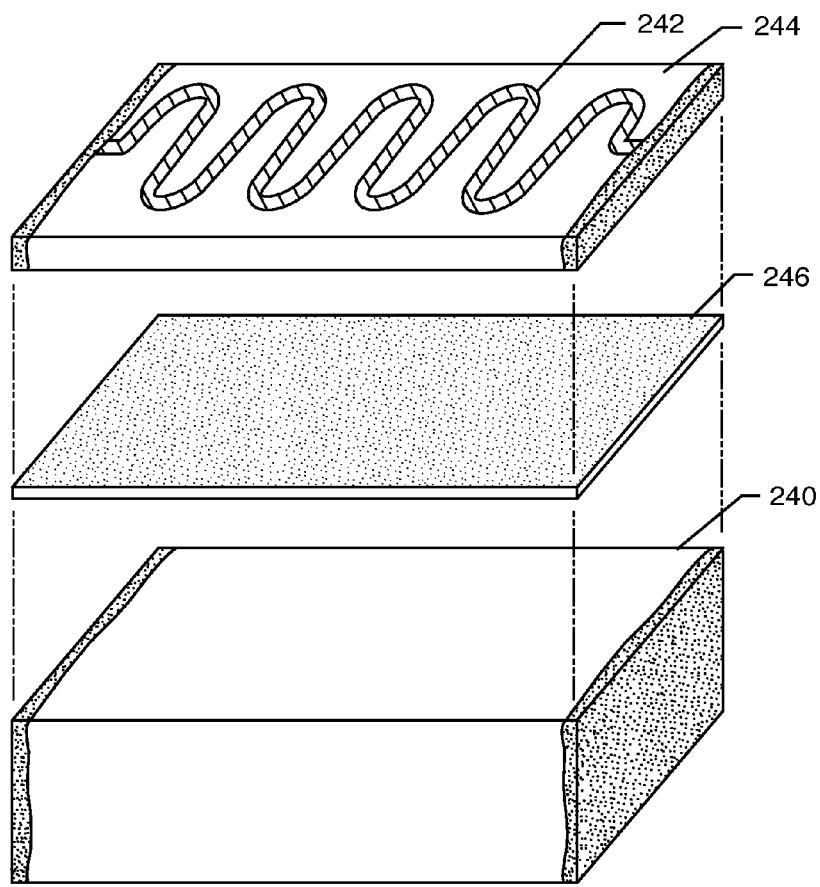
FIG. 55 is an exploded perspective view of a combined printed inductor with an MLCC chip capacitor similar to that shown in FIG. 53, but illustrating one alternative way of manufacturing it.

FIG. 55 illustrates a method of printing an inductor 242 on a substrate 244. The inductor 242 can be printed on both sides of said substrate 244. In addition, said substrate could be multilayer with any number of embedded inductor substrates. Then, illustrated is an adhesive bonding layer 246 which is used to attach to the inductor substrate 244 to the prior art MLCC capacitor 240. This results in the assembled structure of FIG. 56 and the parallel tank circuit as illustrated in schematic FIG. 57.

Figure 58:
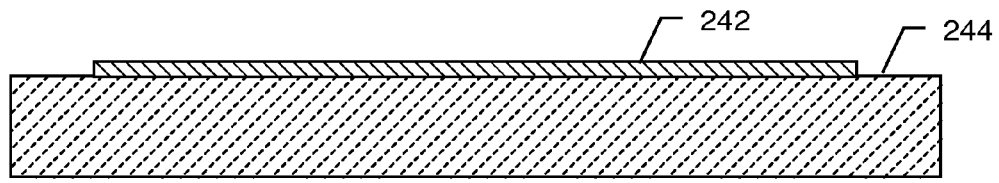
FIG. 58 is an enlarged sectional view of an inductor substrate layer such as that shown in FIG. 55.
Figure 59:
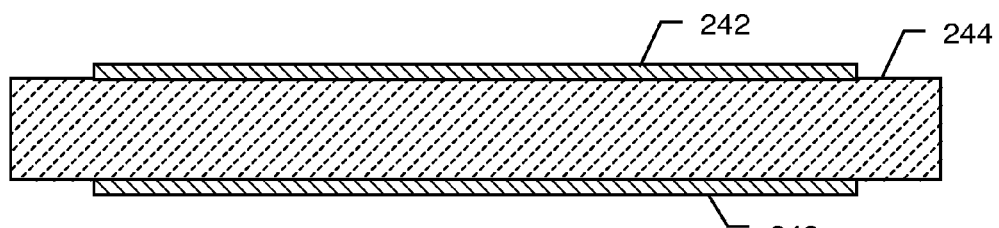
FIG. 59 is an alternative structure similar to FIG. 58, illustrating the inductor layer deposited on both sides of the substrate.
Figure 60:
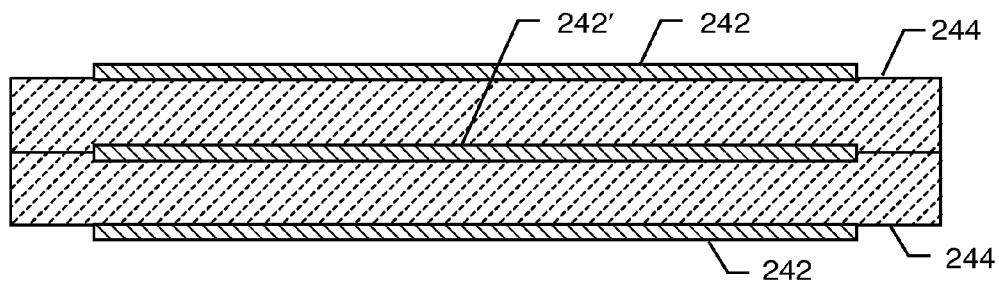
FIG. 60 is a view similar to FIGS. 58 and 59, illustrating a multi-layer substrate including an embedded inductor layer along with surface inductor layers.
Figure 61:
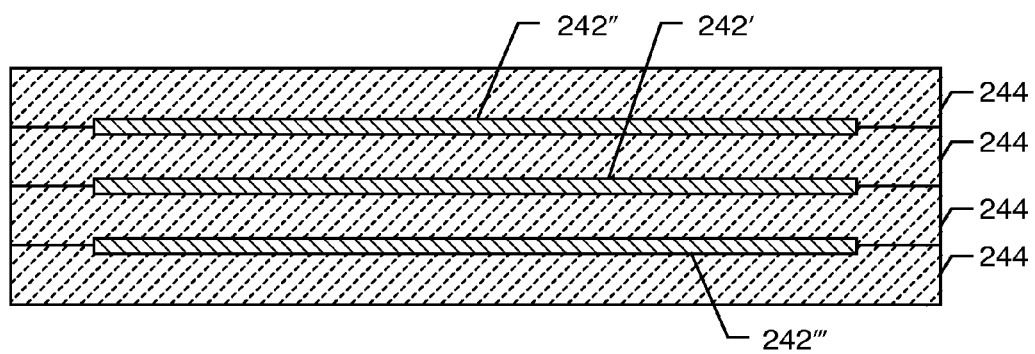
FIG. 61 illustrates another alternative embodiment similar to FIGS. 58-60, showing a completely embedded multi-layer substrate where there are no inductors on the surface.

FIG. 58 represents alternate views of the inductor substrate layer previously illustrated in FIG. 55 as substrate 244. FIG. 58 is identical to the substrate 244 previously illustrated in FIG. 55. FIG. 59 illustrates the inductor layer 242 deposited on both sides of substrate 244. FIG. 60 illustrates a multilayer substrate including an embedded inductor layer 242' along with surface inductor layers 242. FIG. 61 illustrates a completely embedded multilayer substrate where there are no inductors on the surface. In this case, inductors 242', 242" and 242'" or n inductors are all embedded within the structure.

Figure 62:
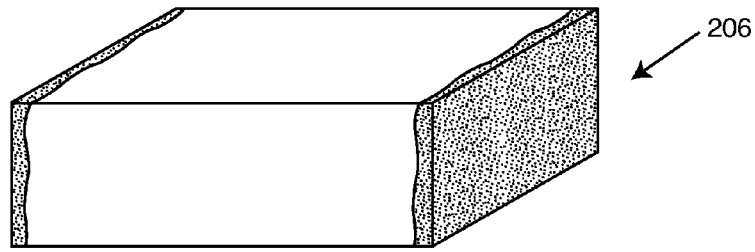
FIG. 62 is a perspective view of a novel MLCC-tank chip embodying the present invention.
Figure 63:
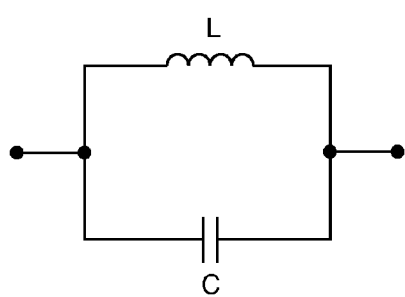
FIG. 63 is an electrical schematic illustration for the novel MLCC-tank chip of FIG. 62.
Figure 64:
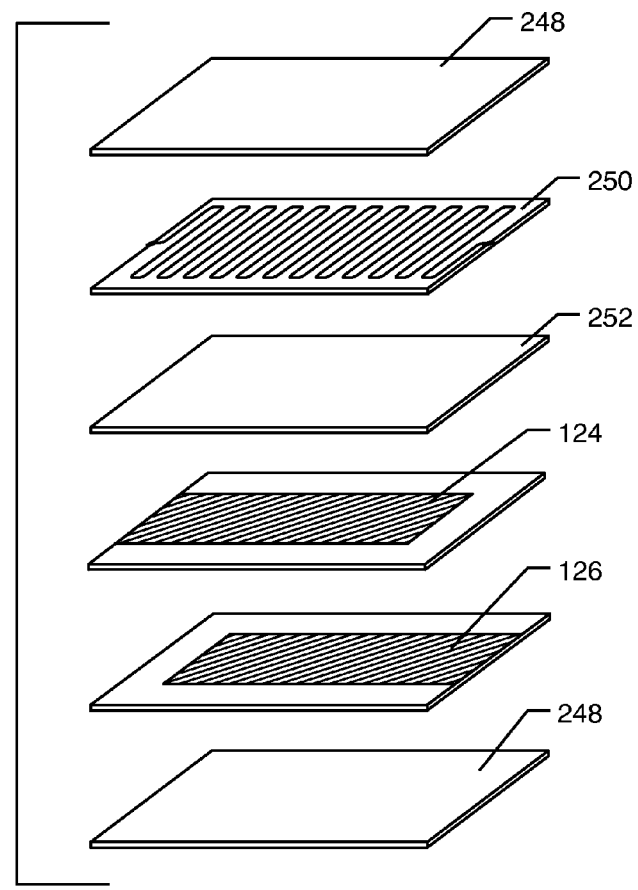
FIG. 64 is an exploded perspective view showing the various layers comprising the MLCC-tank chip of FIG. 62.

FIG. 64 illustrates a methodology of embedding inductor layers within a novel MLCC—tank chip 206 in FIG. 62. In this case, this becomes an integrated tank MLCC that has the schematic shown in FIG. 63. Referring once again to FIG. 64, one can see that there are blank cover sheets 248, then there are one or more inductor layers 250, then there are blank dielectric interleafs 252, then prior art capacitor dielectric electrode plate sets 124 and 126 and then more blank cover sheets 248. These are all pressed together then fired to form a solid monolithic structure, similar to a prior art MLCC chip capacitor.

FIG. 65 is a Table summarizing typical fabrication methods for laying down inductor and capacitor circuit traces. Low temperature co-fired ceramic (LTCC) generally consists of inductor materials built from silver or gold. However, emerging in the industry are base-metal materials (nickel) that could also be used. High temperature co-fired ceramics (HTCC) include the group of aluminum, copper, aluminum/copper alloys and the like. Monolithic Microwave Integrated Circuit (MMIC) consists of Gallium Arsenide, Indium Phosphide and the like. The next is Multichip Module-Deposition (MCM-D) consists of titanium, copper, aluminum and the like.

FIG. 66 Illustrates

FIG. 66 illustrates a thick film deposited parallel inductor capacitor tank of the present invention.

Figure 68:
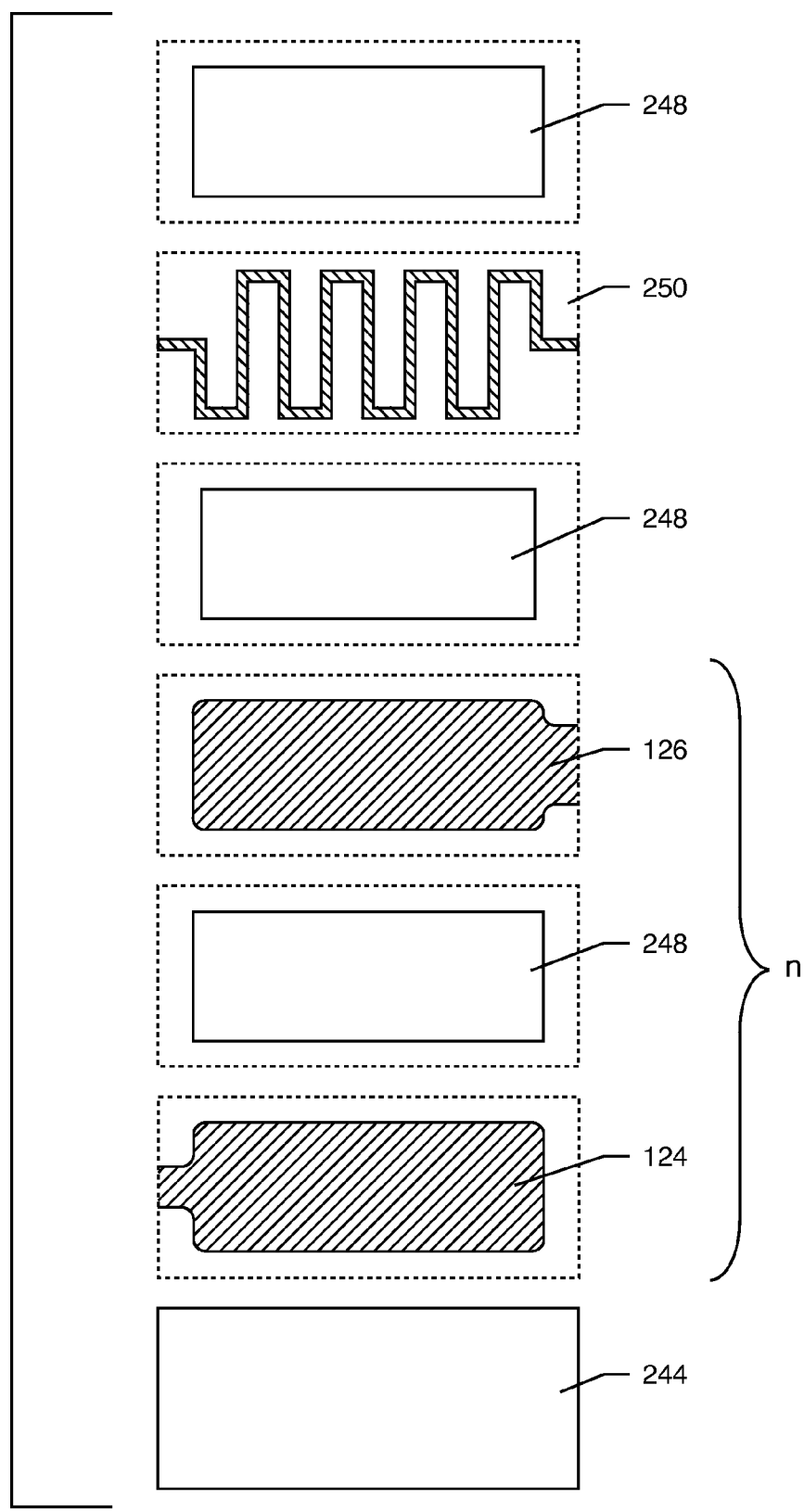
FIG. 68 illustrates the various layers utilized to manufacture the structure of FIG. 66.

FIG. 67 illustrates a schematic diagram of the novel tank illustrated in FIG. 66. The construction of FIG. 66 is best understood by referring to FIG. 68. In FIG. 68 one starts with a rigid substrate 244 which can be a voluminous, fiberglass, FR10 or other circuit board material. Thick film printed on top of substrate 244 is the first capacitor electrode 124. Then a blank inner leaf layer then one or more insulative inner leaf layers of ceramic dielectric 248 can be imprinted. The thickness and number of layers 248 depends upon the desired voltage rating of the capacitor. Then on top of the insulative layer 248 is the other capacitor electrode 126. As many as 400 alternating electrodes 126 and 124 can be laid up to achieve the desired capacitance value. Then typically another layer of blank ceramic 248 is added as an insulative surface. Then inductor layer 250 is printed on top of insulative 248. Then one or more blank insulative cover sheets 248 are put on top to add both mechanical and electrical integrity to the overall package shown in FIG. 66. This is then fired at high temperature which forms a dense and rugged monolithic structure suitable for use in accordance with the present invention.

All of the previously described band pass filters can also be adapted to be placed at various locations along the active implantable medical device lead wire system. These filters prevent current from circulating at selected frequencies of the medical therapeutic device. Fore example, for an MRI system operating at 1.5 Tesla, the pulse RF frequency is 64 MHz. The novel tank filters of the present invention can be designed to resonate at 64 MHz and thus create an open circuit in the lead wire system at that selected frequency. For example, the novel tank filter of the present invention, when placed at the distal TIP, will prevent currents from flowing through the distal TIP and also prevent currents from flowing into body tissue. It will be obvious to those skilled in the art that all of the embodiments described herein are equally applicable to a wide range of other active implantable medical devices including deep brain stimulators, spinal cord stimulators, drug pumps and the like. The present invention fulfills all of the needs regarding reduction or elimination of undesirable currents and associated heating in implanted lead wire systems. Moreover, the novel tank filter structures as described herein also have a broad application to other fields, including telecommunications, military, space and the like.

Electrically engineering a capacitor in parallel with an inductor is known as a tank filter. It is also well known that when the tank filter is at its resonant frequency, it will present a very high impedance. As described above, this is a basic principle of all radio receivers. In fact, multiple tank filters are often used to improve the selectivity of a radio receiver. One can adjust the resonant frequency of the tank circuit by either adjusting the capacitor value or the inductor value or both. Since medical diagnostic equipment which is capable of producing very large fields operates at discrete frequencies, this is an ideal situation for a specific band pass or tank filter. Tank filters are more efficient for eliminating one single frequency than broadband filters. Because the tank filter is targeted at this one frequency, it can be much smaller and volumetrically efficient. In addition, the way MRI couples with lead wire systems, various loops and associated currents are generated. For example, at the distal TIP of a cardiac pacemaker, direct electromagnetic forces (EMS) can be produced which result in current loops through the distal TIP and into the associated myocardial tissue. This current system is largely decoupled from the currents that are induced near the active implantable medical device, for example, near the cardiac pacemaker. There the MRI may set up a separate loop with its associated currents. Accordingly, one or more tank filters may be required to completely control all of the various induced EMI and associated currents in a lead wire system.

A major challenge for designing a tank filter for human implant is that it must be coaxial in nature and very small in size. The reason that it must be coaxial in nature is that lead wires are placed at locations in the human body by one of two main methods. These include guide wire lead insertion. For example, in a cardiac pacemaker application, a pectoral pocket is created. Then, the physician makes a small incision between the ribs and accesses the subclavian vein. The pacemaker lead wires are routed down through this venous system through the aortic arch, through the right atrium, through the tricuspid valve and into, for example, the right ventricle. Another primary method of installing lead wires in the human body is by tunneling. In tunneling, a surgeon uses special tools to tunnel under the skin, for example, up through the neck to access the Vagus nerve or the deep brain. In both techniques, it is very important that the lead wires and their associated electrodes at the distal TIPs be very small.

As previously mentioned, the value of the capacitance and the embedded inductor can be adjusted to achieve a specific resonant frequency. The novel band pass filter as described herein can be adapted to a number of locations within the overall active implantable medical device system. That is, the novel band pass filter can be incorporated at or near any part of the implanted lead wire system or the distal TIP. In addition, the novel band pass filter can be placed anywhere along the lead wire system.

The present invention is also applicable to probes and catheters. For example, ablation probes are used to selectively cauterize or burn tissue on the outside of the heart to control erratic pulses from the sinus node or the outside of the A-V node. These procedures are best performed during real time MRI imaging. However, a major concern is the overheating of the distal TIP at inappropriate times because of the induced currents from the MRI system. It will be obvious to one skilled in the art that the novel band pass tank filters of the present invention can be adapted to any probe, TIP or catheter that is used in the human body.

Thus, from the foregoing description it will be appreciated that the present invention is broadly directed to a hermetic terminal for an active implantable medical device (AIMD), comprising an RF distance telemetry pin antenna, a capacitor conductively coupled between the antenna and a ground for the AIMD, and an inductor electrically disposed in parallel with the capacitor and conductively coupled between the antenna and a ground for the AIMD. The capacitor and the inductor form a band pass filter for attenuating electromagnetic signals through the antenna except at a selected frequency band. Values of capacitance and inductance are selected such that the band pass filter is resonant at the selected frequency band.

In a preferred form, inductor Q is relatively maximized and capacitor Q is relatively minimized to reduce overall Q of the band pass filter. The inductor Q is relatively maximized by minimizing resistive loss in the inductor. The capacitor Q is relatively minimized by raising equivalent series resistance of the capacitor. However, this is not the only embodiment envisioned by the inventors. Indeed, inductor Q may be relatively minimized and capacitor Q may be relatively maximized to reduce the overall Q of the band pass filter, or, alternatively, both the inductor Q and the capacitor Q may be relatively minimized. The overall Q of the band pass filter may be reduced to permit passage of electromagnetic signals through the antenna along a range of selected frequency bands.

The AIMD may comprise a cochlear implant, a piezoelectric sound bridge transducer, a neurostimulator, a brain stimulator, a cardiac pacemaker, a ventricular assist device, an artificial heart, a drug pump, a bone growth stimulator, a bone fusion stimulator, a urinary incontinence device, a pain relief spinal cord stimulator, an anti-tremor stimulator, a gastric stimulator, an implantable cardioverter defibrillator, a congestive heart failure device, a neuromodulator, a cardiovascular stent, or an orthopedic implant.

The present invention further provides a process for designing the band pass filter. The process comprises the steps of (1) configuring the physical relationship of the capacitor and the inductor of the band pass filter based on the selected frequency band, (2) iteratively selecting component values for the capacitor and inductor of the band pass filter, and (3) analyzing the characteristics of the selected components to assess whether the band pass filter meets all design criteria for use in association with the hermetic terminal. The process further includes the steps of repeating the iteratively selecting and analyzing steps if the band pass filter does not meet all design criteria for use in association with the hermetic terminal, as well as the steps of building a prototype of the AIMD comprising a band pass filter having selected components that have been assessed to be acceptable, and testing the prototype to determine whether the band pass filter meets all criteria for use in association with the hermetic terminal. The configuring, iteratively selecting and analyzing steps may be repeated if the prototype fails the testing step.

With regard to the hermetic terminal itself, in a preferred embodiment the capacitor comprises a feedthrough capacitor which may form an electromagnetic interference (EMI) filter for a leadwire extending through the hermetic terminal. The inductor may be applied to the feedthrough capacitor. The inductor may form a spiral on the feedthrough capacitor which is conductively coupled between the antenna and the ground.

A substrate may be provided onto which the inductor is applied, which substrate is attached itself to the feedthrough capacitor. The inductor may comprise multiple inductors printed on respective opposite sides of one or more of said substrates. Moreover, the inductor may be embedded within the feedthrough capacitor. If so, the inductor may be disposed between adjacent layers of the feedthrough capacitor. The capacitor-inductor structure of the band pass filter may be formed utilizing a thick film deposition process.

In another embodiment, the inductor may comprise a chip inductor conductively coupled between the antenna and the ground. The chip inductor may include a meander inductor, a spiral inductor, or an inductor spiral formed about an insulator.

In yet other embodiments the capacitor may comprise a monolithic chip capacitor. A chip inductor may be utilized in connection with the monolithic chip capacitor. The capacitor and the inductor may be stacked adjacent to one another or disposed on a surface of the hermetic terminal, each being conductively coupled to both the antenna and the ground.

In yet another embodiment of the invention, the inductor may be applied to a surface of the monolithic chip capacitor. In this case, a substrate may be provided onto which the inductor is applied, and the inductor may comprise multiple inductors printed on opposite sides of one or more of said substrates. Moreover, the inductor may be embedded within the monolithic chip capacitor. The inductor may be disposed between adjacent layers of the monolithic chip capacitor, and the overall capacitor-inductor structure of the band pass filter may be formed utilizing a thick film deposition process.

One or more insulative layers may be disposed between the inductor and an adjacent capacitor plate when the inductor is embedded within the capacitor.

In an alternative preferred form of the invention, as viewed in FIGS. 69-74, a band pass or band stop filter or tank circuit 148 designed and constructed as previously shown and described herein can be coupled in series along the length of an RF telemetry pin or antenna 116 of an active medical device (AMD) for attenuating MRI signals of a selected frequency or frequency band. In this configuration, the tank circuit 148 effectively safeguards the medical device against potential damage, and related potential harmful effects to the patient, attributable to pulsed MRI signals encountered in the course of using magnetic resonance imaging as a diagnostic or surgical assistance tool.

More particularly, as shown in FIG. 69, an AIMD 100 of the general configuration shown and described previously herein with respect to FIGS. 1-6 includes an outer housing 102 of titanium or the like supporting a terminal assembly 106 secured thereto in a hermetically sealed manner as by laser welding a conductive ferrule 108 or the like to the AIMD housing 102. The telemetry pin or antenna 116 passes through an insulator block 136, such as a ceramic insulator block, supported by the ferrule 108 for bidirectional transmitting of telemetry signals between the exterior of the housing 102 and internally mounted electronic receiver components (not shown). In addition, at least one and preferably multiple conductive lead wires such as the illustrative lead wires 104*a*, 104*b*, 104*c* and 104*d* (FIG. 70) also pass through the insulator block 136 for transmitting pacemaker signals or the like through the terminal assembly 106 to internally mounted electronic components (also not shown) of the AIMD. As previously shown and described with respect to FIGS. 1-6, the passage of the telemetry pin 116 and the lead wires 104a-104d through the insulator block 136 of the terminal assembly 106 are individually hermetically sealed.

In addition, as also previously shown and described in FIGS. 1-6, a broadband filter in the form of a feedthrough capacitor 120 is carried at an inboard side of the terminal assembly 106 and is associated with the lead wires 104a-104d for shunting undesired EMI signals to a ground plane defined by the ferrule 108 and outer housing 102 of the AIMD. This feedthrough capacitor 120 generally includes a first set of capacitor plates 126 coupled to each of the lead wires, and a second set of capacitor plates 124 coupled as by means of external metallization 122 or the like to the conductive ferrule 108. Such feedthrough capacitor 120 is known in the art.

The feedthrough capacitor 120 is not associated with the RF telemetry pin 116. Instead, the band pass filter or tank circuit 148 is connected in-line, or in series, along the length of the telemetry pin 116 generally at the inboard side of the terminal assembly 106. FIG. 70 shows the band pass filter 148 in schematic form to incorporate a capacitor $C_r$ and an inductor $L_r$ coupled in parallel relation to each other, and in series with the telemetry pin 116. FIG. 70 also shows the feedthrough capacitor in the form of individual capacitances $C_1$, $C_2$, $C_3$, and $C_4$, associated respectively with lead wires 104a, 104b, 104c, and 104d.

FIG. 71 is a schematic drawing of the band pass filter or tank circuit 148 of FIG. 70, except in this case the inductor $L_r$ and the capacitor $C_r$ are not ideal. That is, the capacitor $C_r$ has its own internal resistance $R_c$, which is otherwise known in the industry as dissipation factor or equivalent series resistance (ESR). The inductor $L_r$ also has a resistance $R_L$. For those that are experienced in passive components, one would realize that the inductor $L_r$ would also have some parallel capacitance. This parasitic capacitance comes from the capacitance associated with adjacent turns. However, the inductance value contemplated is so low that one can assume that at MRI pulse frequencies, the inductor's parallel capacitance is negligible. One could also state that the capacitor $C_r$ also has some internal inductance which would appear in series. However, the novel capacitors described below are very small or coaxial and have negligible series inductance. Accordingly, the circuit shown in FIG. 71 is a very good approximation model for the novel band pass filter circuits 148 as described herein.

This is best understood by looking at the FIG. 71 circuit 148 at the frequency extremes. At very low frequency, the inductor reactance equation is $X_L=2\pi fL$. At these low frequencies, the inductive reactance $X_L$ will be very close to zero ohms. Over this range, on the other hand, the capacitive reactance $X_C$ which has the equation $X_C=1/(2\pi fc)$ will look like an infinite or open circuit. As such, at low frequencies, the impedance between points A and B in FIG. 71 will equal to $R_L$. Accordingly, the resistance of the inductor ($R_L$) should be kept as small as possible to minimize attenuation of signals. It also indicates that the amount of capacitive loss $R_C$ is not particularly important. As a matter of fact, it would be desirable if that loss were fairly high so as to not freely pass very high frequency signals (such as undesirable EMI from cellular phones). It is also desirable to have the Q of the circuit shown in FIG. 71 relatively low so that the band stop frequency bandwidth can be a little wider. In other words, in a preferred embodiment, it would be possible to have a band stop wide enough to block both 64 MHz and 128 MHz frequencies thereby making the medical device compatible for use in both of common 1.5 Tesla and 3 Tesla MRI systems.

Figure 72:
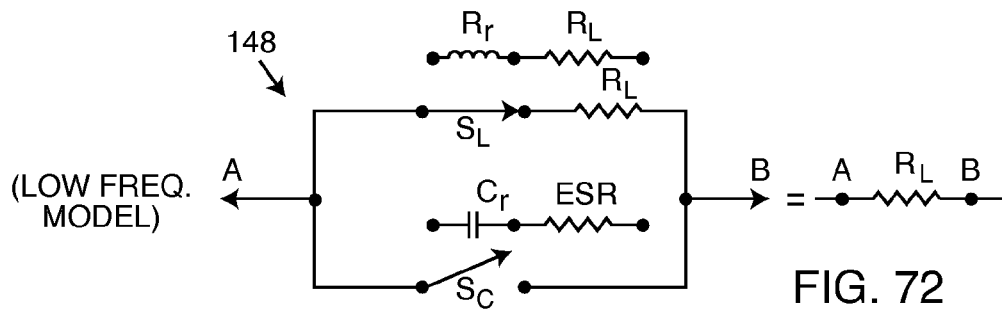
FIG. 72 is a schematic diagram similar to FIG. 72, illustrating a low frequency model of the band stop filter, using switches to illustrate its function.
Figure 73:
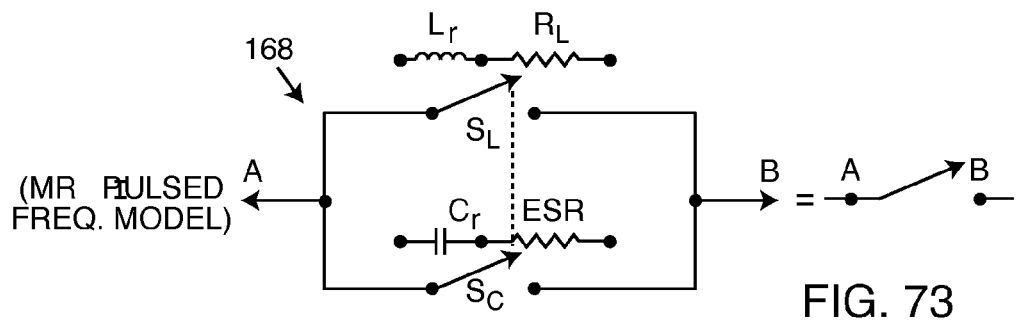
FIG. 73 is a schematic diagram similar to FIG. 72, illustrating the model of the band stop filter at its resonant frequency.
Figure 74:
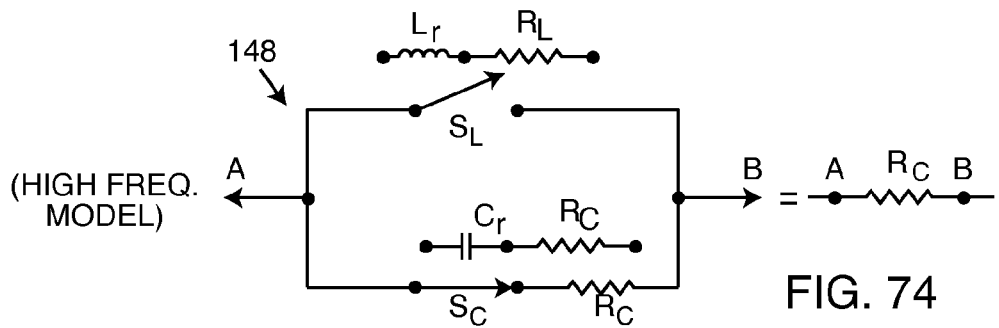
FIG. 74 is a schematic diagram similar to FIGS. 72-73, illustrating a model of the band stop filter at high frequencies well above the resonant frequency.

FIGS. 72-74 are representations of the band stop filter or tank circuit 148 using switches that open and close at various frequencies to illustrate its function. Inductor $L_r$ has been replaced with a switch $S_L$. When the impedance of the inductor is quite low, the switch $S_L$ will be closed. When the impedance or inductive reactance of the inductor is high, the switch $S_L$ will be shown open. There is a corresponding analogy for the capacitor element $C_r$. When the capacitive reactance looks like a very low impedance, the capacitor switch $S_C$ will be shown closed. When the capacitive reactance is shown as a very high impedance, the switch $S_C$ will be shown open.

More particularly, FIG. 72 is the low frequency model of the band stop filter 148. At low frequencies, capacitors tend to look like open circuits and inductors tend to look like short circuits. Accordingly, switch $S_L$ is closed and switch $S_C$ is open. This is an indication that at frequencies below the resonant frequency of the band stop filter 148 that signals will pass along the telemetry pin 116 through the inductor element and its corresponding resistance $R_L$.

FIG. 73 is a model of the novel band stop filter 148 at its resonant frequency. By definition, when a parallel tank circuit is at resonance, it presents a very high impedance to the overall circuit. Accordingly, both switches $S_L$ and $S_C$ are shown open. For example, this is how the band stop filter 148 prevents or blocks the flow of pulsed MRI signals along the telemetry pin 116, thereby safeguarding the internal AIMD electronics against potential damage.

FIG. 74 is a model of the band stop filter 148 at high frequency. At high frequencies, inductors tend to look like open circuits. Accordingly, switch $S_L$ is shown open. At high frequencies, ideal capacitors tend to look like short circuits, hence switch $S_C$ is closed to permit signal transmission along the telemetry pin 116.

Accordingly, by constructing the capacitor and inductor elements for resonance at a selected frequency, or range of selected frequencies, as previously shown and described herein, the band pass filter 148 provides a virtually infinite impedance at the resonant frequency and thereby functions as an open circuit effectively blocking passage of the selected frequency along the telemetry pin 116 into the interior of the AIMD.

The optimum Q factor for the band stop filter 148 of the present invention will, in the preferred form, embody a high Q factor for the inductor L and a relatively low Q factor for the capacitor C, thereby producing a filter 148 which is resonant at a range of selected or target frequencies. By designing the resonant frequency band width to accommodate know MRI pulse frequencies, such as a band width encompassing both the common 1.5 Tesla and 3 Tesla MRI systems, pulsed MRI frequencies are effectively blocked while permitting substantially unobstructed passage along the telemetry pin 116 of telemetry signals outside the resonant frequency band width. Persons skilled in the art will recognize and appreciate that the filter 148 may be designed for resonance at other, typically higher frequencies.

Figure 75:
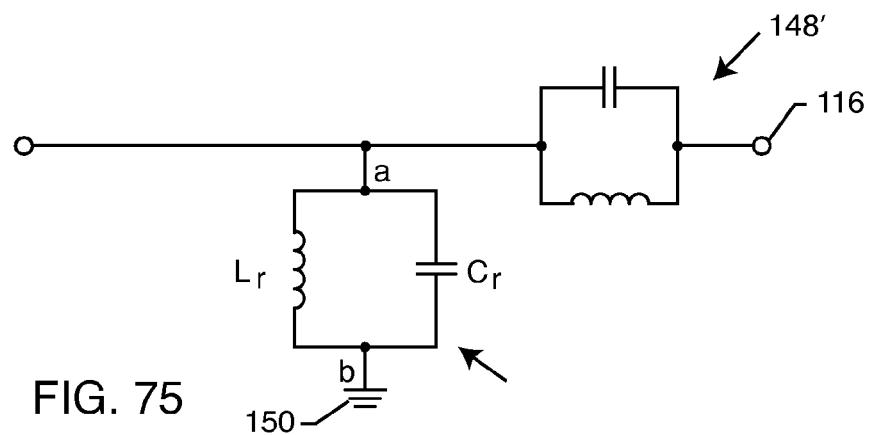
FIG. 75 is a schematic circuit diagram similar to FIG. 71, but depicting a further alternative preferred form of the invention.

FIG. 75 is an electrical circuit diagram depicting a further alternative form of the invention, wherein the embodiments of FIGS. 10-13 and FIGS. 69-71 are combined. That is, a first band pass filter 148 is coupled between the telemetry pin or antenna 116 and a ground plane 150 for protecting the telemetry circuitry against adverse affects attributable to stray EMI signals. In addition, a second band pass filter 148' is coupled in series with the telemetry pin 116 for safeguarding against pulsed MRI signals.

Although several embodiments have been described in detail for purposes of illustration, various modifications may be made without departing from the scope and spirit of the invention. Accordingly, the invention is not to be limited, except as by the following claims.

What is claimed is:

1. An active medical device (AMD), comprising:
   a) a housing for the AMD;
   b) an electronic circuit board or substrate disposed on an inboard side opposite an outboard body fluid side of the housing;
   c) a hermetic feedthrough terminal, comprising:
      i) a ferrule comprising a ferrule sidewall having an outer surface spaced from an inner surface, wherein the outer ferrule surface is hermetically sealed to an opening in the housing and wherein the inner ferrule surface defines a ferrule opening, the ferrule opening extending to spaced apart first and second ferrule end surfaces;
      ii) an insulator disposed in the ferrule opening hermetically sealed to the inner ferrule surface, the insulator having at least a first via and a second via, both vias extending to the spaced apart first and second insulator end surfaces disposed proximate the respective first and second ferrule end surfaces;
      iii) a first conductive lead wire extending through the first via and hermetically sealed to the insulator;
   d) at least one first capacitor mounted to the feedthrough terminal and comprising at least one first active electrode plate spaced apart from at least one first ground electrode plate encased in a dielectric, wherein the first lead wire is electrically connected to the first active electrode plate of the first capacitor with the first ground electrode plate being electrically connected to the ferrule and the AND housing;
   e) a second electrically conductive pin extending through the second via and hermetically sealed to the insulator in a non-conductive relation with the ferrule and the AND housing, wherein the second conductive pin has a proximal pin portion spaced from a distal pin portion, the proximal pin portion being electrically connected to the electronic circuit board or substrate disposed within the housing with the distal pin portion extending from the insulator opposite the first capacitor; and
   f) a band stop filter, comprising:
      i) at least one second active electrode plate electrically connected to the second conductive pin, but spaced from the first lead wire, the second active electrode plate being in a spaced, capacitive relationship within the dielectric with the first ground electrode plate of the first capacitor to thereby form a second capacitor;
      ii) an inductor segment extending from a proximal inductor segment end to a distal inductor segment end, wherein the proximal end of the inductor segment and the second active electrode plate are directly electrically connected to the second conductive pin at a first node between the proximal and distal pin portions and wherein the distal end of the inductor segment and the first ground electrode plate are directly electrically connected to the ferrule and then the AMD housing at a second node to thereby provide the band stop filter comprising the inductor segment directly electrically connected from the first node to the second node in parallel with the second capacitor.

2. The active medical device of claim 1, wherein a Q factor for the inductor is relatively maximized and a Q factor for the capacitor is relatively minimized to reduce the overall Q of the band stop filter.

3. The active medical device of claim 2, wherein the Q factor for the inductor is relatively maximized by minimizing resistive loss in the inductor.

4. The active medical device of claim 2, wherein the Q factor for the capacitor is relatively minimized by raising equivalent series resistance of the capacitor.

5. The active medical device of claim 1, wherein the AMD is selected from the group consisting of a cochlear implant, a piezoelectric sound bridge transducer, a neurostimulator, a brain stimulator, a cardiac pacemaker, a ventricular assist device, an artificial heart, a drug pump, a bone growth stimulator, a bone fusion stimulator, a urinary incontinence device, a pain relief spinal cord stimulator, an anti-tremor stimulator, a gastric stimulator, an implantable cardioverter defibrillator, a congestive heart failure device, a neuromodulator, a cardiovascular stent, or an orthopedic implant.

6. The active medical device of claim 1 wherein the band stop filter is disposed at an inboard side of the hermetic feedthrough terminal.

7. The active medical device of claim 1 wherein the first lead wire is connectable to an electrode that is adapted for contact. with patient tissue.

8. The active medical device of claim 1 further including a second band stop filter comprising a third capacitor in parallel with a second inductor and coupled between the second conductive pin and a ground plane, the second band stop filter having a 3-dB bandwidth in the megahertz range that has a resonant center frequency that is different than that of the first band stop filter.

9. An active medical device (AMD), comprising:
   a) a housing for the AMD;
   b) an electronic circuit board or substrate disposed on an inboard side opposite an outboard body fluid side of the housing;
   c) a hermetic feedthrough terminal, comprising:
      i) a ferrule comprising a ferrule sidewall having an outer surface spaced from an inner surface, wherein the outer ferrule surface is hermetically sealed to an opening in the housing and wherein the inner ferrule surface defines a ferrule opening, the ferrule opening extending to spaced apart first and second ferrule end surfaces;
      ii) an insulator disposed in the ferrule opening and hermetically sealed to the inner ferrule surface, the insulator having at least a first via and a second via, both vias extending to the spaced apart first and second insulator end surfaces disposed proximate the respective first and second ferrule end surfaces;
      iii) a first conductive lead wire extending through the first via and hermetically sealed to the insulator;
   d) at least one first capacitor mounted to the feedthrough terminal and comprising at least one first active electrode plate spaced apart from at least one first ground electrode plate encased in a dielectric, wherein the first lead wire is electrically connected to the first active electrode plate of the first capacitor with the first ground electrode plate being electrically connected to the ferrule and the AMD housing;
   e) a second electrically conductive pin extending through the second via and hermetically sealed to the insulator in a non-conductive relation with the ferrule and the AMU housing, wherein the second conductive pin has a proximal pin portion spaced from a distal pin portion, the proximal pin portion being electrically connected to the electronic circuit board. or substrate disposed within the housing with the distal pin portion extending from the insulator opposite the first capacitor; and f) a first band stop filter, comprising:
  i) at least one second active electrode plate electrically connected to the second conductive pin, but spaced from the first lead wire, the second. conductive electrode plate being in a spaced, but capacitive relationship within the dielectric with the first ground electrode plate of the first capacitor to thereby form a second capacitor;
  ii) an inductor segment extending from a proximal inductor segment end to a distal inductor segment end, wherein the proximal end of the inductor segment and the second active electrode plate are directly electrically connected to the second conductive pin at a first node between the proximal and distal pin portions and wherein the distal end of the inductor segment and the first ground electrode plate are directly electrically connected to the ferrule and then the AMD housing at a second node to thereby provide the band stop filter comprising the inductor segment directly electrically connecting from the first node to the second node in parallel with the second capacitor,
g) wherein the band stop filter has a 3-dB bandwidth in the megahertz range; and
h) a second band stop filter comprising a third capacitor in parallel with a second inductor and coupled between the second conductive pin and a ground plane, the second band stop filter having a 3-dB bandwidth in the megahertz range that has a resonant center frequency that is different than that of the first band stop filter.

10. The active medical device of claim 1 wherein the band stop filter has a 3-dB bandwidth in the megahertz range.

11. The active medical device of claim 10 wherein the 3-dB bandwidth of the band stop filter includes pulsed MRI signals.

* * * * *

UNITED STATES PATENT AND TRADEMARK OFFICE
CERTIFICATE OF CORRECTION

PATENT NO.         : 9,042,999 B2                                  Page 1 of 1
APPLICATION NO.    : 11/840131
DATED              : May 26, 2015
INVENTOR(S)        : Robert A. Stevenson and Warren S. Dabney It is certified that error appears in the above-identified patent and that said Letters Patent is hereby corrected as shown below:

In the drawings,

Sheet 9 of 32, Figure 17 delete "tTnk" on the right y axis label and insert --Tank--

Sheet 29 of 32, Figure 65 delete "Aol" in right column 4th entry of the Table and insert --Al--

In the specification,

Column 33, line 37 delete "Fig. 66 Illustrates"

In the claims,

Column 39, line 34 (Claim 1, line 29) delete "AND" and insert --AMD--

Column 39, line 37 (Claim 1, line 33) delete "AND" and insert --AMD--

Column 40, line 61 (Claim 9, line 32) delete "AMU" and insert --AMD--

Column 41, line 4 (Claim 9, line 42) after the word "second" delete the "."

Signed and Sealed this
Nineteenth Day of January, 2016

Michelle K. Lee
*Director of the United States Patent and Trademark Office*